(12) United States Patent
Zhang et al.

(10) Patent No.: US 9,598,401 B2
(45) Date of Patent: Mar. 21, 2017

(54) SUBSTITUTED HETEROARYL COMPOUNDS AND METHODS OF USE THEREOF

(71) Applicant: Sunshine Lake Pharma Co., Ltd., Dongguan, Guangdong (CN)

(72) Inventors: Yingjun Zhang, Dongguan (CN); Chuanfei Jin, Dongguan (CN); Rongqi Zhou, Dongguan (CN)

(73) Assignee: SUNSHINE LAKE PHARMA CO., LTD., Dongguan, Guangdong (CN)

( * ) Notice: Subject to any disclaimer, the term of this patent is extended or adjusted under 35 U.S.C. 154(b) by 0 days.

(21) Appl. No.: 14/787,774

(22) PCT Filed: Jul. 28, 2014

(86) PCT No.: PCT/CN2014/083135
§ 371 (c)(1),
(2) Date: Oct. 29, 2015

(87) PCT Pub. No.: WO2015/014256
PCT Pub. Date: Feb. 5, 2015

(65) Prior Publication Data
US 2016/0083370 A1    Mar. 24, 2016

(30) Foreign Application Priority Data

Jul. 29, 2013  (CN) .......................... 2013 1 0322334

(51) Int. Cl.
| | | |
|---|---|---|
| *A61K 31/506* | (2006.01) | |
| *C07D 403/12* | (2006.01) | |
| *A61K 31/496* | (2006.01) | |
| *C07D 417/12* | (2006.01) | |
| *A61K 45/06* | (2006.01) | |
| *C07D 403/14* | (2006.01) | |
| *C07D 417/14* | (2006.01) | |

(52) U.S. Cl.
CPC .......... *C07D 403/12* (2013.01); *A61K 31/496* (2013.01); *A61K 31/506* (2013.01); *A61K 45/06* (2013.01); *C07D 403/14* (2013.01); *C07D 417/12* (2013.01); *C07D 417/14* (2013.01)

(58) Field of Classification Search
CPC .. C07D 401/14; C07D 403/14; C07D 409/14; C07D 413/14
See application file for complete search history.

(56) References Cited

U.S. PATENT DOCUMENTS

| | | |
|---|---|---|
| 3,188,313 A | 6/1965 | Archer |
| 4,954,502 A | 9/1990 | Smith et al. |
| 4,954,503 A | 9/1990 | Strupczewski et al. |
| 5,002,948 A | 3/1991 | Perregaard et al. |
| 5,010,079 A | 4/1991 | Manoury et al. |
| 5,077,293 A | 12/1991 | Smith et al. |
| 5,106,850 A | 4/1992 | Butcher et al. |
| 5,242,925 A | 9/1993 | Boettcher et al. |
| 5,270,312 A | 12/1993 | Glase et al. |
| 5,300,506 A | 4/1994 | Smith et al. |
| 5,418,237 A | 5/1995 | Bottcher et al. |
| 5,434,154 A | 7/1995 | Smith et al. |
| 5,521,188 A | 5/1996 | Gylys et al. |
| 5,532,241 A | 7/1996 | Bottcher et al. |
| 5,550,239 A | 8/1996 | Humora et al. |
| 5,614,524 A | 3/1997 | Matassa et al. |
| 5,618,816 A | 4/1997 | Crenshaw et al. |
| 5,681,954 A | 10/1997 | Yamamoto et al. |
| 5,763,444 A | 6/1998 | Smith et al. |
| 6,251,908 B1 | 6/2001 | Bottcher et al. |
| 6,310,068 B1 | 10/2001 | Bottcher et al. |
| 6,476,035 B1 | 11/2002 | Moltzen et al. |
| 6,486,153 B1 | 11/2002 | Castro Pineiro et al. |
| 6,518,273 B1 | 2/2003 | Chapman et al. |
| 6,596,722 B2 | 7/2003 | Moltzen et al. |
| 7,244,846 B2 | 7/2007 | Dorsch et al. |
| 7,276,603 B2 | 10/2007 | Venkatesan et al. |
| 7,332,495 B2 | 2/2008 | Li et al. |
| 7,576,086 B2 | 8/2009 | Li et al. |
| 7,829,565 B2 | 11/2010 | Heinrich et al. |
| 7,968,551 B2 | 6/2011 | Schiemann et al. |
| 8,680,097 B2 | 3/2014 | Li et al. |

(Continued)

FOREIGN PATENT DOCUMENTS

| | | |
|---|---|---|
| CN | 1184478 A | 6/1998 |
| CN | 102372703 A | 3/2012 |

(Continued)

OTHER PUBLICATIONS

B Testa et al., Prodrug Design in, 5 Encyclopedia of Pharmaceutical Technology, 3008-3014 (J. Swarbrick ed., 3rd ed., 2007).*
H. Girouard et al., 100 Journal of Applied Physiology, 328-335, 332 (2006).*
R. S. Shah et al., 52 Biomedicine & Pharmacotherapy, 199-207 (2008).*
J.T. O'Brien et al., 2 The Lancet Neurology, 89-98, 96 (2003).*
P.A. LeWitt, 359 New England Journal of Medicine, 2468-2473 (2008).*
S. Judge et al., 111 Pharmacology & Therapeutics, 224-259 (2006).*
V. Brinkmann et al., 9 Nature Reviews | Drug Discovery, 883-897 (2010).*
J.D. Mitchell et al., 369 The Lancet, 2031-2041 (2007).*
Y. Agid et al., 6 Nature Reviews | Drug Discovery 189-201, 189 (2007).*
Llado-Pelfort et al., 22 Cerebral Cortex, 1487-1487 (2012).*
P. Celada et al., 27 CNS Drugs, 703-716 (2013).*

(Continued)

*Primary Examiner* — Alexander R Pagano
(74) *Attorney, Agent, or Firm* — Kam W. Law; Squire Patton Boggs (US) LLP

(57) ABSTRACT

Provided herein are novel heteroaryl compounds, pharmaceutically acceptable salts and pharmaceutical formulations thereof for selectively inhibiting serotonin reuptake and/or acting as 5-HT$_{1A}$ receptor agonists. Also provided herein are pharmaceutical compositions comprising the heteroaryl compounds and methods of using the pharmaceutical compositions in treating central nervous system (CNS) dysfunction in a mammal, especially a human being.

19 Claims, No Drawings

(56) References Cited

U.S. PATENT DOCUMENTS

| | | |
|---|---|---|
| 2006/0122175 A1 | 6/2006 | Hes et al. |
| 2006/0122191 A1 | 6/2006 | Heinrich et al. |
| 2006/0160824 A1 | 7/2006 | Heinrich et al. |
| 2009/0054454 A1 | 2/2009 | Venkatesan et al. |
| 2009/0238761 A1 | 9/2009 | Campiani et al. |
| 2011/0059982 A1 | 3/2011 | Heinrich et al. |
| 2013/0064770 A1 | 3/2013 | Newington et al. |

FOREIGN PATENT DOCUMENTS

| | | | |
|---|---|---|---|
| CN | 102993186 A | 3/2013 | |
| CN | 104163813 A | 11/2014 | |
| DE | WO 2004041815 A1 * | 5/2004 | ........... C07D 417/12 |
| EP | 1078928 A1 | 2/2001 | |
| JP | H0641071 A | 2/1994 | |
| JP | 2002053553 A | 2/2002 | |
| WO | 9535293 A1 | 12/1995 | |
| WO | 9967237 A1 | 12/1999 | |
| WO | 0114330 A2 | 3/2001 | |
| WO | 0149679 A1 | 7/2001 | |
| WO | 0244170 A2 | 6/2002 | |
| WO | 03070723 A1 | 8/2003 | |
| WO | 03076400 A1 | 9/2003 | |
| WO | 03101994 A1 | 12/2003 | |
| WO | 2004041815 A1 | 5/2004 | |
| WO | 2006061374 A1 | 6/2006 | |
| WO | 2006061377 A1 | 6/2006 | |
| WO | 2006061379 A1 | 6/2006 | |
| WO | 2012170209 A2 | 12/2012 | |

OTHER PUBLICATIONS

Newman-Tancredi et al., 216 Psychopharmacology, 451-473 (2011).*
Ono, 17 CNS Neuroscience & Therapeutics, 59-65 (2010).*
G.J. Yohrling et al., 82 Journal of Neurochemistry, 1416-1423 (2002).*
Pessoa-Mahana et al., Synthesis, 5-hydroxytryptamine1A receptor affinity and docking studies of 3-[3-(4-aryl-1-piperazinyl)-propyl]-1H-indole derivatives, Chemical and Pharmaceutical Bulletin, 2012, 60(5): 632-638.
Heinrich et al., Indolebutylamines as Selective 5-HT1A Agonists, Journal of Medicinal Chemistry, 2004, 47(19): 4677-4683.
International Search Report of PCT/CN2014/083135.
Written Opinion of PCT/CN2014/083135.

* cited by examiner

SUBSTITUTED HETEROARYL COMPOUNDS AND METHODS OF USE THEREOF

CROSS-REFERENCE TO RELATED APPLICATIONS

This is a U.S. national stage application of the International Patent Application No. PCT/CN2014/083135, filed 28 Jul. 2014, which claims priority to Chinese Patent Application No. 201310322334.6, filed 29 Jul. 2013, both of which are incorporated herein by reference in their entirety.

FIELD OF THE INVENTION

The present invention belongs to the field of pharmaceutical technology, and more specifically relates to novel compounds, compositions and methods of use thereof for treating central nervous system dysfunction. Particularly, provided herein are substituted heteroaryl compounds acting as 5-serotonin reuptake inhibitors and/or $5\text{-HT}_{1A}$ receptor agonists.

BACKGROUND OF THE INVENTION

Serotonin, a neurotransmitter that carries signal in the brain and nerves, plays a very important role in central nervous system (CNS) dysfunction, especially in anxiety, depression, aggression and impulsivity. Regulation of the central nervous system dysfunction is possible either by antagonistic or agonistic action on a certain type of the serotonin receptors. To date, at least 14 different serotonin receptors have been identified. These receptors can be divided into distinct families—denoted $5\text{-HT}_1$, $5\text{-HT}_2$, $5\text{-HT}_3$, $5\text{-HT}_4$, $5\text{-HT}_5$, $5\text{-HT}_6$ and $5\text{-HT}_7$, with subtypes in each family denoted by letters such as a, b and c. Central serotonergic neurons are located in the raphe nuclei in the brain stem. The $5\text{-HT}_{1A}$ receptor is a G-protein-coupled receptor widely distributed in regions that receive serotonergic input from the raphe nuclei: the frontal cortex, septum, amygdala, hippocampus, and hypothalamus. In these cortico-limbic regions, $5\text{-HT}_{1A}$ is distributed post-synaptically. The $5\text{-HT}_{1A}$ receptor also serves as the predominant (somatodendritic) autoreceptor of the raphe nuclei, reducing the firing rate of neurons (the amount of serotonin released per action potential), the synthesis of the neurotransmitter, and thus by implication, the serotonergic activity of its projection areas. Activation of the presynaptic $5\text{-HT}_{1A}$ receptor may also indirectly reduce serotonergic transmission through the inhibition of tyrosine hydroxylase synthesis, as well as the activity of glutamatergic pathway that originates in the medial prefrontal cortex and projects to the raphe nuclei (Jonathan Savitz et al., "$5\text{-HT}_{1A}$ receptor function in major depressive disorder," *Prog. Neurobiol.*, 2009, 88(1): 17-31).

Depression is the most important of all therapeutic indications related to 5-HT disorder since it is the fourth leading burdensome disease in the world according to the World Health Organization. By 2020, depression is projected to rank second in disability-adjusted life years (Bromet E et al., "Cross-national epidemiology of DSM-IV major depressive episode," *BMC Med.*, 2011, 9: 90).

Historically, tricyclic antidepressants (TCAs) and monoamine oxidase inhibitors (MAOIs) revolutionized the pharmacologic treatment of mood disorders in the 1950s, mostly by blocking neurotransmitter (dopamine, norepinephrine, and serotonin). However, the non-selectivity and undesirable side effect eventually limited their use. In 1980s, the discovery of selective serotonin reuptake inhibitors (SSRIs) changed the landscape. As a class, the SSRIs boast similar efficacy compared to the TCAs, and an improved AE profile with less tendency for toxicity in overdose (Sarko J, "Andidepressant, old and new. A review of their adverse effects and toxicity in overdose," *Emerg. Med. Clin North Am.*, 2000, 18 (4): 637-54).

Conventional SSRIs therapeutically increase available serotonin by inhibiting its reuptake and modulating its transmission. Administration of SSRIs also pleiotropically stimulates pre-synaptic $5\text{-HT}_{1A}$ autoreceptors, which acutely decreases the release of serotonin and subsequently reduces serotonin concentrations in the synapse. After chronic administration, the stimulation of the $5\text{-HT}_{1A}$ autoreceptors is overcome via desensitization and the SSRIs is able to normalize serotonergic transmission. It is postulated that this stimulation of the autoreceptor is the causative factor in the delayed therapeutic effect of the SSRIs (Celada P et al., "The therapeutic role of $5\text{-HT}_{1A}$ and $5\text{-HT}_{2A}$ receptors in depression," *J Psychiatry Neurosci.*, 2004, 29(4): 252-65). Thus, overriding the negative feedback effect of $5\text{-HT}_{1A}$ autoreceptors antagonists holds the promise of increasing and accelerating clinical antidepressant effects.

Compared to SSRIs, $5\text{-HT}_{1A}$ receptor agonists or partial agonists act directly on postsynaptic serotonin receptors to increase serotonin neurotransmission during the SSRI latency effect period. Feiger and Wilcox demonstrated that the buspirone and gepirone were clinically effective $5\text{-HT}_{1A}$ partial agonists (Feiger, A, *Psychopharmacol. Bull.*, 1996, 32: 659-65). The addition of buspirone to standard SSRI treatment produced a marked improvement in patients previously unresponsive to standard treatment for depression (Dimitriou, E. J., *Clin. Psychopharmacol.*, 1998, 18: 465-9).

Provided herein are novel compounds believed to have clinical use in treating CNS disorders through selectively inhibiting serotonin reuptake and/or acting as $5\text{-HT}_{1A}$ receptor agonists. The compounds disclosed herein are also believed to provide an improvement in potency, pharmacokinetic properties, and/or toxicity profile over certain counterparts found in the art.

SUMMARY OF THE INVENTION

This section merely summarizes certain aspects disclosed herein and is not intended to be limiting in nature. These aspects and other aspects are described more fully below. All the documents cited in the present specification are hereby incorporated herein by reference in their entireties. Where the disclosure of the present specification is inconsistent with a patent, application, or publication incorporated by reference, the disclosure of the present specification shall prevail.

Provided herein are novel compounds acting as selective serotonin reuptake inhibitors and/or the $5\text{-HT}_{1A}$ receptor agonists. The compounds can be used to manufacture medicaments for the treatment of human central nervous system (CNS) dysfunction, such as depression, anxiety disorder and bipolar disorder.

Provided herein also are methods for preparing the novel compounds disclosed herein and pharmaceutical compositions containing the compounds.

In one aspect, provided herein are compounds having Formula (I) or a stereoisomer, a tautomer, an N-oxide, a solvate, a metabolite, a pharmaceutically acceptable salt or a prodrug thereof,

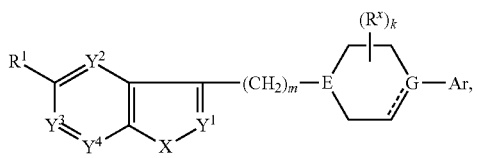

wherein
X is O, S or NH;
$Y^1$ is CH or N;
$Y^2$ is $CR^2$ or N;
$Y^3$ is $CR^3$ or N;
$Y^4$ is $CR^4$ or N;
E is N or CH;
==== is either a single bond or a double bond, provided that: (1) when ==== is a single bond, G is CH or N; or (2) when ==== is a double bond, G is C;
Ar is

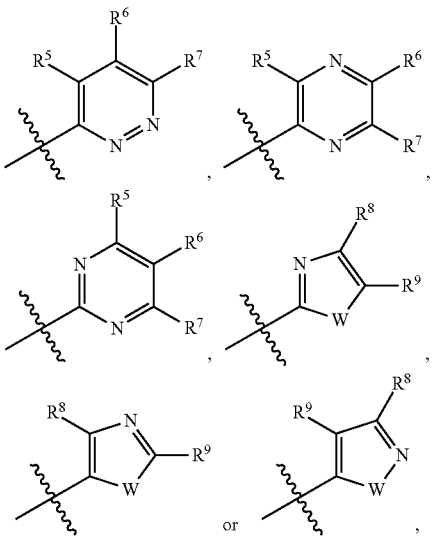

wherein each W is independently O, S or NH;
each $R^x$ is independently D, F, Cl, $C_1$-$C_6$ alkyl, $C_1$-$C_6$ haloalkyl, $-NR^{11}R^{11a}$, $-OR^{10}$, $-(C_1$-$C_6$ alkylene)-$NR^{11}R^{11a}$, $(C_1$-$C_6$ alkylene)-$OR^{10}$, $-C(=O)R^{10}$, $-C(=O)OR^{10}$, $-C(=O)NR^{11}R^{11a}$ or $-(C_1$-$C_6$ alkylene)-aryl, or two $R^x$ on two adjacent ring carbon atoms, together with the ring carbon atoms to which they are attached, form a $C_3$-$C_6$ carbocyclic or 3-6 membered heterocyclic ring;
k is 0, 1, 2, 3 or 4;
each of $R^1$, $R^2$, $R^3$ and $R^4$ is independently H, D, F, Cl, Br, I, $NO_2$, CN, —SCN, $-OR^{10}$, $-SR^{10}$, $-NR^{11}R^{11a}$, $-C(=O)R^{10}$, $-C(=O)OR^{10}$, $-C(=O)NR^{11}R^{11a}$, $-OC(=O)R^{10}$, $-S(=O)R^{10}$, $-S(=O)_2R^{10}$, $-S(=O)_2OR^{10}$, $-S(=O)_2NR^{11}R^{11a}$, $-N(R^{11})C(=O)R^{10}$, $-N(R^{11})S(=O)_2R^{10}$, alkyl, alkenyl, alkynyl, haloalkyl, cycloalkyl, cycloalkylalkylene, heterocyclyl, heterocyclylalkylene, aryl, arylalkylene, heteroaryl or heteroarylalkylene, wherein each of alkyl, alkenyl, alkynyl, haloalkyl, cycloalkyl, cycloalkylalkylene, heterocyclyl, heterocyclylalkylene, aryl, arylalkylene, heteroaryl and heteroarylalkylene is optionally substituted with one or more substituents independently selected from D, F, Cl, $N_3$, CN, OH, SH, $NH_2$, alkyl, alkoxy, alkylthio and alkylamino;

each $R^5$, $R^6$ and $R^7$ is independently H, D, F, Cl, Br, I, $NO_2$, CN, $NH_2$, $-C(=O)R^{10}$, $-C(=O)OR^{10}$, $-C(=O)NR^{11}R^{11a}$, -alkylene-$C(=O)NR^{11}R^{11a}$, $-OC(=O)R^{10}$, $-N(R^{11})C(=O)R^{10}$, $-S(=O)R^{10}$, $-S(=O)_2R^{10}$, $-S(=O)_2OR^{10}$, $-S(=O)_2NR^{11}R^{11a}$, $-N(R^{11})S(=O)_2R^{10}$, alkyl, alkenyl, alkynyl, haloalkyl, alkoxy, alkylthio, alkylamino, cycloalkyl, cycloalkylalkylene, heterocyclyl, heterocyclylalkylene, aryl, arylalkylene, heteroaryl or heteroarylalkylene, with the proviso that at least one of $R^5$, $R^6$ and $R^7$ is not H, wherein each of alkyl, alkenyl, alkynyl, haloalkyl, alkoxy, alkylthio, alkylamino, cycloalkyl, cycloalkylalkylene, heterocyclyl, heterocyclylalkylene, aryl, arylalkylene, heteroaryl and heteroarylalkylene is optionally substituted with one or more substituents independently selected from D, F, Cl, $N_3$, CN, OH, SH, $NH_2$, alkyl, alkoxy, alkylthio and alkylamino;

each $R^8$ is independently H, D, alkyl, alkenyl, alkynyl, alkoxy or cycloalkyl, wherein each of alkenyl, alkynyl, alkoxy and cycloalkyl is optionally substituted with one or more substituents independently selected from D, F, Cl, $N_3$, CN, OH, SH, $NH_2$, alkyl, alkoxy, alkylthio, alkylamino, cycloalkyl, heterocyclyl, aryl and heteroaryl;

each $R^9$ is independently D, F, Cl, Br, I, $NO_2$, CN, $NH_2$, $-C(=O)R^{10}$, $-C(=O)OR^{10}$, $-C(=O)NR^{11}R^{11a}$, $-OC(=O)R^{10}$, $-N(R^{11})C(=O)R^{10}$, $-S(=O)R^{10}$, $-S(=O)_2R^{10}$, $-S(=O)_2OR^{10}$, $-S(=O)_2NR^{11}R^{11a}$, $-N(R^{11})S(=O)_2R^{10}$, alkyl, alkenyl, alkynyl, haloalkyl, alkoxy, alkylthio, alkylamino, cycloalkyl, cycloalkylalkylene, heterocyclyl, heterocyclylalkylene, aryl, arylalkylene, heteroaryl or heteroarylalkylene, wherein each of alkyl, alkenyl, alkynyl, haloalkyl, alkoxy, alkylthio, alkylamino, cycloalkyl, cycloalkylalkylene, heterocyclyl, heterocyclylalkylene, aryl, arylalkylene, heteroaryl and heteroarylalkylene is optionally substituted with one or more substituents independently selected from D, F, Cl, $N_3$, CN, OH, SH, $NH_2$, alkyl, alkoxy, alkylthio and alkylamino;

each $R^{10}$ is independently H, D, alkyl, alkenyl, alkynyl, haloalkyl, cycloalkyl, cycloalkylalkylene, heterocyclyl, heterocyclylalkylene, aryl, arylalkylene, heteroaryl or heteroarylalkylene, wherein each of alkyl, alkenyl, alkynyl, haloalkyl, cycloalkyl, cycloalkylalkylene, heterocyclyl, heterocyclylalkylene, aryl, arylalkylene, heteroaryl and heteroarylalkylene is optionally substituted with one or more substituents independently selected from D, F, Cl, $N_3$, CN, OH, SH, $NH_2$, alkyl, alkoxy, alkylthio and alkylamino;

each $R^{11}$ and $R^{11a}$ is independently H, D, alkyl, alkenyl, alkynyl, haloalkyl, cycloalkyl, cycloalkylalkylene, heterocyclyl, heterocyclylalkylene, aryl, arylalkylene, heteroaryl or heteroarylalkylene, or $R^{11}$ and $R^{11a}$, together with the nitrogen atom to which they are attached, form a heterocyclic ring, wherein each of alkyl, alkenyl, alkynyl, haloalkyl, cycloalkyl, cycloalkylalkylene, heterocyclyl, heterocyclylalkylene, aryl, arylalkylene, heteroaryl, heteroarylalkylene and heterocyclic ring is optionally substituted with one or more substituents independently selected from D, F, Cl, $N_3$, CN, OH, SH, $NH_2$, alkyl, alkoxy, alkylthio and alkylamino; and m is 3, 4, 5 or 6.

In one embodiment, the compounds disclosed herein have Formula (II) or a stereoisomer, a tautomer, an N-oxide, a solvate, a metabolite, a pharmaceutically acceptable salt or a prodrug thereof,

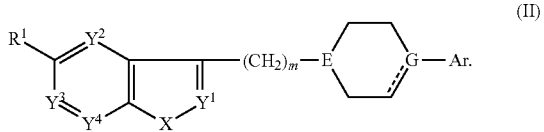
(II)

In another embodiment, each of $R^1$, $R^2$, $R^3$ and $R^4$ is independently H, D, F, Cl, $NO_2$, CN, $-OR^{10}$, $-SR^{10}$, $-NR^{11}R^{11a}$, $-C(=O)R^{10}$, $-C(=O)OR^{10}$, $-C(=O)NR^{11}R^{11a}$, $-OC(=O)R^{10}$, $-S(=O)R^{10}$, $-S(=O)_2R^{10}$, $-S(=O)_2OR^{10}$, $-S(=O)_2NR^{11}R^{11a}$, $-N(R^{11})C(=O)R^{10}$, $-N(R^{11})S(=O)_2R^{10}$, $C_1$-$C_6$ alkyl, $C_2$-$C_6$ alkenyl, $C_2$-$C_6$ alkynyl, $C_1$-$C_6$ haloalkyl, $C_3$-$C_{10}$ cycloalkyl, ($C_3$-$C_{10}$ cycloalkyl)-($C_1$-$C_6$ alkylene)-, $C_2$-$C_{10}$ heterocyclyl, ($C_2$-$C_{10}$ heterocyclyl)-($C_1$-$C_6$ alkylene)-, $C_6$-$C_{10}$ aryl, ($C_6$-$C_{10}$ aryl)-($C_1$-$C_6$ alkylene)-, $C_1$-$C_9$ heteroaryl or ($C_1$-$C_9$ heteroaryl)-($C_1$-$C_6$ alkylene)-, wherein each of $C_1$-$C_6$ alkyl, $C_2$-$C_6$ alkenyl, $C_2$-$C_6$ alkynyl, $C_1$-$C_6$ haloalkyl, $C_3$-$C_{10}$ cycloalkyl, ($C_3$-$C_{10}$ cycloalkyl)-($C_1$-$C_6$ alkylene)-, $C_2$-$C_{10}$ heterocyclyl, ($C_2$-$C_{10}$ heterocyclyl)-($C_1$-$C_6$ alkylene)-, $C_6$-$C_{10}$ aryl, ($C_6$-$C_{10}$ aryl)-($C_1$-$C_6$ alkylene)-, $C_1$-$C_9$ heteroaryl and ($C_1$-$C_9$ heteroaryl)-($C_1$-$C_6$ alkylene)- is optionally substituted with one or more substituents independently selected from D, F, Cl, $N_3$, CN, OH, SH, $NH_2$, $C_1$-$C_6$ alkyl, $C_1$-$C_6$ alkoxy, $C_1$-$C_6$ alkylthio and $C_1$-$C_6$ alkylamino.

In another embodiment, each of $R^1$, $R^2$, $R^3$ and $R^4$ is independently H, D, F, Cl, $NO_2$, CN, $-OR^{10}$, $-SR^{10}$, $-NR^{11}R^{11a}$, $C_1$-$C_4$ alkyl, $C_1$-$C_4$ haloalkyl, $C_3$-$C_8$ cycloalkyl, ($C_3$-$C_8$ cycloalkyl)-($C_1$-$C_4$ alkylene)-, $C_2$-$C_7$ heterocyclyl, ($C_2$-$C_7$ heterocyclyl)-($C_1$-$C_4$ alkylene)-, phenyl, (phenyl)-($C_1$-$C_4$ alkylene)-, $C_1$-$C_5$ heteroaryl or ($C_1$-$C_5$ heteroaryl)-($C_1$-$C_4$ alkylene)-, wherein each of $C_1$-$C_4$ alkyl, $C_1$-$C_4$ haloalkyl, $C_3$-$C_8$ cycloalkyl, ($C_3$-$C_8$ cycloalkyl)-($C_1$-$C_4$ alkylene)-, $C_2$-$C_7$ heterocyclyl, ($C_2$-$C_7$ heterocyclyl)-($C_1$-$C_4$ alkylene)-, phenyl, (phenyl)-($C_1$-$C_4$ alkylene)-, $C_1$-$C_5$ heteroaryl and ($C_1$-$C_5$ heteroaryl)-($C_1$-$C_4$ alkylene)- is optionally substituted with one or more substituents independently selected from D, F, Cl, $N_3$, CN, OH, SH, $NH_2$, $C_1$-$C_4$ alkyl, $C_1$-$C_4$ alkoxy, $C_1$-$C_4$ alkylthio and $C_1$-$C_4$ alkylamino.

In another embodiment, each $R^5$, $R^6$ and $R^7$ is independently H, D, F, Cl, $NO_2$, CN, $NH_2$, $-C(=O)R^{10}$, $-C(=O)OR^{10}$, $-C(=O)NR^{11}R^{11a}$, $-(C_1$-$C_6$ alkylene)-C(=O)NR^{11}R^{11a}$, $-OC(=O)R^{10}$, $-N(R^{11})C(=O)R^{10}$, $-S(=O)R^{10}$, $-S(=O)_2R^{10}$, $-S(=O)_2OR^{10}$, $-S(=O)_2NR^{11}R^{11a}$, $-N(R^{11})S(=O)_2R^{10}$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ alkylthio, $C_1$-$C_6$ alkylamino, $C_3$-$C_{10}$ cycloalkyl, ($C_3$-$C_{10}$ cycloalkyl)-($C_1$-$C_6$ alkylene)-, $C_2$-$C_{10}$ heterocyclyl, ($C_2$-$C_{10}$ heterocyclyl)-($C_1$-$C_6$ alkylene)-, $C_6$-$C_{10}$ aryl, ($C_6$-$C_{10}$ aryl)-($C_1$-$C_6$ alkylene)-, $C_1$-$C_9$ heteroaryl or ($C_1$-$C_9$ heteroaryl)-($C_1$-$C_6$ alkylene)-, with the proviso that at least one of $R^5$, $R^6$ and $R^7$ is not H, wherein each of $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ alkylthio, $C_1$-$C_6$ alkylamino, $C_3$-$C_{10}$ cycloalkyl, ($C_3$-$C_{10}$ cycloalkyl)-($C_1$-$C_6$ alkylene)-, $C_2$-$C_{10}$ heterocyclyl, ($C_2$-$C_{10}$ heterocyclyl)-($C_1$-$C_6$ alkylene)-, $C_6$-$C_{10}$ aryl, ($C_6$-$C_{10}$ aryl)-($C_1$-$C_6$ alkylene)-, $C_1$-$C_9$ heteroaryl and ($C_1$-$C_9$ heteroaryl)-($C_1$-$C_6$ alkylene)- is optionally substituted with one or more substituents independently selected from D, F, Cl, $N_3$, CN, OH, SH, $NH_2$, $C_1$-$C_6$ alkyl, $C_1$-$C_6$ alkoxy, $C_1$-$C_6$ alkylthio and $C_1$-$C_6$ alkylamino.

In another embodiment, each $R^5$, $R^6$ and $R^7$ is independently H, D, F, Cl, $NO_2$, CN, $NH_2$, $-C(=O)R^{10}$, $-C(=O)OR^{10}$, $-C(=O)NR^{11}R^{11a}$, $-(C_1$-$C_4$ alkylene)-C(=O)NR^{11}R^{11a}$, $-OC(=O)R^{10}$, $-N(R^{11})C(=O)R^{10}$, $-S(=O)R^{10}$, $-S(=O)_2R^{10}$, $-S(=O)_2OR^{10}$, $-S(=O)_2NR^{11}R^{11a}$, $-N(R^{11})S(=O)_2R^{10}$, $C_1$-$C_4$ alkyl, $C_1$-$C_4$ haloalkyl, $C_1$-$C_4$ alkoxy, $C_1$-$C_4$ alkylthio or $C_1$-$C_4$ alkylamino, with the proviso that at least one of $R^5$, $R^6$ and $R^7$ is not H, wherein each of $C_1$-$C_4$ alkyl, $C_1$-$C_4$ haloalkyl, $C_1$-$C_4$ alkoxy, $C_1$-$C_4$ alkylthio and $C_1$-$C_4$ alkylamino is optionally substituted with one or more substituents independently selected from D, F, Cl, $N_3$, CN, OH, SH, $NH_2$, $C_1$-$C_4$ alkyl, $C_1$-$C_4$ alkoxy, $C_1$-$C_4$ alkylthio and $C_1$-$C_4$ alkylamino.

In another embodiment, each $R^8$ is independently H, D, $C_1$-$C_6$ alkyl, $C_2$-$C_6$ alkenyl, $C_2$-$C_6$ alkynyl, $C_1$-$C_6$ alkoxy or $C_3$-$C_{10}$ cycloalkyl, wherein each of $C_2$-$C_6$ alkenyl, $C_2$-$C_6$ alkynyl, $C_1$-$C_6$ alkoxy and $C_3$-$C_{10}$ cycloalkyl is optionally substituted with one or more substituents independently selected from D, F, Cl, $N_3$, CN, OH, SH, $NH_2$, $C_1$-$C_6$ alkyl, $C_1$-$C_6$ alkoxy, $C_1$-$C_6$ alkylthio, $C_1$-$C_6$ alkylamino, $C_3$-$C_{10}$ cycloalkyl, $C_2$-$C_{10}$ heterocyclyl, $C_6$-$C_{10}$ aryl and $C_1$-$C_9$ heteroaryl.

In another embodiment, each $R^8$ is independently H, D, $C_1$-$C_4$ alkyl, $C_1$-$C_4$ alkoxy or $C_3$-$C_8$ cycloalkyl, wherein each of $C_1$-$C_4$ alkoxy and $C_3$-$C_8$ cycloalkyl is optionally substituted with one or more substituents independently selected from D, F, Cl, $N_3$, CN, OH, SH, $NH_2$, $C_1$-$C_4$ alkyl, $C_1$-$C_4$ alkoxy, $C_1$-$C_4$ alkylthio and $C_1$-$C_4$ alkylamino.

In another embodiment, each $R^9$ is independently D, F, Cl, $NO_2$, CN, $NH_2$, $-C(=O)R^{10}$, $-C(=O)OR^{10}$, $-C(=O)NR^{11}R^{11a}$, $-OC(=O)R^{10}$, $-N(R^{11})C(=O)R^{10}$, $-S(=O)R^{10}$, $-S(=O)_2R^{10}$, $-S(=O)_2OR^{10}$, $-S(=O)_2NR^{11}R^{11a}$, $-N(R^{11})S(=O)_2R^{10}$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ alkylthio, $C_1$-$C_6$ alkylamino, $C_3$-$C_{10}$ cycloalkyl, ($C_3$-$C_{10}$ cycloalkyl)-($C_1$-$C_6$ alkylene)-, $C_2$-$C_{10}$ heterocyclyl, ($C_2$-$C_{10}$ heterocyclyl)-($C_1$-$C_6$ alkylene)-, $C_6$-$C_{10}$ aryl, ($C_6$-$C_{10}$ aryl)-($C_1$-$C_6$ alkylene)-, $C_1$-$C_9$ heteroaryl or ($C_1$-$C_9$ heteroaryl)-($C_1$-$C_6$ alkylene)-, wherein each of $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ alkylthio, $C_1$-$C_6$ alkylamino, $C_3$-$C_{10}$ cycloalkyl, ($C_3$-$C_{10}$ cycloalkyl)-($C_1$-$C_6$ alkylene)-, $C_2$-$C_{10}$ heterocyclyl, ($C_2$-$C_{10}$ heterocyclyl)-($C_1$-$C_6$ alkylene)-, $C_6$-$C_{10}$ aryl, ($C_6$-$C_{10}$ aryl)-($C_1$-$C_6$ alkylene)-, $C_1$-$C_9$ heteroaryl and ($C_1$-$C_9$ heteroaryl)-($C_1$-$C_6$ alkylene)- is optionally substituted with one or more substituents independently selected from D, F, Cl, $N_3$, CN, OH, SH, $NH_2$, $C_1$-$C_6$ alkyl, $C_1$-$C_6$ alkoxy, $C_1$-$C_6$ alkylthio and $C_1$-$C_6$ alkylamino.

In another embodiment, each $R^9$ is independently D, F, Cl, $NO_2$, CN, $NH_2$, $-C(=O)R^{10}$, $-C(=O)OR^{10}$, $-C(=O)NR^{11}R^{11a}$, $-OC(=O)R^{10}$, $-N(R^{11})C(=O)R^{10}$, $-S(=O)R^{10}$, $-S(=O)_2R^{10}$, $-S(=O)_2OR^{10}$, $-S(=O)_2NR^{11}R^{11a}$, $-N(R^{11})S(=O)_2R^{10}$, $C_1$-$C_4$ alkyl, $C_1$-$C_4$ haloalkyl, $C_1$-$C_4$ alkoxy, $C_1$-$C_4$ alkylthio or $C_1$-$C_4$ alkylamino, wherein each of $C_1$-$C_4$ alkyl, $C_1$-$C_4$ haloalkyl, $C_1$-$C_4$ alkoxy, $C_1$-$C_4$ alkylthio and $C_1$-$C_4$ alkylamino is optionally substituted with one or more substituents independently selected from D, F, Cl, $N_3$, CN, OH, SH, $NH_2$, $C_1$-$C_4$ alkyl, $C_1$-$C_4$ alkoxy, $C_1$-$C_4$ alkylthio and $C_1$-$C_4$ alkylamino.

In another embodiment, each $R^{10}$ is independently H, D, $C_1$-$C_6$ alkyl, $C_1$-$C_6$ haloalkyl or $C_3$-$C_{10}$ cycloalkyl, wherein each of $C_1$-$C_6$ alkyl, $C_1$-$C_6$ haloalkyl and $C_3$-$C_{10}$ cycloalkyl is optionally substituted with one or more substituents independently selected from D, F, Cl, $N_3$, CN, OH, SH, $NH_2$, $C_1$-$C_6$ alkyl, $C_1$-$C_6$ alkoxy, $C_1$-$C_6$ alkylthio and $C_1$-$C_6$ alkylamino; and each $R^{11}$ and $R^{11a}$ is independently H, D, $C_1$-$C_6$ alkyl, $C_1$-$C_6$ haloalkyl or $C_3$-$C_{10}$ cycloalkyl, or $R^{11}$ and $R^{11a}$, together with the nitrogen atom to which they are attached, form a $C_2$-$C_{10}$ heterocyclic ring, wherein each of $C_1$-$C_6$ alkyl, $C_1$-$C_6$ haloalkyl, $C_3$-$C_{10}$ cycloalkyl and $C_2$-$C_{10}$ heterocyclic ring is optionally substituted with one or more substituents independently selected from D, F, Cl, $N_3$, CN, OH, SH, $NH_2$, $C_1$-$C_6$ alkyl, $C_1$-$C_6$ alkoxy, $C_1$-$C_6$ alkylthio and $C_1$-$C_6$ alkylamino.

In another embodiment, the compounds disclosed herein have Formula (III):

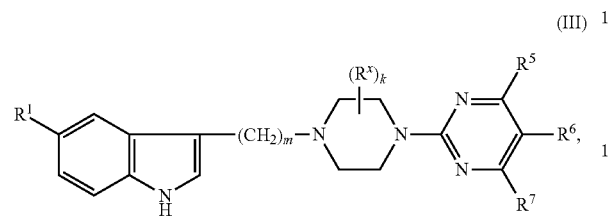

(III)

wherein
each $R^x$ is independently D, Cl, Me, —$CF_3$, —OMe, OH or $NH_2$;
k is 0, 1, 2, 3 or 4;
$R^1$ is H, D, F, Cl, CN, —$OR^{10}$, —$NR^{11}R^{11a}$, $C_1$-$C_4$ alkyl, $C_1$-$C_4$ haloalkyl, $C_3$-$C_8$ cycloalkyl, $C_2$-$C_7$ heterocyclyl, phenyl or $C_1$-$C_5$ heteroaryl, wherein each of $C_1$-$C_4$ alkyl, $C_1$-$C_4$ haloalkyl, $C_3$-$C_8$ cycloalkyl, $C_2$-$C_7$ heterocyclyl, phenyl and $C_1$-$C_5$ heteroaryl is optionally substituted with one or more substituents independently selected from D, F, Cl, $N_3$, CN, OH, SH, $NH_2$, $C_1$-$C_4$ alkyl, $C_1$-$C_4$ alkoxy, $C_1$-$C_4$ alkylthio and $C_1$-$C_4$ alkylamino;
each of $R^5$, $R^6$ and $R^7$ is independently H, D, F, Cl, $NO_2$, CN, $NH_2$, —$C(=O)R^{10}$, —$C(=O)OR^{10}$, —$C(=O)NR^{11}R^{11a}$, —($C_1$-$C_4$ alkylene)-$C(=O)NR^{11}R^{11a}$, —$OC(=O)R^{10}$, $C_1$-$C_4$ alkyl, $C_1$-$C_4$ haloalkyl, $C_1$-$C_4$ alkoxy, $C_1$-$C_4$ alkylthio or $C_1$-$C_4$ alkylamino, with the proviso that at least one of $R^5$, $R^6$ and $R^7$ is not H, wherein each of $C_1$-$C_4$ alkyl, $C_1$-$C_4$ haloalkyl, $C_1$-$C_4$ alkoxy, $C_1$-$C_4$ alkylthio and $C_1$-$C_4$ alkylamino is optionally substituted with one or more substituents independently selected from D, F, Cl, $N_3$, CN, OH, SH, $NH_2$, $C_1$-$C_4$ alkyl, $C_1$-$C_4$ alkoxy, $C_1$-$C_4$ alkylthio and $C_1$-$C_4$ alkylamino;
each $R^{10}$ is independently H, D, $C_1$-$C_4$ alkyl, $C_1$-$C_4$ haloalkyl or $C_3$-$C_8$ cycloalkyl;
each $R^{11}$ and $R^{11a}$ is independently H, D, $C_1$-$C_4$ alkyl, $C_1$-$C_4$ haloalkyl or $C_3$-$C_8$ cycloalkyl, or $R^{11}$ and $R^{11a}$, together with the nitrogen atom to which they are attached, form a $C_2$-$C_7$ heterocyclic ring; and
m is 3, 4, 5 or 6.

In another embodiment, the compounds disclosed herein have Formula (IV):

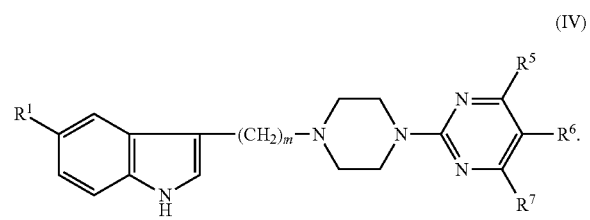

(IV)

In another embodiment, $R^1$ is H, D, F, Cl, CN, OH, $NH_2$, Me, Et, n-Pr, i-Pr, —$CF_3$, —OMe, —OEt, —O(i-Pr), —O(t-Bu) or —$NMe_2$.

In another embodiment, each of $R^5$, $R^6$ and $R^7$ is independently H, D, F, Cl, $NO_2$, CN, $NH_2$, —$C(=O)H$, —$C(=O)OH$, —$C(=O)OMe$, —$C(=O)NH_2$, —$CH_2$—$C(=O)NH_2$, —$C(=O)NMe_2$, Me, Et, n-Pr, i-Pr, —$CF_3$, —OMe, —OEt, —O(i-Pr), —O(t-Bu) or —$NMe_2$, with the proviso that at least one of $R^5$, $R^6$ and $R^7$ is not H.

In another embodiment, the compounds disclosed herein have Formula (V):

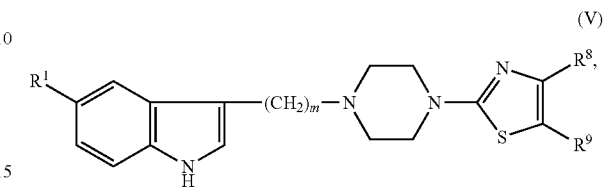

(V)

wherein
$R^1$ is H, D, F, Cl, CN, —$OR^{10}$, —$NR^{11}R^{11a}$, $C_1$-$C_4$ alkyl, $C_1$-$C_4$ haloalkyl, $C_3$-$C_8$ cycloalkyl, $C_2$-$C_7$ heterocyclyl, phenyl or $C_1$-$C_5$ heteroaryl, wherein each of $C_1$-$C_4$ alkyl, $C_1$-$C_4$ haloalkyl, $C_3$-$C_8$ cycloalkyl, $C_2$-$C_7$ heterocyclyl, phenyl and $C_1$-$C_5$ heteroaryl is optionally substituted with one or more substituents independently selected from D, F, Cl, $N_3$, CN, OH, SH, $NH_2$, $C_1$-$C_4$ alkyl, $C_1$-$C_4$ alkoxy, $C_1$-$C_4$ alkylthio and $C_1$-$C_4$ alkylamino;
$R^8$ is H, D, $C_1$-$C_4$ alkyl or $C_1$-$C_4$ alkoxy;
$R^9$ is D, F, Cl, $NO_2$, CN, $NH_2$, —$C(=O)R^{10}$, —$C(=O)OR^{10}$, —$C(=O)NR^{11}R^{11a}$, —$OC(=O)R^{10}$, $C_1$-$C_4$ alkyl, $C_1$-$C_4$ haloalkyl, $C_1$-$C_4$ alkoxy, $C_1$-$C_4$ alkylthio or $C_1$-$C_4$ alkylamino, wherein each of $C_1$-$C_4$ alkyl, $C_1$-$C_4$ haloalkyl, $C_1$-$C_4$ alkoxy, $C_1$-$C_4$ alkylthio and $C_1$-$C_4$ alkylamino is optionally substituted with one or more substituents independently selected from D, F, Cl, $N_3$, CN, OH, SH, $NH_2$, $C_1$-$C_4$ alkyl, $C_1$-$C_4$ alkoxy, $C_1$-$C_4$ alkylthio and $C_1$-$C_4$ alkylamino;
each $R^{10}$ is independently H, D, $C_1$-$C_4$ alkyl, $C_1$-$C_4$ haloalkyl or $C_3$-$C_8$ cycloalkyl;
each $R^{11}$ and $R^{11a}$ is independently H, D, $C_1$-$C_4$ alkyl, $C_1$-$C_4$ haloalkyl or $C_3$-$C_8$ cycloalkyl, or $R^{11}$ and $R^{11a}$, together with the nitrogen atom to which they are attached, form a $C_2$-$C_7$ heterocyclic ring; and
m is 3, 4, 5 or 6.

In another embodiment, $R^1$ is H, D, F, Cl, CN, OH, $NH_2$, Me, —$CF_3$, —OMe or —$NMe_2$.

In another embodiment, $R^8$ is H, D, Me, Et, i-Pr, t-Bu or —OMe.

In another embodiment, $R^9$ is D, F, Cl, $NO_2$, CN, $NH_2$, —$C(=O)H$, —$C(=O)OH$, —$C(=O)OMe$, —$C(=O)OEt$, —$C(=O)NH_2$, —$C(=O)NMe_2$, Me, Et, —$CF_3$ or —OMe.

In another aspect, provided herein is a pharmaceutical composition containing the compound disclosed herein.

In one embodiment, the pharmaceutical composition disclosed herein further comprises a pharmaceutically acceptable excipient, carrier, adjuvant or a combination thereof.

In another embodiment, the pharmaceutical composition disclosed herein further comprises at least one therapeutic agent for central nervous system dysfunction, wherein the therapeutic agent for central nervous system dysfunction is an antidepressant, an antianxiety agent, a lithium agent of mood stabilizer, an atypical antipsychotic agent, an antiepileptic agent, an anti-Parkinson agent, a selective serotonin reuptake inhibitor, a 5-$HT_{1A}$ receptor agonist, a central nervous system stimulant, a nicotine antagonist or a combination thereof.

In another embodiment, the therapeutic agent is amitriptyline, desipramine, mirtazapine, bupropion, reboxetine, fluoxetine, trazodone, sertraline, duloxetine, fluvoxamine, milnacipran, levomilnacipran, desvenlafaxine, vilazodone, venlafaxine, dapoxetine, nefazodone, femoxetine, clomipramine, citalopram, escitalopram, paroxetine, lithium carbonate, buspirone, olanzapine, quetiapine, risperidone, ziprasidone, aripiprazole, perospirone, clozapine, modafinil, mecamylamine, cabergoline, adamantane, imipramine, pramipexole, thyroxine, dextromethorphan, quinidine, naltrexone, samidorphan, buprenorphine, melatonin, alprazolam, pipamperone, vestipitant, chlordiazepoxide, perphenazine or a combination thereof.

In another aspect, provided herein is use of the compound or the pharmaceutical composition disclosed herein in the manufacture of a medicament for preventing, treating or lessening the severity of a central nervous system dysfunction in a mammal, including a human being.

In another aspect, provided herein is a method of preventing, treating or lessening the severity of a central nervous system dysfunction in a mammal comprising administrating a therapeutically effective amount of the compound or the pharmaceutical composition disclosed herein to the mammal, including a human being.

In another aspect, provided herein is the compound or the pharmaceutical composition disclosed herein for use in preventing, treating or lessening the severity of a central nervous system dysfunction in a mammal, including a human being.

In one embodiment, the central nervous system dysfunction is depression, anxiety, mania, schizophrenia, bipolar disorder, sleep disorder, obsessive compulsive disorder, panic disorder, post-traumatic stress disorder, movement disorder, sexual dysfunction, musculoskeletal pain disorder, cognitive disorder, memory disorder, Parkinson's disease, Huntington's disease, phobia, substance abuse or addiction, drug addiction withdrawal symptom or premenstrual tension syndrome.

In another aspect, provided herein is use of the compound or the pharmaceutical composition disclosed herein in the manufacture of a medicament for selectively inhibiting serotonin reuptake.

In another aspect, provided herein is a method of selectively inhibiting serotonin reuptake with the compound or the pharmaceutical composition disclosed herein.

In another aspect, provided herein is the compound or the pharmaceutical composition disclosed herein for use in selectively inhibiting serotonin reuptake.

In another aspect, provided herein are methods for preparation, separation and purification of the compounds represented by Formula (I), (II), (III), (IV) or (V).

Biological test results indicate that the compounds provided herein can be used as preferred selective serotonin reuptake inhibitors and/or 5-$HT_{1A}$ receptor agonists.

Any embodiment disclosed herein can be combined with other embodiments as long as they are not contradictory to one another, even though the embodiments are described under different aspects of the invention. In addition, any technical feature in one embodiment can be applied to the corresponding technical feature in other embodiment as long as they are not contradictory to one another, even though the embodiments are described under different aspects of the invention.

The foregoing merely summarizes certain aspects disclosed herein and is not intended to be limiting in nature. These aspects and other aspects and embodiments are described more fully below.

DETAILED DESCRIPTION OF THE INVENTION

Definitions and General Terminology

All the documents cited herein are incorporated by reference in their entireties, and if the meanings expressed in the documents are different from those in the invention, the expressions in the invention will control. In addition, the terms and phases used in the invention have the general meanings recognized by a person skilled in the art. Even so, the invention still tries to expound and explain the terms and phases as detailed as possible. If the terms and phases mentioned herein are not consistent with the well-known meanings, the meanings expressed in the invention will control. Regardless of whether the terms discussed appear alone or in combination, the definitions described herein are applicable.

For purposes disclosed herein, the chemical elements are identified in accordance with the Periodic Table of the Elements, CAS version, and *the Handbook of Chemistry and Physics*, $75^{th}$ Ed. 1994. Additionally, general principles of organic chemistry are described in "*Organic Chemistry*", Thomas Sorrell, University Science Books, Sausalito: 1999, and "*March's Advanced Organic Chemistry*" by Michael B. Smith and Jerry March, John Wiley & Sons, New York: 2007, all of which are incorporated herein by reference in their entireties.

The grammatical articles "one", "a", "an" and "the", as used herein, are intended to include "at least one" or "one or more" unless otherwise indicated herein or clearly contradicted by the context. Thus, the articles are used herein to refer to one or more than one (i.e., to at least one) of the grammatical objects of the article. By way of example, "a component" means one or more components, and thus, possibly, more than one component is contemplated and may be employed or used in an implementation of the described embodiments.

As described herein, compounds disclosed herein may optionally be substituted with one or more substituents, such as those illustrated above, or as exemplified by particular classes, subclasses and species of the invention.

The term "optional" or "optionally" refers to that a subsequently described event or circumstance may but need not occur, and that the description includes instances where the event or circumstance occurs and instances in which it does not. For example, "optional bond" means that the bond may or may not be present, and that the description includes single, double or triple bonds.

The term "substituted" refers to the replacement of one or more hydrogen groups in a given structure with the group of a specified substituent. Unless otherwise indicated, a substituted group may have a substituent at each substitutable position of the group. When more than one position in a given structure may be substituted with more than one substituent selected from a specified group, the substituent may be either the same or different at each position.

The term "unsubstituted" refers to a specified group without substituents.

The term "optionally substituted with . . . " is used interchangeably with the term "unsubstituted or substituted with . . . ", i.e., the given structure is unsubstituted or substituted with one or more substituents described herein. Some non-limiting examples of the substituents include D, F, Cl, $N_3$, —CN, —OH, —SH, —$NH_2$, alkyl, alkoxy, alkylthio, alkylamino, cycloalkyl, heterocyclyl, aryl, heteroaryl, and the like.

The term "unsaturated" refers to a moiety having one or more units of unsaturation.

The term "comprising" is an open-ended expression, which includes the content specified in the invention, but does not exclude other aspects.

At various places in the present specification, substituents of the compounds disclosed herein are disclosed in groups or in ranges. It is specifically intended that the invention includes each and every individual subcombination of the members of such groups and ranges. For example, the term "$C_1$-$C_6$ alkyl" is specifically intended to individually disclose methyl, ethyl, $C_3$ alkyl, $C_4$ alkyl, $C_5$ alkyl and $C_6$ alkyl.

At various places in the present specification, linking substituents are described. Where the structure clearly requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

The term "halogen" or "halo", which may be used interchangeably herein, refers to F, Cl, Br or I.

The term "alkyl" or "alkyl group" refers to a saturated linear or branched-chain monovalent hydrocarbon group of 1-20 carbon atoms, wherein the alkyl group is optionally substituted with one or more substituents described herein. Unless otherwise specified, the alkyl group contains 1-20 carbon atoms. In one embodiment, the alkyl group contains 1-12 carbon atoms. In another embodiment, the alkyl group contains 1-6 carbon atoms. In still another embodiment, the alkyl group contains 1-4 carbon atoms. In yet another embodiment, the alkyl group contains 1-3 carbon atoms. The alkyl group is optionally substituted with one or more substituents described herein.

Some non-limiting examples of the alkyl group include methyl (Me, —$CH_3$), ethyl (Et, —$CH_2CH_3$), n-propyl (n-Pr, —$CH_2CH_2CH_3$), isopropyl (i-Pr, —$CH(CH_3)_2$), n-butyl (n-Bu, —$CH_2CH_2CH_2CH_3$), isobutyl (i-Bu, —$CH_2CH(CH_3)_2$), sec-butyl (s-Bu, —$CH(CH_3)CH_2CH_3$), tert-butyl (t-Bu, —$C(CH_3)_3$), n-pentyl (—$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), n-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), n-heptyl, n-octyl, and the like.

The term "alkylene" refers to a saturated divalent hydrocarbon group derived from a straight or branched chain saturated hydrocarbon by the removal of two hydrogen atoms. Unless otherwise specified, the alkylene group contains 1-12 carbon atoms. In one embodiment, the alkylene group contains 1-6 carbon atoms. In another embodiment, the alkylene group contains 1-4 carbon atoms. In still another embodiment, the alkylene group contains 1-3 carbon atoms. In yet another embodiment, the alkylene group contains 1-2 carbon atoms. The alkylene group is exemplified by methylene (—$CH_2$—), ethylene (—$CH_2CH_2$—), isopropylene (—$CH(CH_3)CH_2$—), and the like. The alkylene group is optionally substituted with one or more substituents described herein.

The term "alkenyl" refers to a linear or branched chain monovalent hydrocarbon group of 2-12 carbon atoms with at least one site of unsaturation, i.e., a carbon-carbon, $sp^2$ double bond, wherein the alkenyl group is optionally substituted with one or more substituents described herein, and includes groups having "cis" and "trans" orientations, or alternatively, "E" and "Z" orientations. In one embodiment, the alkenyl group contains 2-8 carbon atoms. In another embodiment, the alkenyl group contains 2-6 carbon atoms. In still another embodiment, the alkenyl group contains 2-4 carbon atoms. Some non-limiting examples of the alkenyl group include ethenyl or vinyl (—CH=$CH_2$), allyl (—$CH_2$CH=$CH_2$), and the like. The alkenyl group is optionally substituted with one or more substituents described herein.

The term "alkynyl" refers to a linear or branched-chain monovalent hydrocarbon group of 2-12 carbon atoms with at least one site of unsaturation, i.e., a carbon-carbon, sp triple bond, wherein the alkynyl group is optionally substituted with one or more substituents described herein. In one embodiment, the alkynyl group contains 2-8 carbon atoms. In another embodiment, the alkynyl group contains 2-6 carbon atoms. In still another embodiment, the alkynyl group contains 2-4 carbon atoms. Some non-limiting examples of the alkynyl group include ethynyl (—C≡CH), propargyl (—$CH_2$C≡CH), 1-propynyl (—C≡C—$CH_3$), and the like. The alkynyl group is optionally substituted with one or more substituents described herein.

The term "alkoxy" refers to an alkyl group, as previously defined, attached to the parent molecular moiety through an oxygen atom, wherein the alkyl group is as defined herein. Unless otherwise specified, the alkoxy group contains 1-12 carbon atoms. In one embodiment, the alkoxy group contains 1-6 carbon atoms. In another embodiment, the alkoxy group contains 1-4 carbon atoms. In still another embodiment, the alkoxy group contains 1-3 carbon atoms. The alkoxy group is optionally substituted with one or more substituents described herein.

Some non-limiting examples of the alkoxy group include methoxy (MeO, —$OCH_3$), ethoxy (EtO, —$OCH_2CH_3$), 1-propoxy (n-PrO, n-propoxy, —$OCH_2CH_2CH_3$), 2-propoxy (i-PrO, i-propoxy, —$OCH(CH_3)_2$), 1-butoxy (n-BuO, n-butoxy, $OCH_2CH_2CH_2CH_3$), 2-methyl-1-propoxy (i-BuO, i-butoxy, —$OCH_2CH(CH_3)_2$), 2-butoxy (s-BuO, s-butoxy, —$OCH(CH_3)CH_2CH_3$), 2-methyl-2-propoxy (t-BuO, t-butoxy, —$OC(CH_3)_3$), 1-pentoxy (n-pentoxy, —$OCH_2CH_2CH_2CH_2CH_3$), 2-pentoxy (—$OCH(CH_3)CH_2CH_2CH_3$), 3-pentoxy (—$OCH(CH_2CH_3)_2$), 2-methyl-2-butoxy (—$OC(CH_3)_2CH_2CH_3$), 3-methyl-2-butoxy (—$OCH(CH_3)CH(CH_3)_2$), 3-methyl-1-butoxy (—$OCH_2CH_2CH(CH_3)_2$), 2-methyl-1-butoxy (—$OCH_2CH(CH_3)CH_2CH_3$), and the like.

The term "haloalkyl" or "haloalkoxy" refers to an alkyl or alkoxy group substituted with one or more halogen atoms, wherein the alkyl group and alkoxy group are as defined herein. Some non-limiting examples of the haloalkyl group and the haloalkoxy group include chloromethyl, trifluoromethyl, trifluoroethyl, trifluoromethoxy, and the like. The haloalkyl group or the haloalkoxy group is optionally substituted with one or more substituents described herein.

The term "alkylamino" embraces "N-alkylamino" and "N,N-dialkylamino", wherein the amino group is independently substituted with one or two alkyl groups, respectively. In one embodiment, the alkylamino group is lower alkylamino group having one or two alkyl groups of 1 to 6 carbon atoms, which are attached to a nitrogen atom. In another embodiment, the alkylamino group is lower alkylamino group having 1 to 4 carbon atoms. Some non-limiting examples of the alkylamino group include mono-alkylamino or dialkylamino such as N-methylamino, N-ethylamino, N,N-dimethylamino, N,N-diethylamino, and the like. The alkylamino group is optionally substituted with one or more substituents described herein.

The term "alkylthio" refers to a group containing a linear or branched alkyl group of 1 to 10 carbon atoms attached to a divalent sulfur atom. In one embodiment, the alkylthio group is lower alkylthio group having 1 to 4 carbon atoms. Some non-limiting examples of the alkylthio group include methylthio ($CH_3S$—). The alkylthio group is optionally substituted with one or more substituents described herein.

The term "cycloalkyl" refers to a saturated ring having 3 to 12 carbon atoms as a monocyclic, bicyclic or tricyclic ring system, wherein the bicyclic or tricyclic ring system may include fused ring, bridged ring and spiro ring. In one embodiment, the cycloalkyl group contains 3-10 carbon atoms. In another embodiment, the cycloalkyl group contains 3-8 carbon atoms. In still another embodiment, the cycloalkyl group contains 3-6 carbon atoms. The cycloalkyl group is optionally substituted with one or more substituents described herein.

The term "cycloalkylalkylene" refers to an alkyl group substituted with one or more cycloalkyl groups, wherein the alkyl group and cycloalkyl group are as defined herein. In one embodiment, the cycloalkylalkylene group is lower cycloalkylalkylene group in which the cycloalkyl group is attached to an alkyl group having 1 to 6 carbon atoms. In another embodiment, the cycloalkyl group is attached to an alkyl group having 1 to 4 carbon atoms. In still another embodiment, the cycloalkyl group is attached to an alkyl group having 1 to 3 carbon atoms. The cycloalkylalkylene group is optionally substituted with one or more substituents described herein.

The term "heteroatom" refers to one or more of oxygen (O), sulfur (S), nitrogen (N), phosphorus (P) or silicon (Si), including any oxidized form of nitrogen (N), sulfur (S) or phosphorus (P); the quaternized form of any basic nitrogen; or a substitutable nitrogen of a heterocyclic ring, for example N (as in 3,4-dihydro-2H-pyrrolyl), NH (as in pyrrolidinyl) or NR (as in N-substituted pyrrolidinyl).

The term "heterocycle", "heterocyclyl" or "heterocyclic" as used interchangeably herein refers to a monocyclic, bicyclic or tricyclic ring system in which one or more ring members are an independently selected heteroatom as defined herein and that is completely saturated or that contains one or more units of unsaturation, but which is not aromatic, having a single point of attachment to the rest of the molecule. In some embodiments, the "heterocycle", "heterocyclyl" or "heterocyclic" group is a monocycle having 3 to 8 ring members (e.g., 2 to 6 carbon atoms and 1 to 3 heteroatoms selected from N, O, P and S, wherein the S or P is optionally substituted with one or more oxo to provide the group SO or $SO_2$, or PO or $PO_2$, with the proviso that when the ring is a 3-membered ring, there is only one heteroatom) or a bicycle having 7 to 12 ring members (e.g., 4 to 9 carbon atoms and 1 to 3 heteroatoms selected from N, O, P and S, wherein the S or P is optionally substituted with one or more oxo to provide the group SO or $SO_2$, or PO or $PO_2$). The "heterocycle", "heterocyclyl" or "heterocyclic" group is optionally substituted with one or more substituents described herein.

The heterocyclyl may be a carbon radical or heteroatom radical. Some non-limiting examples of the heterocyclyl group include pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, epoxypropyl, azepanyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydrothienyl, pyrazolidinylimidazolinyl, imidazolidinyl, and 1,2,3,4-tetrahydroisoquinolinyl. Examples of the heterocyclyl group wherein two ring carbon atoms are substituted with oxo (=O) moieties are pyrimidindionyl and 1,1-dioxo-thiomorpholinyl.

The term "heterocyclylalkylene" refers to an alkyl group substituted with one or more heterocyclyl groups, wherein the alkyl group and heterocyclyl group are as defined herein. In one embodiment, the heterocyclylalkylene group is lower heterocyclylalkylene group in which the heterocyclyl group is attached to an alkyl group having 1 to 6 carbon atoms. In another embodiment, the heterocyclyl group is attached to an alkyl group having 1 to 4 carbon atoms. Some non-limiting examples of the heterocyclylalkylene group include 2-pyrrolidinoethyl, and the like. The heterocyclylalkylene group is optionally substituted with one or more substituents described herein.

The term "aryl" refers to monocyclic, bicyclic and tricyclic carbocyclic ring systems having a total of 6 to 14 ring members, preferably, 6 to 10 ring members, and more preferably 6 ring members, wherein at least one ring in the system is aromatic, and wherein each ring in the system contains 3 to 7 ring members. The aryl group is generally, but not necessarily bonded to the parent molecule through an aromatic ring of the aryl group. The term "aryl" may be used interchangeably with the term "aryl ring" or "aromatic ring". Some non-limiting examples of the aryl group include phenyl, naphthyl and anthracene. The aryl group is optionally substituted with one or more substituents described herein.

The term "arylalkylene" refers to an alkyl group substituted with one or more aryl groups, wherein the alkyl group and aryl group are as defined herein. In one embodiment, the arylalkylene group is lower arylalkylene group in which the aryl group is attached to an alkyl group having 1 to 6 carbon atoms. In another embodiment, the arylalkylene group is "phenylalkylene" containing alkyl groups of 1 to 4 carbon atoms. Some non-limiting examples of the arylalkylene group include benzyl, diphenylmethyl, phenylethyl, and the like. The arylalkylene group is optionally substituted with one or more substituents described herein.

The term "heteroaryl" refers to monocyclic, bicyclic and tricyclic ring systems having a total of 5 to 14 ring members, preferably, 5 to 10 ring members, and more preferably 5 to 6 ring members, wherein at least one ring in the system is aromatic, and at least one ring in the system contains one or more heteroatoms, and wherein each ring in the system contains 5 to 7 ring members. The heteroaryl group is generally, but not necessarily bonded to the parent molecule through an aromatic ring of the heteroaryl group. The term "heteroaryl" may be used interchangeably with the term "heteroaryl ring" or the term "heteroaromatic ring". The heteroaryl group is optionally substituted with one or more substituents described herein. In one embodiment, a 5-10 membered heteroaryl comprises 1, 2, 3 or 4 heteroatoms independently selected from O, S and N.

Some non-limiting examples of the heteroaryl group include the following monocycles: 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, pyrazinyl, 1,3,5-triazinyl, and the following bicycles: benzimidazolyl, benzofuryl, benzothiophenyl, indolyl (e.g., 2-indolyl), purinyl, quinolinyl (e.g., 2-quinolinyl, 3-quinolinyl, and 4-quinolinyl), isoquinolinyl (e.g., 1-isoquinolinyl, 3-isoquinolinyl, and 4-isoquinolinyl), imidazo[1,2-a]pyridyl, pyrazolo[1,5-a]pyridyl, pyrazolo[1,5-a]pyrimidyl, imidazo[1,2-b]pyridazinyl, [1,2,4]triazolo[4,3-b]pyridazinyl, [1,2,4]triazolo[1,5-a]pyrimidinyl, [1,2,4]triazolo[1,5-a]pyridyl, and the like.

The term "heteroarylalkylene" refers to an alkyl group substituted with one or more heteroaryl groups, wherein the alkyl group and heteroaryl group are as defined herein. In one embodiment, the heteroarylalkylene group is lower heteroarylalkylene groups in which the heteroaryl group is attached to an alkyl group having 1 to 6 carbon atoms. In another embodiment, the heteroaryl group is attached to an alkyl group having 1 to 4 carbon atoms. Some non-limiting examples of the heteroarylalkylene group include 2-pyridylmethyl, 3-furylethyl, and the like. The heteroarylalkylene group is optionally substituted with one or more substituents described herein.

The term "carbonyl", whether used alone or with other terms, refers to —(C=O)—.

The term "acyl" refers to —(C=O)—R.

The term "amido" refers to —NH(C=O)—R.

The term "carbamoyl" refers to —C(=O)NH$_2$.

The term "azido" refers to —N$_3$. The azido group can be attached to other groups, for example, to methyl to form methylazide (MeN$_3$), or to phenyl to form phenylazide (PhN$_3$).

As described herein, a bond drawn from a substituent to the center of one ring within a ring system represents substitution of the substituent at any substitutable position on the rings to which it is attached. For example, Figure a represents possible substitution in any of the position on the ring B.

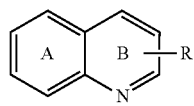

a

The term "spirocyclyl", "spirocyclic", "spiro bicyclyl" or "spiro bicyclic" as used interchangeably herein refers to a ring system wherein a ring originating from a particular annular carbon of another ring. For example, as depicted below in Figure c and Figure d, ring A and ring B share a carbon atom between the two saturated ring system, which terms as a "spirocyclyl" or "spiro bicyclyl". Each ring in the spiro bicyclyl can be either a carbocyclyl or a heterocyclyl. Some non-limiting examples of the spiro bicyclyl group include 4-oxaspiro[2.4]hept-6-yl, and (R)-4-azaspiro[2.4]hept-6-yl. The spiro bicyclyl group is optionally substituted with one or more substituents described herein.

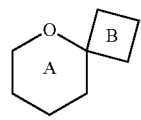

c

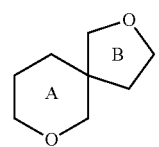

d

The term "fused bicyclic ring", "fused cyclic", "fused bicyclyl" or "fused cyclyl" as used interchangeably herein refers to a bridged ring system in which two rings share a common C—C bond. For example, as depicted below in Figure e, Figure f and Figure g, two five-membered rings (Figure e), two six-membered rings (Figure f), and a five-membered ring and a six-membered ring (Figure g) share a common C—C bond. Such a ring system may contain isolated or conjugated unsaturation, but not aromatic or heteroaromatic rings in its core structure (but may have aromatic substitution thereon). Each ring in the fused bicyclic ring system is independently carbocyclic ring or heterocyclic ring.

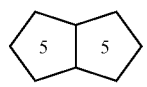

e

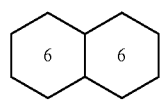

f

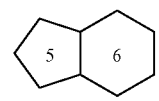

g

Some non-limiting examples of the fused bicyclyl group include hexahydrofuro[2,3-b]furan-3-yl, hexahydrofuro[3,2-b]furan-3-yl, octahydrocyclopenta[c]pyrrol-5-yl, octahydropentalen-2-yl, octahydro-1H-isoindol-5-yl, and the like. The fused bicyclyl group is optionally substituted with one or more substituents described herein.

The term "stereoisomer" refers to compounds which have identical chemical constitution, but differ with regard to the arrangement of the atoms or groups in space. Stereoisomers include enantiomers, diastereomers, conformers (rotamers), geometric (cis/trans) isomers, atropisomers, and the like.

The term "diastereoisomer" refers to a stereoisomer with two or more centers of chirality and whose molecules are not mirror images of one another. Diastereomers have different physical properties, e.g., melting points, boiling points, spectral properties or biological activities. Mixture of diastereomers may separate under high resolution analytical procedures such as electrophoresis and chromatography such as HPLC.

The term "enantiomer" refers to two stereoisomers of a compound which are non-superimposable mirror images of one another.

The term "racemate" or "racemic mixture" refers to an equimolar mixture of two enantiomeric species devoid of optical activity.

The term "chiral" refers to molecules which have the property of non-superimposability of the mirror image partner, while the term "achiral" refers to molecules which are superimposable on their mirror image partner.

Stereochemical definitions and conventions used herein generally follow Parker et al., McGraw-Hill Dictionary of Chemical Terms (1984) McGraw-Hill Book Company, New York; and Eliel et al., "Stereochemistry of Organic Compounds", John Wiley & Sons, Inc., New York, 1994.

Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. A specific stereoisomer may be referred to as an enantiomer, and a mixture of such isomers is called an enantiomeric mixture. A 50:50 mixture of enantiomers is referred to as a racemic mixture or a racemate, which may occur where there has been no stereoselection or stereospecificity in a chemical reaction or process.

Any asymmetric atom (e.g., carbon or the like) of the compound(s) disclosed herein can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration.

Depending on the choice of the starting materials and procedures, the compounds can be present in the form of one of the possible isomers or as mixtures thereof, such as racemates and diastereoisomer mixtures, depending on the number of asymmetric carbon atoms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration.

Any resulting mixtures of isomers can be separated on the basis of the physicochemical differences of the constituents, into the pure or substantially pure geometric isomers, enantiomers, diastereomers, for example, by chromatography and/or fractional crystallization.

Any resulting racemates of final products or intermediates can be resolved into the optical antipodes by methods known to those skilled in the art, e.g., by separation of the diastereomeric salts thereof. Racemic products can also be resolved by chiral chromatography, e.g., high performance liquid chromatography (HPLC) using a chiral adsorbent. Preferred enantiomers can also be prepared by asymmetric syntheses. See, for example, Jacques, et al., *Enantiomers, Racemates and Resolutions* (Wiley Interscience, New York, 1981); *Principles of Asymmetric Synthesis* ($2^{nd}$ Ed. Robert et al., Elsevier, Oxford, UK, 2012); Eliel et al., *Stereochemistry of Carbon Compounds* (McGraw-Hill, NY, 1962); and Wilen et al., *Tables of Resolving Agents and Optical Resolutions* p. 268 (E. L. Eliel, Ed., Univ. of Notre Dame Press, Notre Dame, Ind., 1972). *Chiral Separation Techniques: A Practical Approach* (Subramanian, G. Ed., Wiley-VCH Verlag GmbH & Co. KGaA, Weinheim, Germany, 2007).

The term "tautomer" or "tautomeric form" refers to structural isomers of different energies which are interconvertible via a low energy barrier. Where tautomerization is possible (e.g. in solution), a chemical equilibrium of tautomers can be reached. For example, proton tautomers (also known as prototropic tautomers) include interconversions via migration of a proton, such as keto-enol and imine-enamine isomerizations. Valence tautomers include interconversions by reorganization of some of the bonding electrons. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers. Unless otherwise stated, all tautomeric forms of the compounds disclosed herein are within the scope of the invention.

The term "pharmaceutically acceptable" refers to compounds, materials, compositions and/or dosage forms which are, within the scope of sound medical judgement, suitable for use in contact with the tissues of a subject without excessive toxicity, irritation, allergic response or other problem or complication commensurate with a reasonable benefit/risk ratio, and effective for their intended purpose.

Unless otherwise stated, structures depicted herein are also meant to include all isomeric (e.g., enantiomeric, diastereomeric, and geometric (or conformational)) forms of the structure, for example, the R and S configurations for each asymmetric center, (Z) and (E) double bond isomers, and (Z) and (E) conformational isomers. Therefore, single stereochemical isomers as well as enantiomeric, diastereomeric, or geometric (or conformational) mixtures of the present compounds are within the scope of the invention.

Unless otherwise stated, all tautomeric forms of the compounds disclosed herein are within the scope of the invention. Additionally, unless otherwise stated, structures depicted herein are also meant to include compounds that differ only in the presence of one or more isotopically enriched atoms.

The term "prodrug" refers to a compound that is transformed in vivo into a compound of Formula (I). Such a transformation can be affected, for example, by hydrolysis of the prodrug form in blood or enzymatic transformation of the prodrug form in blood or tissue to the parent form. Prodrugs of the compounds disclosed herein may be, for example, esters. Some common esters which have been utilized as prodrugs are phenyl esters, aliphatic ($C_1$-$C_{24}$) esters, acyloxymethyl esters, carbonates, carbamates and amino acid esters. For example, a compound disclosed herein that contains an OH group may be acylated at this position in its prodrug form. Other prodrug forms include phosphates, such as those phosphate compounds derived from the phosphonation of an OH group on the parent compound. A thorough discussion of prodrugs is provided in Higuchi et al., *Pro-drugs as Novel Delivery Systems*, Vol. 14, A.C.S. Symposium Series; Roche et al., ed., *Bioreversible Carriers in Drug Design*, American Pharmaceutical Association and Pergamon Press, 1987; Rautio et al, Prodrugs: Design and Clinical Applications, *Nature Reviews Drug Discovery*, 2008, 7, 255-270, and Hecker et al., Prodrugs of Phosphates and Phosphonates, *J Med. Chem.*, 2008, 51, 2328-2345, all of which are incorporated herein by reference in their entireties.

A "metabolite" is a product produced through metabolism in the body of a specified compound or salt thereof. The metabolite of a compound may be identified using routine techniques known in the art and their activities determined using tests such as those described herein. Such products may result for example from the oxidation, reduction, hydrolysis, amidation, deamidation, esterification, deesterification, enzymatic cleavage, and the like, of the administered compound. Accordingly, the invention includes metabolites of compounds disclosed herein, including metabolites produced by a process comprising contacting a compound disclosed herein with a mammal for a sufficient time period.

The term "pharmaceutically acceptable salt" refers to a salt which is, within the scope of sound medical judgement, suitable for contacting tissues of human and lower animals without showing excessive toxicity, irritation and anaphylactic response, and is commensurate to reasonable effect/risk ratio. The pharmaceutically acceptable salt is well known in the art. For example, S. M. Berge, et al., describes pharmaceutically acceptable salts in detail in *J. Pharmaceutical Sciences*, 1977, 66: 1.

Some non-limiting examples of pharmaceutically acceptable salts derived from nontoxic acids include acetate, adipate, alginate, citrate, ascorbate, aspartate, benzoate, benzenesulfonate, bisulfate, borate, butyrate, camphorate, camphorsulfonate, cyclopentanepropionate, digluconate, dodecylsulfate, ethanesulfonate, formate, glucoheptonate, glycerophosphate, gluconate, hemisulfate, heptanoate, hexanoate, fumarate, hydrochloride, hydrobromide, hydroiodide, 2-hydroxy-ethanesulfonate, lactobionate, lactate, maleate, laurate, laurylsulfate, malate, malonate, methanesulfonate, nicotinate, 2-napsylate, oxalate, nitrate, oleate, palmitate, pamoate, pectinate, persulfate, 3-phenylpropionate, picrate, pivalate, propionate, succinate, tartrate, stearate, thiocyanate, phosphate, glutamate, bicarbonate, p-tosylate, undecanoate, valerate salts, and the like. Pharmaceutically acceptable salts derived from appropriate bases include alkali metal, alkaline earth metal, ammonium and $N^+(C_1$-$C_4$ alkyl$)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further examples of the pharmaceutically acceptable salt include, when appropriate, nontoxic ammonium, quaternary ammonium, and amine cations formed using counterions such as halide, hydroxide, carboxylate, sulfate, phosphate, nitrate, $C_1$-$C_8$ sulfonate and aryl sulfonate.

A "solvate" refers to an association or complex of one or more solvent molecules and a compound disclosed herein. Some non-limiting examples of solvents that form the solvates include water, isopropanol, ethanol, methanol, DMSO, ethyl acetate, acetic acid, ethanolamine or mixtures thereof.

The term "hydrate" can be used when said solvent is water. In some embodiments, one solvent molecule is associated with one molecule of the compounds disclosed herein, such as a hydrate. In other embodiments, more than one solvent molecule may be associated with one molecule of the compounds disclosed herein, such as a dihydrate. In still other embodiments, less than one solvent molecule may be associated with one molecule of the compounds disclosed herein, such as a hemihydrate. Furthermore, all the solvates of the invention retain the biological effectiveness of the non-hydrate form of the compounds disclosed herein.

The term "protecting group" or "PG" refers to a substituent that is commonly employed to block or protect a particular functionality while reacting with other functional groups on the compound. For example, an "amino-protecting group" is a substituent attached to an amino group that blocks or protects the amino functionality in the compound. Examples of suitable amino-protecting groups include acetyl, trifluoroacetyl, benzoyl, ethoxycarbonyl, t-butoxycarbonyl (BOC), benzyloxycarbonyl (CBZ), 9-fluorenylmethylenoxycarbonyl (Fmoc) and benzyl. Similarly, a "hydroxy-protecting group" refers to a substituent of a hydroxy group that blocks or protects the hydroxy functionality. Examples of suitable hydroxy-protecting groups include trialkylsilyl, acetyl, benzoyl and benzyl. A "carboxy-protecting group" refers to a substituent of the carboxy group that blocks or protects the carboxy functionality. Examples of common carboxy-protecting groups include —$CH_2CH_2SO_2Ph$, cyanoethyl, 2-(trimethylsilyl)ethyl, 2-(trimethylsilyl)ethoxymethyl, 2-(p-toluenesulfonyl)ethyl, 2-(p-nitrophenylsulfonyl)ethyl, 2-(diphenylphosphino)ethyl, nitroethyl, and the like. For a general description of protecting groups and their use, see Greene et al., *Protective Groups in Organic Synthesis*, John Wiley & Sons, New York, 1991 and Kocienski et al., *Protecting Groups*, Thieme, Stuttgart, 2005.

The term "preventing" or "prevention" refers to a reduction in risk of acquiring a disease or disorder (i.e., causing at least one of the clinical symptoms of the disease not to develop in a subject that may be exposed to or predisposed to the disease but does not yet experience or display symptoms of the disease).

The term "therapeutically effective amount" refers to the amount of a compound that, when administered to a subject for treating a disease, is sufficient to effect such treatment for the disease. The "therapeutically effective amount" can vary depending on the compound, the disease and its severity, and the condition, age, weight, gender etc. of the subject to be treated.

"Treating" or "treatment" of a disease state includes: (i) preventing the disease state, i.e., causing the clinical symptoms of the disease state not to develop in a subject that may be exposed to or predisposed to the disease state, but does not yet experience or display symptoms of the disease state, (ii) inhibiting the disease state, i.e., arresting the development of the disease state or its clinical symptoms, or (iii) relieving the disease state, i.e., causing temporary or permanent regression of the disease state or its clinical symptoms.

DESCRIPTION OF COMPOUNDS OF THE INVENTION

Disclosed herein are heteroaryl compounds, pharmaceutically acceptable salts thereof, pharmaceutical formulations thereof and compositions thereof, which are acting as selective serotonin reuptake inhibitors and/or 5-$HT_{1A}$ receptor agonists and have potential therapeutic uses for the treatment of human central nervous system (CNS) dysfunction, such as depression, anxiety disorder or bipolar disorder.

In one aspect, provided herein are compounds having Formula (I) or a stereoisomer, a tautomer, an N-oxide, a solvate, a metabolite, a pharmaceutically acceptable salt or a prodrug thereof,

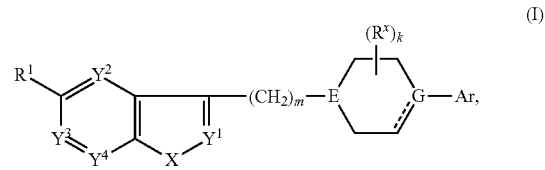

wherein
X is O, S or NH;
$Y^1$ is CH or N;
$Y^2$ is $CR^2$ or N;
$Y^3$ is $CR^3$ or N;
$Y^4$ is $CR^4$ or N;
E is N or CH;
===== is either a single bond or a double bond, provided that: (1) when ===== is a single bond, G is CH or N; or (2) when ===== is a double bond, G is C;
Ar is

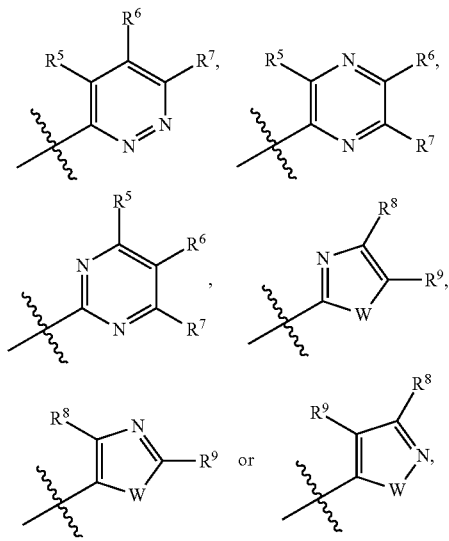

wherein each W is independently O, S or NH;

each $R^x$ is independently D, F, Cl, $C_1$-$C_6$ alkyl, $C_1$-$C_6$ haloalkyl, —$NR^{11}R^{11a}$, —$OR^{10}$, —($C_1$-$C_6$ alkylene)-$NR^{11}R^{11a}$, —($C_1$-$C_6$ alkylene)-$OR^{10}$, —C(=O)$R^{10}$, —C(=O)$OR^{10}$, —C(=O)$NR^{11}R^{11a}$ or —($C_1$-$C_6$ alkylene)-aryl, or two $R^x$ on two adjacent ring carbon atoms, together with the ring carbon atoms to which they are attached, form a $C_3$-$C_6$ carbocyclic or 3-6 membered heterocyclic ring;

k is 0, 1, 2, 3 or 4;

each of $R^1$, $R^2$, $R^3$ and $R^4$ is independently H, D, F, Cl, Br, I, $NO_2$, CN, —SCN, —$OR^{10}$, —$SR^{10}$, —$NR^{11}R^{11a}$, —C(=O)$R^{10}$, —C(=O)$OR^{10}$, —C(=O)$NR^{11}R^{11a}$, —OC(=O)$R^{10}$, —S(=O)$R^{10}$, —S(=O)$_2R^{10}$, —S(=O)$_2OR^{10}$, —S(=O)$_2NR^{11}R^{11a}$, —N($R^{11}$)C(=O)$R^{10}$, —N($R^{11}$)S(=O)$_2R^{10}$, alkyl, alkenyl, alkynyl, haloalkyl, cycloalkyl, cycloalkylalkylene, heterocyclyl, heterocyclylalkylene, aryl, arylalkylene, heteroaryl or heteroarylalkylene, wherein each of alkyl, alkenyl, alkynyl, haloalkyl, cycloalkyl, cycloalkylalkylene, heterocyclyl, heterocyclylalkylene, aryl, arylalkylene, heteroaryl and heteroarylalkylene is optionally substituted with one or more substituents independently selected from D, F, Cl, $N_3$, CN, OH, SH, $NH_2$, alkyl, alkoxy, alkylthio and alkylamino;

each $R^5$, $R^6$ and $R^7$ is independently H, D, F, Cl, Br, I, $NO_2$, CN, $NH_2$, —C(=O)$R^{10}$, —C(=O)$OR^{10}$, —C(=O)$NR^{11}R^{11a}$, -alkylene-C(=O)$NR^{11}R^{11a}$, —OC(=O)$R^{10}$, —N($R^{11}$)C(=O)$R^{10}$, —S(=O)$R^{10}$, —S(=O)$_2R^{10}$, —S(=O)$_2OR^{10}$, —S(=O)$_2NR^{11}R^{11a}$, —N($R^{11}$)S(=O)$_2R^{10}$, alkyl, alkenyl, alkynyl, haloalkyl, alkoxy, alkylthio, alkylamino, cycloalkyl, cycloalkylalkylene, heterocyclyl, heterocyclylalkylene, aryl, arylalkylene, heteroaryl or heteroarylalkylene, with the proviso that at least one of $R^5$, $R^6$ and $R^7$ is not H, wherein each of alkyl, alkenyl, alkynyl, haloalkyl, alkoxy, alkylthio, alkylamino, cycloalkyl, cycloalkylalkylene, heterocyclyl, heterocyclylalkylene, aryl, arylalkylene, heteroaryl and heteroarylalkylene is optionally substituted with one or more substituents independently selected from D, F, Cl, $N_3$, CN, OH, SH, $NH_2$, alkyl, alkoxy, alkylthio and alkylamino;

each $R^8$ is independently H, D, alkyl, alkenyl, alkynyl, alkoxy or cycloalkyl, wherein each of alkenyl, alkynyl, alkoxy and cycloalkyl is optionally substituted with one or more substituents independently selected from D, F, Cl, $N_3$, CN, OH, SH, $NH_2$, alkyl, alkoxy, alkylthio, alkylamino, cycloalkyl, heterocyclyl, aryl and heteroaryl;

each $R^9$ is independently D, F, Cl, Br, I, $NO_2$, CN, $NH_2$, —C(=O)$R^{10}$, —C(=O)$OR^{10}$, —C(=O)$NR^{11}R^{11a}$, —OC(=O)$R^{10}$, —N($R^{11}$)C(=O)$R^{10}$, —S(=O)$R^{10}$, —S(=O)$_2R^{10}$, —S(=O)$_2OR^{10}$, —S(=O)$_2NR^{11}R^{11a}$, —N($R^{11}$)S(=O)$_2R^{10}$, alkyl, alkenyl, alkynyl, haloalkyl, alkoxy, alkylthio, alkylamino, cycloalkyl, cycloalkylalkylene, heterocyclyl, heterocyclylalkylene, aryl, arylalkylene, heteroaryl or heteroarylalkylene, wherein each of alkyl, alkenyl, alkynyl, haloalkyl, alkoxy, alkylthio, alkylamino, cycloalkyl, cycloalkylalkylene, heterocyclyl, heterocyclylalkylene, aryl, arylalkylene, heteroaryl and heteroarylalkylene is optionally substituted with one or more substituents independently selected from D, F, Cl, $N_3$, CN, OH, SH, $NH_2$, alkyl, alkoxy, alkylthio and alkylamino;

each $R^{10}$ is independently H, D, alkyl, alkenyl, alkynyl, haloalkyl, cycloalkyl, cycloalkylalkylene, heterocyclyl, heterocyclylalkylene, aryl, arylalkylene, heteroaryl or heteroarylalkylene, wherein each of alkyl, alkenyl, alkynyl, haloalkyl, cycloalkyl, cycloalkylalkylene, heterocyclyl, heterocyclylalkylene, aryl, arylalkylene, heteroaryl and heteroarylalkylene is optionally substituted with one or more substituents independently selected from D, F, Cl, $N_3$, CN, OH, SH, $NH_2$, alkyl, alkoxy, alkylthio and alkylamino;

each $R^{11}$ and $R^{11a}$ is independently H, D, alkyl, alkenyl, alkynyl, haloalkyl, cycloalkyl, cycloalkylalkylene, heterocyclyl, heterocyclylalkylene, aryl, arylalkylene, heteroaryl or heteroarylalkylene, or $R^{11}$ and $R^{11a}$, together with the nitrogen atom to which they are attached, form a heterocyclic ring, wherein each of alkyl, alkenyl, alkynyl, haloalkyl, cycloalkyl, cycloalkylalkylene, heterocyclyl, heterocyclylalkylene, aryl, arylalkylene, heteroaryl, heteroarylalkylene and heterocyclic ring is optionally substituted with one or more substituents independently selected from D, F, Cl, $N_3$, CN, OH, SH, $NH_2$, alkyl, alkoxy, alkylthio and alkylamino; and m is 3, 4, 5 or 6.

In one embodiment, the compounds disclosed herein have Formula (II) or a stereoisomer, a tautomer, an N-oxide, a solvate, a metabolite, a pharmaceutically acceptable salt or a prodrug thereof,

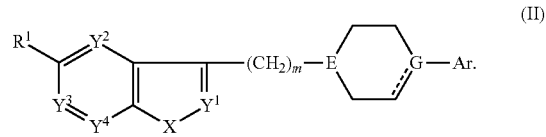

(II)

In another embodiment, each of $R^1$, $R^2$, $R^3$ and $R^4$ is independently H, D, F, Cl, $NO_2$, CN, —$OR^{10}$, —$SR^{10}$, —$NR^{11}R^{11a}$, —C(=O)$R^{10}$, —C(=O)$OR^{10}$, —C(=O)$NR^{11}R^{11a}$, —OC(=O)$R^{10}$, —S(=O)$R^{10}$, —S(=O)$_2R^{10}$, —S(=O)$_2OR^{10}$, —S(=O)$_2NR^{11}R^{11a}$, —N($R^{11}$)C(=O)

$R^{10}$, $-N(R^{11})S(=O)_2R^{10}$, $C_1$-$C_6$ alkyl, $C_2$-$C_6$ alkenyl, $C_2$-$C_6$ alkynyl, $C_1$-$C_6$ haloalkyl, $C_3$-$C_{10}$ cycloalkyl, ($C_3$-$C_{10}$ cycloalkyl)-($C_1$-$C_6$ alkylene)-, $C_2$-$C_{10}$ heterocyclyl, ($C_2$-$C_{10}$ heterocyclyl)-($C_1$-$C_6$ alkylene)-, $C_6$-$C_{10}$ aryl, ($C_6$-$C_{10}$ aryl)-($C_1$-$C_6$ alkylene)-, $C_1$-$C_9$ heteroaryl or ($C_1$-$C_9$ heteroaryl)-($C_1$-$C_6$ alkylene)-, wherein each of $C_1$-$C_6$ alkyl, $C_2$-$C_6$ alkenyl, $C_2$-$C_6$ alkynyl, $C_1$-$C_6$ haloalkyl, $C_3$-$C_{10}$ cycloalkyl, ($C_3$-$C_{10}$ cycloalkyl)-($C_1$-$C_6$ alkylene)-, $C_2$-$C_{10}$ heterocyclyl, ($C_2$-$C_{10}$ heterocyclyl)-($C_1$-$C_6$ alkylene)-, $C_6$-$C_{10}$ aryl, ($C_6$-$C_{10}$ aryl)-($C_1$-$C_6$ alkylene)-, $C_1$-$C_9$ heteroaryl and ($C_1$-$C_9$ heteroaryl)-($C_1$-$C_6$ alkylene)- is optionally substituted with one or more substituents independently selected from D, F, Cl, $N_3$, CN, OH, SH, $NH_2$, $C_1$-$C_6$ alkyl, $C_1$-$C_6$ alkoxy, $C_1$-$C_6$ alkylthio and $C_1$-$C_6$ alkylamino.

In another embodiment, each of $R^1$, $R^2$, $R^3$ and $R^4$ is independently H, D, F, Cl, $NO_2$, CN, $-OR^{10}$, $-SR^{10}$, $-NR^{11}R^{11a}$, $C_1$-$C_4$ alkyl, $C_1$-$C_4$ haloalkyl, $C_3$-$C_8$ cycloalkyl, ($C_3$-$C_8$ cycloalkyl)-($C_1$-$C_4$ alkylene)-, $C_2$-$C_7$ heterocyclyl, ($C_2$-$C_7$ heterocyclyl)-($C_1$-$C_4$ alkylene)-, phenyl, (phenyl)-($C_1$-$C_4$ alkylene)-, $C_1$-$C_5$ heteroaryl or ($C_1$-$C_5$ heteroaryl)-($C_1$-$C_4$ alkylene)-, wherein each of $C_1$-$C_4$ alkyl, $C_1$-$C_4$ haloalkyl, $C_3$-$C_8$ cycloalkyl, ($C_3$-$C_8$ cycloalkyl)-($C_1$-$C_4$ alkylene)-, $C_2$-$C_7$ heterocyclyl, ($C_2$-$C_7$ heterocyclyl)-($C_1$-$C_4$ alkylene)-, phenyl, (phenyl)-($C_1$-$C_4$ alkylene)-, $C_1$-$C_5$ heteroaryl and ($C_1$-$C_5$ heteroaryl)-($C_1$-$C_4$ alkylene)- is optionally substituted with one or more substituents independently selected from D, F, Cl, $N_3$, CN, OH, SH, $NH_2$, $C_1$-$C_4$ alkyl, $C_1$-$C_4$ alkoxy, $C_1$-$C_4$ alkylthio and $C_1$-$C_4$ alkylamino.

In another embodiment, each $R^5$, $R^6$ and $R^7$ is independently H, D, F, Cl, $NO_2$, CN, $NH_2$, $-C(=O)R^{10}$, $-C(=O)OR^{10}$, $-C(=O)NR^{11}R^{11a}$, $-(C_1$-$C_6$ alkylene)-C(=O)NR^{11}R^{11a}$, $-OC(=O)R^{10}$, $-N(R^{11})C(=O)R^{10}$, $-S(=O)R^{10}$, $-S(=O)_2R^{10}$, $-S(=O)_2OR^{10}$, $-S(=O)_2NR^{11}R^{11a}$, $-N(R^{11})S(=O)_2R^{10}$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ alkylthio, $C_1$-$C_6$ alkylamino, $C_3$-$C_{10}$ cycloalkyl, ($C_3$-$C_{10}$ cycloalkyl)-($C_1$-$C_6$ alkylene)-, $C_2$-$C_{10}$ heterocyclyl, ($C_2$-$C_{10}$ heterocyclyl)-($C_1$-$C_6$ alkylene)-, $C_6$-$C_{10}$ aryl, ($C_6$-$C_{10}$ aryl)-($C_1$-$C_6$ alkylene)-, $C_1$-$C_9$ heteroaryl or ($C_1$-$C_9$ heteroaryl)-($C_1$-$C_6$ alkylene)-, with the proviso that at least one of $R^5$, $R^6$ and $R^7$ is not H, wherein each of $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ alkylthio, $C_1$-$C_6$ alkylamino, $C_3$-$C_{10}$ cycloalkyl, ($C_3$-$C_{10}$ cycloalkyl)-($C_1$-$C_6$ alkylene)-, $C_2$-$C_{10}$ heterocyclyl, ($C_2$-$C_{10}$ heterocyclyl)-($C_1$-$C_6$ alkylene)-, $C_6$-$C_{10}$ aryl, ($C_6$-$C_{10}$ aryl)-($C_1$-$C_6$ alkylene)-, $C_1$-$C_9$ heteroaryl and ($C_1$-$C_9$ heteroaryl)-($C_1$-$C_6$ alkylene)- is optionally substituted with one or more substituents independently selected from D, F, Cl, $N_3$, CN, OH, SH, $NH_2$, $C_1$-$C_6$ alkyl, $C_1$-$C_6$ alkoxy, $C_1$-$C_6$ alkylthio and $C_1$-$C_6$ alkylamino.

In another embodiment, each $R^5$, $R^6$ and $R^7$ is independently H, D, F, Cl, $NO_2$, CN, $NH_2$, $-C(=O)R^{10}$, $-C(=O)OR^{10}$, $-C(=O)NR^{11}R^{11a}$, $-(C_1$-$C_4$ alkylene)-C(=O)NR^{11}R^{11a}$, $-OC(=O)R^{10}$, $-N(R^{11})C(=O)R^{10}$, $-S(=O)R^{10}$, $-S(=O)_2R^{10}$, $-S(=O)_2OR^{10}$, $-S(=O)_2NR^{11}R^{11a}$, $-N(R^{11})S(=O)_2R^{10}$, $C_1$-$C_4$ alkyl, $C_1$-$C_4$ haloalkyl, $C_1$-$C_4$ alkoxy, $C_1$-$C_4$ alkylthio or $C_1$-$C_4$ alkylamino, with the proviso that at least one of $R^5$, $R^6$ and $R^7$ is not H, wherein each of $C_1$-$C_4$ alkyl, $C_1$-$C_4$ haloalkyl, $C_1$-$C_4$ alkoxy, $C_1$-$C_4$ alkylthio and $C_1$-$C_4$ alkylamino is optionally substituted with one or more substituents independently selected from D, F, Cl, $N_3$, CN, OH, SH, $NH_2$, $C_1$-$C_4$ alkyl, $C_1$-$C_4$ alkoxy, $C_1$-$C_4$ alkylthio and $C_1$-$C_4$ alkylamino.

In another embodiment, each $R^8$ is independently H, D, $C_1$-$C_6$ alkyl, $C_2$-$C_6$ alkenyl, $C_2$-$C_6$ alkynyl, $C_1$-$C_6$ alkoxy or $C_3$-$C_{10}$ cycloalkyl, wherein each of $C_2$-$C_6$ alkenyl, $C_2$-$C_6$ alkynyl, $C_1$-$C_6$ alkoxy and $C_3$-$C_{10}$ cycloalkyl is optionally substituted with one or more substituents independently selected from D, F, Cl, $N_3$, CN, OH, SH, $NH_2$, $C_1$-$C_6$ alkyl, $C_1$-$C_6$ alkoxy, $C_1$-$C_6$ alkylthio, $C_1$-$C_6$ alkylamino, $C_3$-$C_{10}$ cycloalkyl, $C_2$-$C_{10}$ heterocyclyl, $C_6$-$C_{10}$ aryl and $C_1$-$C_9$ heteroaryl.

In another embodiment, each $R^8$ is independently H, D, $C_1$-$C_4$ alkyl, $C_1$-$C_4$ alkoxy or $C_3$-$C_8$ cycloalkyl, wherein each of $C_1$-$C_4$ alkoxy and $C_3$-$C_8$ cycloalkyl is optionally substituted with one or more substituents independently selected from D, F, Cl, $N_3$, CN, OH, SH, $NH_2$, $C_1$-$C_4$ alkyl, $C_1$-$C_4$ alkoxy, $C_1$-$C_4$ alkylthio and $C_1$-$C_4$ alkylamino.

In another embodiment, each $R^9$ is independently D, F, Cl, $NO_2$, CN, $NH_2$, $-C(=O)R^{10}$, $-C(=O)OR^{10}$, $-C(=O)NR^{11}R^{11a}$, $-OC(=O)R^{10}$, $-N(R^{11})C(=O)R^{10}$, $-S(=O)R^{10}$, $-S(=O)_2R^{10}$, $-S(=O)_2OR^{10}$, $-S(=O)_2NR^{11}R^{11a}$, $-N(R^{11})S(=O)_2R^{10}$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ alkylthio, $C_1$-$C_6$ alkylamino, $C_3$-$C_{10}$ cycloalkyl, ($C_3$-$C_{10}$ cycloalkyl)-($C_1$-$C_6$ alkylene)-, $C_2$-$C_{10}$ heterocyclyl, ($C_2$-$C_{10}$ heterocyclyl)-($C_1$-$C_6$ alkylene)-, $C_6$-$C_{10}$ aryl, ($C_6$-$C_{10}$ aryl)-($C_1$-$C_6$ alkylene)-, $C_1$-$C_9$ heteroaryl or ($C_1$-$C_9$ heteroaryl)-($C_1$-$C_6$ alkylene)-, wherein each of $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ alkylthio, $C_1$-$C_6$ alkylamino, $C_3$-$C_{10}$ cycloalkyl, ($C_3$-$C_{10}$ cycloalkyl)-($C_1$-$C_6$ alkylene)-, $C_2$-$C_{10}$ heterocyclyl, ($C_2$-$C_{10}$ heterocyclyl)-($C_1$-$C_6$ alkylene)-, $C_6$-$C_{10}$ aryl, ($C_6$-$C_{10}$ aryl)-($C_1$-$C_6$ alkylene)-, $C_1$-$C_9$ heteroaryl and ($C_1$-$C_9$ heteroaryl)-($C_1$-$C_6$ alkylene)- is optionally substituted with one or more substituents independently selected from D, F, Cl, $N_3$, CN, OH, SH, $NH_2$, $C_1$-$C_6$ alkyl, $C_1$-$C_6$ alkoxy, $C_1$-$C_6$ alkylthio and $C_1$-$C_6$ alkylamino.

In another embodiment, each $R^9$ is independently D, F, Cl, $NO_2$, CN, $NH_2$, $-C(=O)R^{10}$, $-C(=O)OR^{10}$, $-C(=O)NR^{11}R^{11a}$, $-OC(=O)R^{10}$, $-N(R^{11})C(=O)R^{10}$, $-S(=O)R^{10}$, $-S(=O)_2R^{10}$, $-S(=O)_2OR^{10}$, $-S(=O)_2NR^{11}R^{11a}$, $-N(R^{11})S(=O)_2R^{10}$, $C_1$-$C_4$ alkyl, $C_1$-$C_4$ haloalkyl, $C_1$-$C_4$ alkoxy, $C_1$-$C_4$ alkylthio or $C_1$-$C_4$ alkylamino, wherein each of $C_1$-$C_4$ alkyl, $C_1$-$C_4$ haloalkyl, $C_1$-$C_4$ alkoxy, $C_1$-$C_4$ alkylthio and $C_1$-$C_4$ alkylamino is optionally substituted with one or more substituents independently selected from D, F, Cl, $N_3$, CN, OH, SH, $NH_2$, $C_1$-$C_4$ alkyl, $C_1$-$C_4$ alkoxy, $C_1$-$C_4$ alkylthio and $C_1$-$C_4$ alkylamino.

In another embodiment, each $R^{10}$ is independently H, D, $C_1$-$C_6$ alkyl, $C_1$-$C_6$ haloalkyl or $C_3$-$C_{10}$ cycloalkyl, wherein each of $C_1$-$C_6$ alkyl, $C_1$-$C_6$ haloalkyl and $C_3$-$C_{10}$ cycloalkyl is optionally substituted with one or more substituents independently selected from D, F, Cl, $N_3$, CN, OH, SH, $NH_2$, $C_1$-$C_6$ alkyl, $C_1$-$C_6$ alkoxy, $C_1$-$C_6$ alkylthio and $C_1$-$C_6$ alkylamino; and each $R^{11}$ and $R^{11a}$ is independently H, D, $C_1$-$C_6$ alkyl, $C_1$-$C_6$ haloalkyl or $C_3$-$C_{10}$ cycloalkyl, or $R^{11}$ and $R^{11a}$, together with the nitrogen atom to which they are attached, form a $C_2$-$C_{10}$ heterocyclic ring, wherein each of $C_1$-$C_6$ alkyl, $C_1$-$C_6$ haloalkyl, $C_3$-$C_{10}$ cycloalkyl and $C_2$-$C_{10}$ heterocyclic ring is optionally substituted with one or more substituents independently selected from D, F, Cl, $N_3$, CN, OH, SH, $NH_2$, $C_1$-$C_6$ alkyl, $C_1$-$C_6$ alkoxy, $C_1$-$C_6$ alkylthio and $C_1$-$C_6$ alkylamino.

In another embodiment, the compounds disclosed herein have Formula (III):

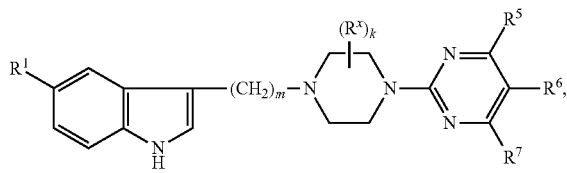

(III)

wherein each $R^x$ is independently D, Cl, Me, —$CF_3$, —OMe, OH or $NH_2$;

k is 0, 1, 2, 3 or 4;

$R^1$ is H, D, F, Cl, CN, —$OR^{10}$, —$NR^{11}R^{11a}$, $C_1$-$C_4$ alkyl, $C_1$-$C_4$ haloalkyl, $C_3$-$C_8$ cycloalkyl, $C_2$-$C_7$ heterocyclyl, phenyl or $C_1$-$C_5$ heteroaryl, wherein each of $C_1$-$C_4$ alkyl, $C_1$-$C_4$ haloalkyl, $C_3$-$C_8$ cycloalkyl, $C_2$-$C_7$ heterocyclyl, phenyl and $C_1$-$C_5$ heteroaryl is optionally substituted with one or more substituents independently selected from D, F, Cl, $N_3$, CN, OH, SH, $NH_2$, $C_1$-$C_4$ alkyl, $C_1$-$C_4$ alkoxy, $C_1$-$C_4$ alkylthio and $C_1$-$C_4$ alkylamino;

each of $R^5$, $R^6$ and $R^7$ is independently H, D, F, Cl, $NO_2$, CN, $NH_2$, —C(=O)$R^{10}$, —C(=O)$OR^{10}$, —C(=O)$NR^{11}R^{11a}$, —($C_1$-$C_4$ alkylene)-C(=O)$NR^{11}R^{11a}$, —OC(=O)$R^{10}$, $C_1$-$C_4$ alkyl, $C_1$-$C_4$ haloalkyl, $C_1$-$C_4$ alkoxy, $C_1$-$C_4$ alkylthio or $C_1$-$C_4$ alkylamino, with the proviso that at least one of $R^5$, $R^6$ and $R^7$ is not H, wherein each of $C_1$-$C_4$ alkyl, $C_1$-$C_4$ haloalkyl, $C_1$-$C_4$ alkoxy, $C_1$-$C_4$ alkylthio and $C_1$-$C_4$ alkylamino is optionally substituted with one or more substituents independently selected from D, F, Cl, $N_3$, CN, OH, SH, $NH_2$, $C_1$-$C_4$ alkyl, $C_1$-$C_4$ alkoxy, $C_1$-$C_4$ alkylthio and $C_1$-$C_4$ alkylamino;

each $R^{10}$ is independently H, D, $C_1$-$C_4$ alkyl, $C_1$-$C_4$ haloalkyl or $C_3$-$C_8$ cycloalkyl;

each $R^{11}$ and $R^{11a}$ is independently H, D, $C_1$-$C_4$ alkyl, $C_1$-$C_4$ haloalkyl or $C_3$-$C_8$ cycloalkyl, or $R^{11}$ and $R^{11a}$, together with the nitrogen atom to which they are attached, form a $C_2$-$C_7$ heterocyclic ring; and m is 3, 4, 5 or 6.

In another embodiment, the compounds disclosed herein have Formula (IV):

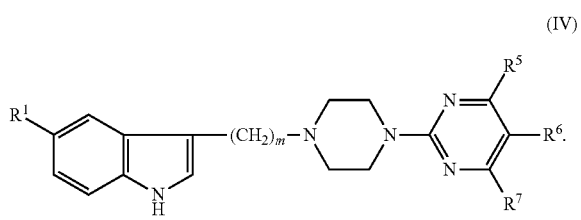

(IV)

In another embodiment, $R^1$ is H, D, F, Cl, CN, OH, $NH_2$, Me, Et, n-Pr, i-Pr, —$CF_3$, —OMe, —OEt, —O(i-Pr), —O(t-Bu) or —$NMe_2$.

In another embodiment, each of $R^5$, $R^6$ and $R^7$ is independently H, D, F, Cl, $NO_2$, CN, $NH_2$, —C(=O)H, —C(=O)OH, —C(=O)OMe, —C(=O)$NH_2$, —$CH_2$—C(=O)$NH_2$, —C(=O)$NMe_2$, Me, Et, n-Pr, i-Pr, —$CF_3$, —OMe, —OEt, —O(i-Pr), —O(t-Bu) or —$NMe_2$, with the proviso that at least one of $R^5$, $R^6$ and $R^7$ is not H.

In another embodiment, the compounds disclosed herein have Formula (V):

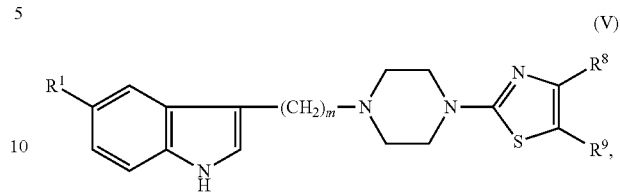

(V)

wherein $R^1$ is H, D, F, Cl, CN, —$OR^{10}$, —$NR^{11}R^{11a}$, $C_1$-$C_4$ alkyl, $C_1$-$C_4$ haloalkyl, $C_3$-$C_8$ cycloalkyl, $C_2$-$C_7$ heterocyclyl, phenyl or $C_1$-$C_5$ heteroaryl, wherein each of $C_1$-$C_4$ alkyl, $C_1$-$C_4$ haloalkyl, $C_3$-$C_8$ cycloalkyl, $C_2$-$C_7$ heterocyclyl, phenyl and $C_1$-$C_5$ heteroaryl is optionally substituted with one or more substituents independently selected from D, F, Cl, $N_3$, CN, OH, SH, $NH_2$, $C_1$-$C_4$ alkyl, $C_1$-$C_4$ alkoxy, $C_1$-$C_4$ alkylthio and $C_1$-$C_4$ alkylamino;

$R^8$ is H, D, $C_1$-$C_4$ alkyl or $C_1$-$C_4$ alkoxy;

$R^9$ is D, F, Cl, $NO_2$, CN, $NH_2$, —C(=O)$R^{10}$, —C(=O)$OR^{10}$, —C(=O)$NR^{11}R^{11a}$, —OC(=O)$R^{10}$, $C_1$-$C_4$ alkyl, $C_1$-$C_4$ haloalkyl, $C_1$-$C_4$ alkoxy, $C_1$-$C_4$ alkylthio or $C_1$-$C_4$ alkylamino, wherein each of $C_1$-$C_4$ alkyl, $C_1$-$C_4$ haloalkyl, $C_1$-$C_4$ alkoxy, $C_1$-$C_4$ alkylthio and $C_1$-$C_4$ alkylamino is optionally substituted with one or more substituents independently selected from D, F, Cl, $N_3$, CN, OH, SH, $NH_2$, $C_1$-$C_4$ alkyl, $C_1$-$C_4$ alkoxy, $C_1$-$C_4$ alkylthio and $C_1$-$C_4$ alkylamino;

each $R^{10}$ is independently H, D, $C_1$-$C_4$ alkyl, $C_1$-$C_4$ haloalkyl or $C_3$-$C_8$ cycloalkyl;

each $R^{11}$ and $R^{11a}$ is independently H, D, $C_1$-$C_4$ alkyl, $C_1$-$C_4$ haloalkyl or $C_3$-$C_8$ cycloalkyl, or $R^{11}$ and $R^{11a}$, together with the nitrogen atom to which they are attached, form a $C_2$-$C_7$ heterocyclic ring; and m is 3, 4, 5 or 6.

In another embodiment, $R^1$ is H, D, F, Cl, CN, OH, $NH_2$, Me, —$CF_3$, —OMe or —$NMe_2$.

In another embodiment, $R^8$ is H, D, Me, Et, i-Pr, t-Bu or —OMe.

In another embodiment, $R^9$ is D, F, Cl, $NO_2$, CN, $NH_2$, —C(=O)H, —C(=O)OH, —C(=O)OMe, —C(=O)OEt, —C(=O)$NH_2$, —C(=O)$NMe_2$, Me, Et, —$CF_3$ or —OMe.

In another embodiment, the compounds disclosed herein have one of the following structures:

(01)

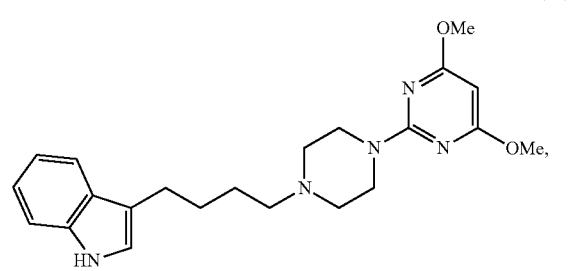

(02)
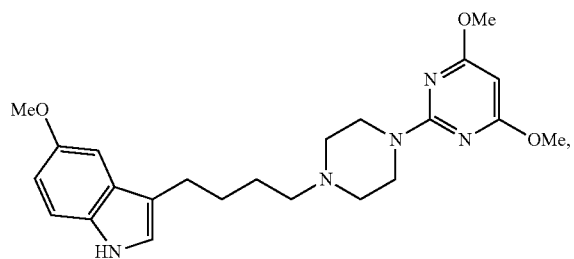
(03)
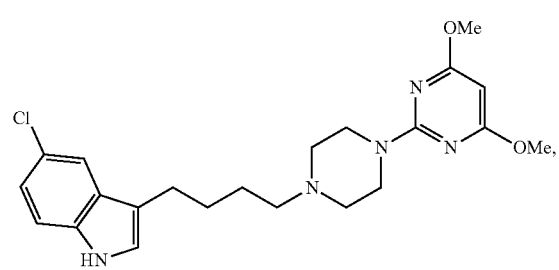
(04)
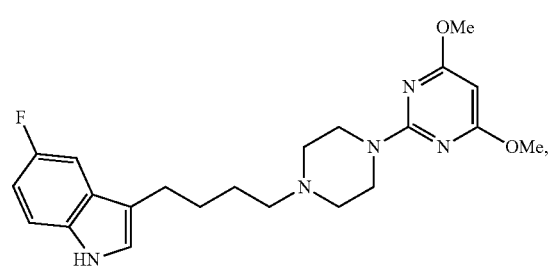
(05)
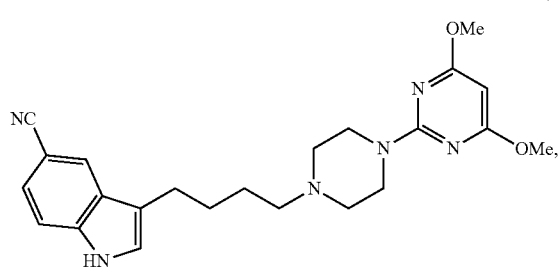
(06)
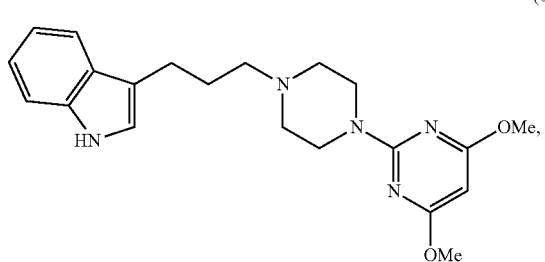
(07)
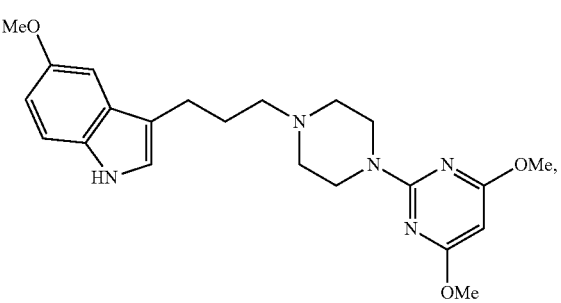
(08)
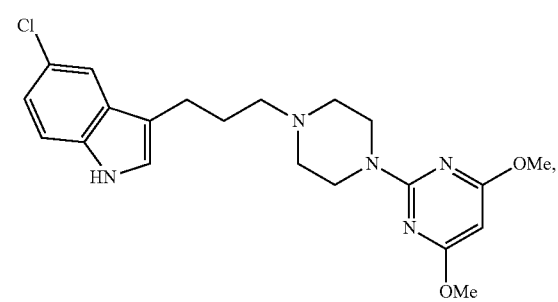
(09)
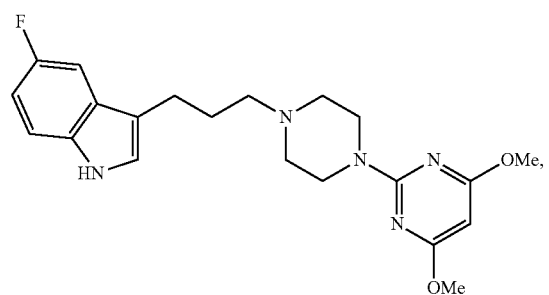
(10)
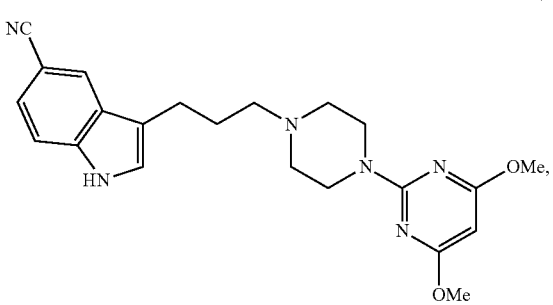
(11)
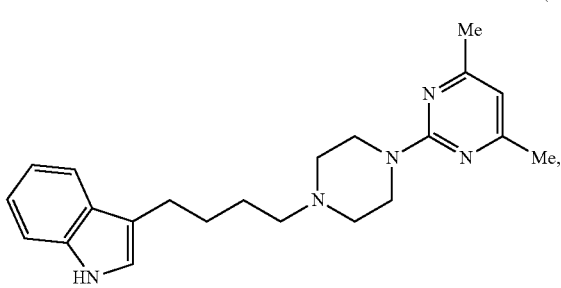

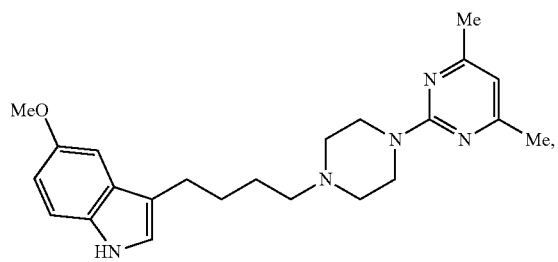
(12)
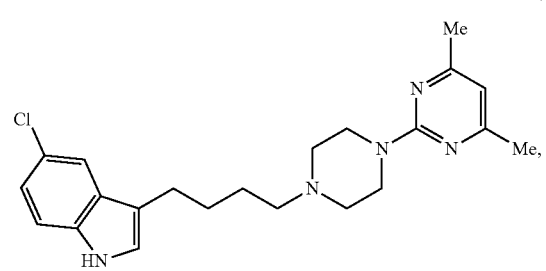
(13)
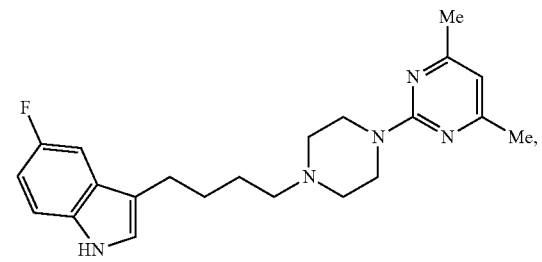
(14)
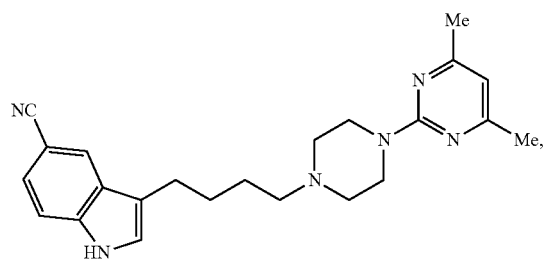
(15)
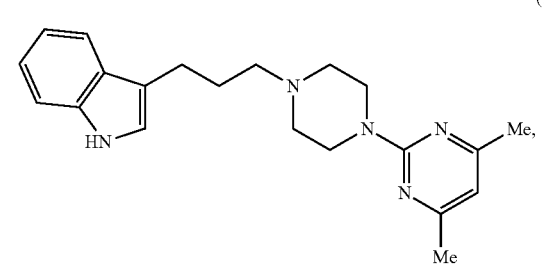
(16)
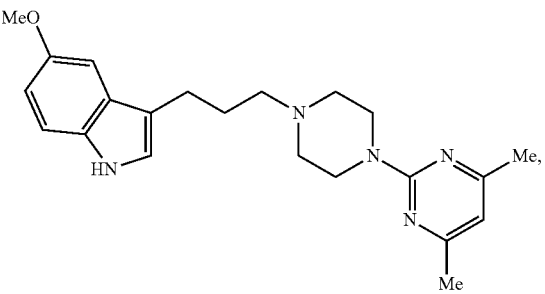
(17)
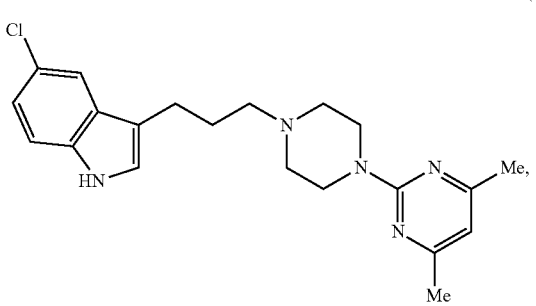
(18)
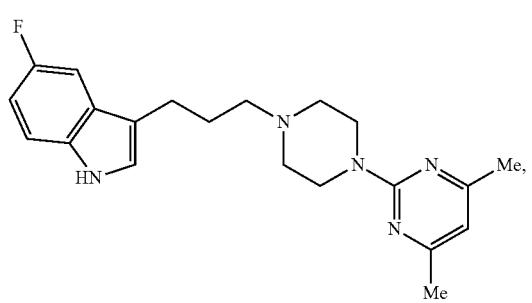
(19)
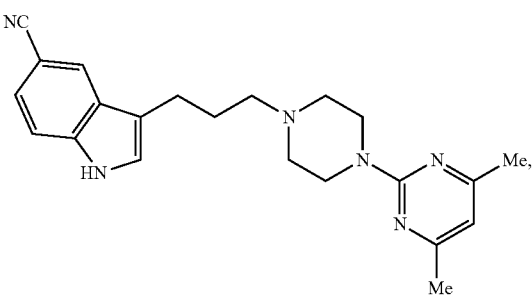
(20)
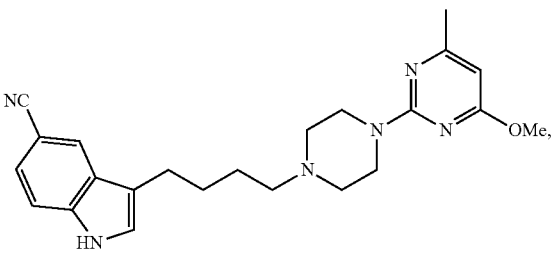
(21)

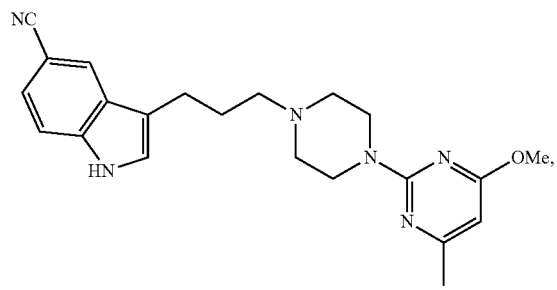
(22)
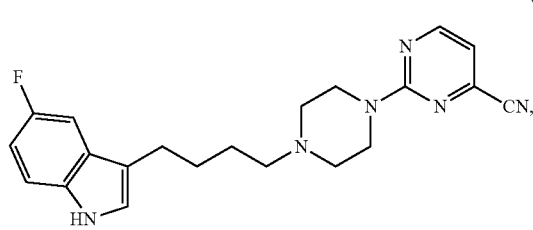
(23)
(24)
(25)
(26)
(27)
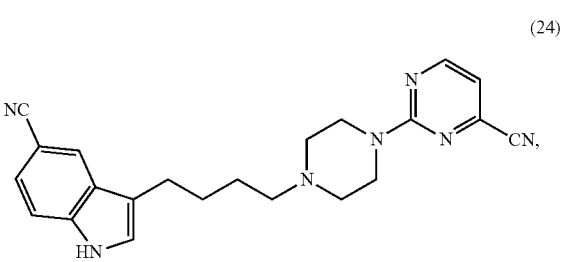
(28)
(29)
(30)
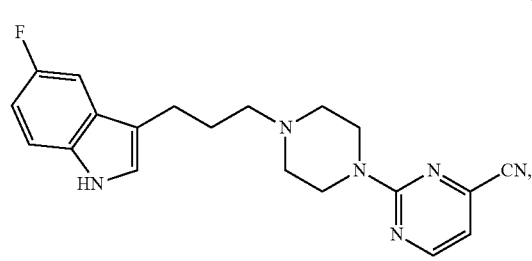
(31)
(32)
(33)

(34)
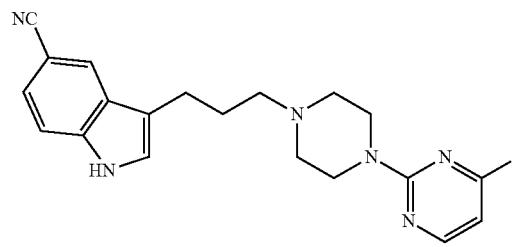
(35)
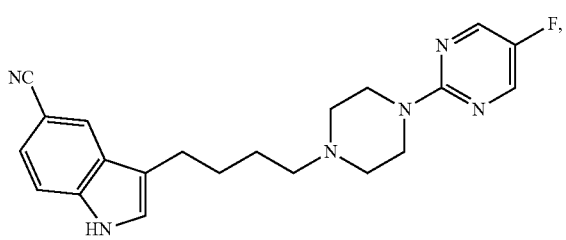
(36)
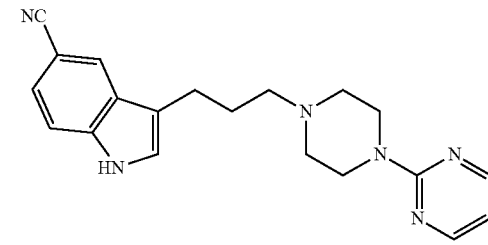
(37)
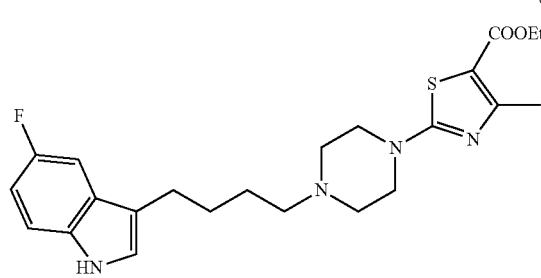
(38)
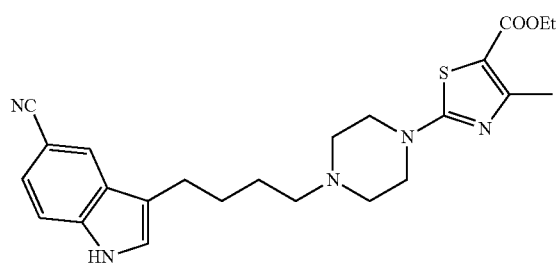
(39)
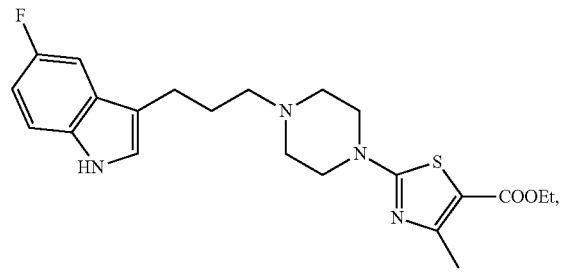
(40)
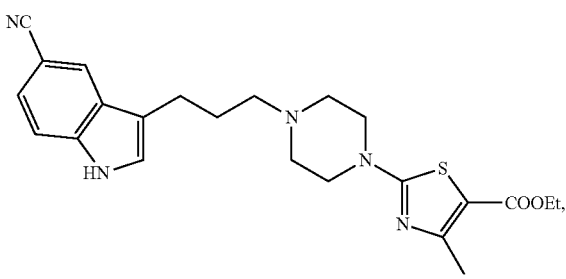
(41)
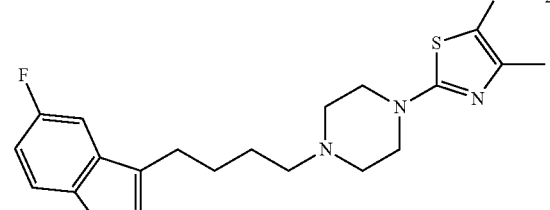
(42)
(43)
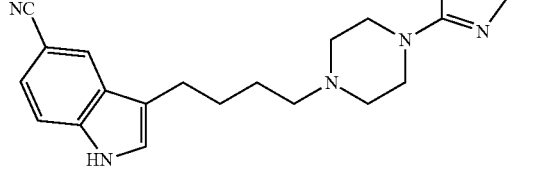
(44)
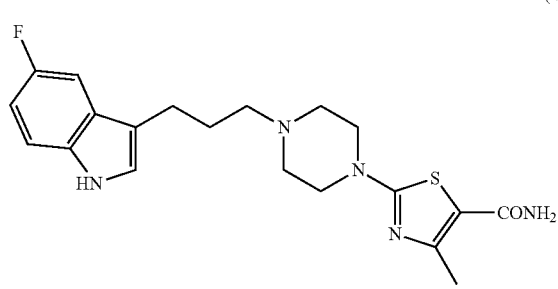
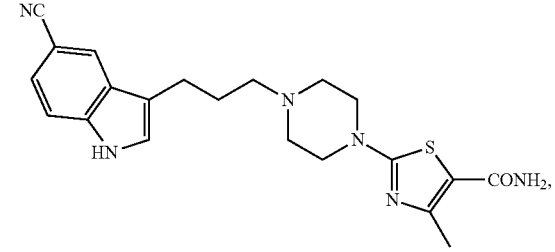

-continued
(45)
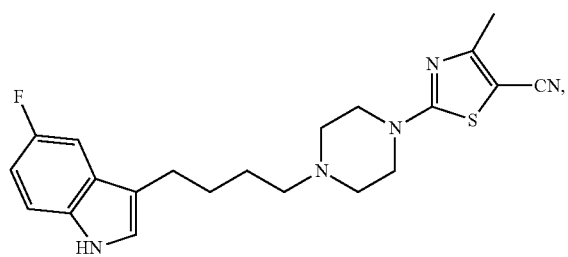
(46)
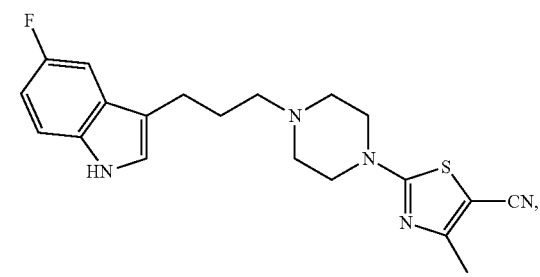
(47)
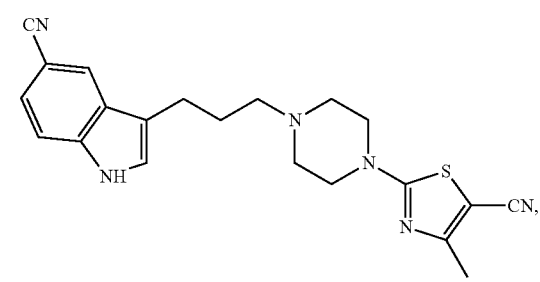
(48)
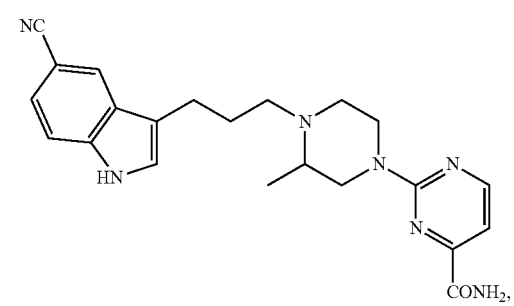
(49)
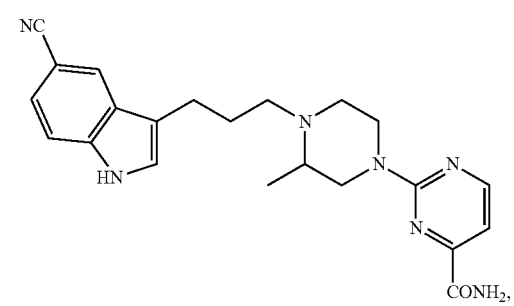
-continued
(50)
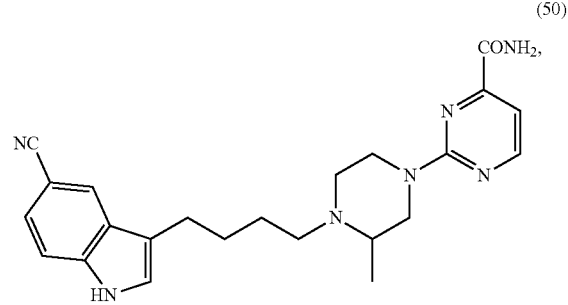
(51)
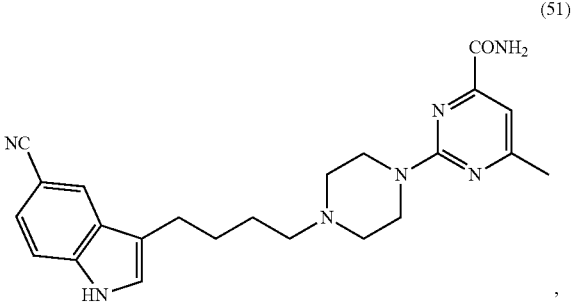
(52)
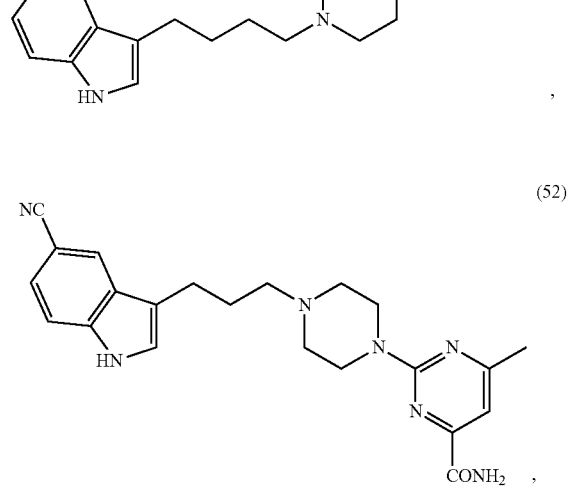
(53)
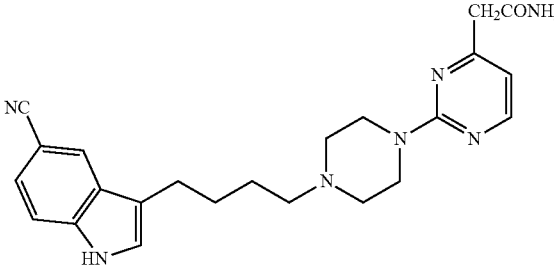
(54)
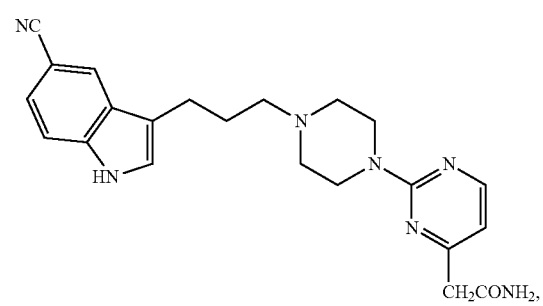

-continued

(55)
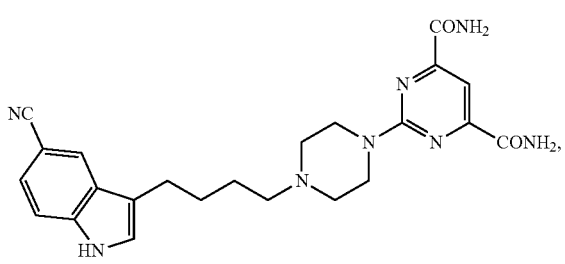

(56)
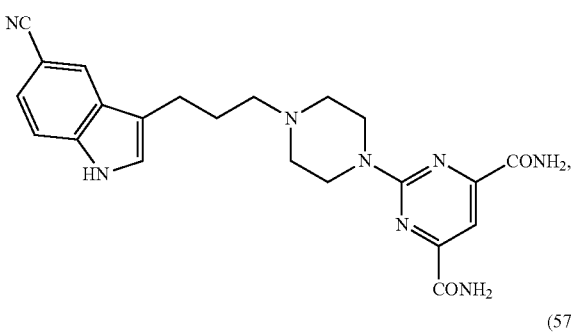

(57)
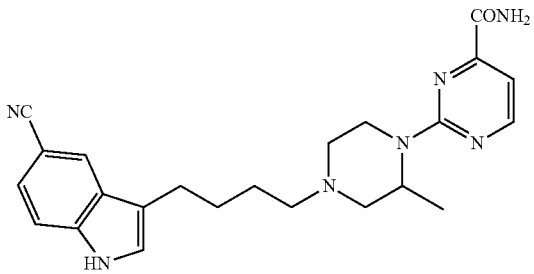

and

(58)
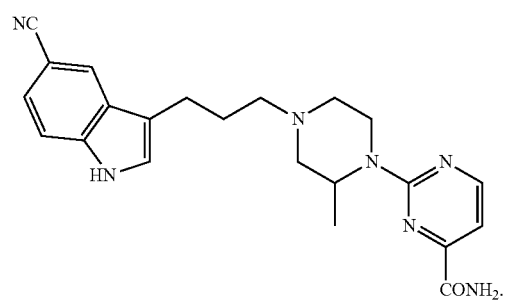

Unless otherwise stated, all suitable isotopic variations, stereoisomers, tautomers, N-oxides, solvates, metabolites, pharmaceutically acceptable salts and prodrugs of the compounds disclosed herein are within the scope of the invention.

To be more specific, in one aspect, the invention includes all suitable isotopic variations of the compounds disclosed herein. An isotopic variation of the compounds disclosed herein is defined as one in which at least one atom is replaced by an atom having the same atomic number but an atomic mass different from the atomic mass usually found in nature with the most abundant isotope(s) being preferred. Examples of isotopes that can be incorporated into the compounds disclosed herein include the isotopes of hydrogen, carbon, nitrogen, oxygen, sulphur, fluorine and chlorine, such as $H^2$, $H^3$, $C^{11}$, $C^{13}$, $C^{14}$, $N^{15}$, $O^{17}$, $O^{18}$, $S^{35}$, $F^{18}$ and $Cl^{36}$, respectively. Certain isotopic variations of the invention, for example, those in which a radioactive isotope such as $H^3$ or $C^{14}$ is incorporated, are useful in drug and/or substrate tissue distribution studies. Tritiated, i.e., $H^3$, and carbon-14, i.e., $C^{14}$, isotopes are particularly preferred for their ease of preparation and detectability. Further, substitution with isotopes such as deuterium, i.e., $H^2$, may afford certain therapeutic advantages resulting from greater metabolic stability, for example, increased in vivo half-life, reduced dosage requirements and hence may be preferred in some circumstances. Isotopic variations of the compounds disclosed herein can generally be prepared by conventional procedures such as using appropriate isotopic variations of suitable reagents.

Also part of the invention are those compounds wherein at least one atom has been replaced by an isotope of a different atom that can be used in vivo imaging techniques such as single photon emission computed tomography (SPECT) or positron emission tomography (PET). Examples for such derivatives usable in SPECT studies are compounds wherein a $Tc^{99m}$, $In^{111}$, $Rb^{82}$, $Cs^{137}$, $I^{123}$, $Ga^{67}$, $Ir^{192}$ or $Tl^{201}$ and preferably $I^{123}$ has been introduced (for iodination see e.g.: Coenen et al., *Radioiodination Reactions for Pharmaceuticals, Compendium for Effective Synthesis Strategies*, Springer, Dordrecht, 2006), while for PET applications $C^{11}$, $N^{13}$, $O^{15}$, $F^{18}$, $Rb^{82}$, $Sr^{82}$, and preferably $F^{18}$ (Coenen et al., *Fluorine-18 labeling methods: Features and possibilities of basic reactions*, Ernst Schering Res Found Workshop, 2007, Vol 62, p 15-50; Miller et al., Ang Chem Int Ed, 2008, Vol 47, p 8998) may be used.

In another aspect, structures depicted herein are also meant to include all stereoisomeric (e.g., enantiomeric, diastereomeric, and geometric (or conformational)) forms, for example, the R and S configurations for each asymmetric center, (Z) and (E) double bond isomers, and (Z) and (E) conformational isomers. Therefore, single stereochemical isomers as well as enantiomeric, diastereomeric, or geometric (or conformational) mixtures of the compounds disclosed herein are within the scope of the invention.

In another aspect, all tautomeric forms of the compounds disclosed herein are within the scope of the invention.

In another aspect, N-oxides of the compounds disclosed herein are also within the scope of the invention and may be prepared by oxidation of the corresponding nitrogen base using a conventional oxidizing agent such as hydrogen peroxide in the presence of an acid such as acetic acid at an elevated temperature, or by reaction with a peracid such as peracetic acid in a suitable solvent, e.g. dichloromethane, ethyl acetate or methyl acetate, or in chloroform or dichloromethane with 3-chloroperoxybenzoic acid.

In another aspect, salts of the compounds disclosed herein include pharmaceutically acceptable salts thereof, as well as other salts of such compounds which are not necessarily pharmaceutically acceptable salts, and which may be useful as intermediates for preparing and/or purifying compounds of Formula (I), (II), (III), (IV) or (V) and/or for separating enantiomers of compounds of Formula (I), (II), (III), (IV) or (V).

If the compound disclosed herein is a base, the desired salt may be prepared by any suitable method available in the art, for example, treatment of the free base with an inorganic acid, such as hydrochloric acid, hydrobromic acid, sulfuric acid, nitric acid, phosphoric acid, and the like; or with an organic acid, such as acetic acid, maleic acid, succinic acid, mandelic acid, fumaric acid, malonic acid, pyruvic acid, oxalic acid, glycolic acid, salicylic acid; a pyranosidyl acid, such as glucuronic acid or galacturonic acid; an alpha-hydroxy acid, such as citric acid or tartaric acid; an amino acid, such as aspartic acid or glutamic acid; an aromatic acid, such as benzoic acid or cinnamic acid; a sulfonic acid, such as p-toluenesulfonic acid or ethanesulfonic acid, and the like.

If the compound disclosed herein is an acid, the desired salt may be prepared by any suitable method, for example, treatment of the free acid with an inorganic or organic base, such as an amine (primary, secondary or tertiary), an alkali metal hydroxide or alkaline earth metal hydroxide, and the like. Some non-limiting examples of suitable salts include organic salts derived from amino acids, such as glycine and arginine, ammonia, such as primary, secondary and tertiary amines, and cyclic amines, such as piperidine, morpholine and piperazine, and inorganic salts derived from sodium, calcium, potassium, magnesium, manganese, iron, copper, zinc, aluminum, lithium, and the like.

COMPOSITION, FORMULATION AND ADMINISTRATION OF COMPOUNDS OF THE INVENTION

Provided herein is an pharmaceutical composition comprising the compound of Formula (I), (II), (III), (IV) or (V), or an individual isomer, racemic or non-racemic mixture of isomers or a pharmaceutically acceptable salt or solvate thereof, in admixture with at least one pharmaceutically acceptable carrier, adjuvant or vehicle, and optionally other therapeutic and/or prophylactic ingredients.

Appropriate carriers, adjuvants and vehicles are well known to those of skill in the art and described in, for example, Ansel et al., *Ansel's Pharmaceutical Dosage Forms and Drug Delivery Systems*, 2004, Lippincott, Williams & Wilkins, Philadelphia; Gennaro et al., *Remington: The Science and Practice of Pharmacy*, 2000, Lippincott, Williams & Wilkins, Philadelphia; and Rowe et al., *Handbook of Pharmaceutical Excipients*, 2005, Pharmaceutical Press, Chicago.

The compounds or compositions disclosed herein may be administered by any suitable means, including oral (including buccal and sublingual), topical, rectal, vaginal, transdermal, parenteral (intramuscular, intravenous, intraarterial, intraperitoneal or subcutaneous), intrapulmonary, intradermal, intrathecal, epidural and intranasal, as well as intralesional administration if desired for local treatment. The preferred method is oral administration, intraperitoneal or intravenous administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art.

Liquid preparations for oral administration may take the form of, for example, solutions, syrups or suspensions or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol) and preservatives (e.g., methyl or propyl p-hydroxybenzoates or sorbic acid).

For buccal administration, the compositions may take the form of tablets or lozenges formulated in conventional manner.

The compositions suitable for parenteral injection can comprise physiologically acceptable sterile aqueous or non-aqueous solvent, dispersant, suspending agent or emulsifying agent, as well as sterile dispersant for reforming a sterile injectable solution or dispersion. The examples of suitable aqueous or nonaqueous carriers, diluents, solvents or media include water, ethanol, polyols (propylene glycol, polyethylene glycol, glycerol, etc.), vegetable oil (such olive oil), injectable organic esters such as ethyl oleate and suitable mixtures thereof.

These compositions can further comprise excipients, such as preservative, wetting agent, emulsifying agent and dispersant. The use of various antibacterial agents and antifungal agents, such as nipagins, nautisan, phenol, sorbic acid, etc. can ensure effects of combating microorganisms. It is also desired to comprise isotonizing agents such as sugars, sodium chloride, etc. The use of substances for absorption delay, such as aluminum monostearate and gelatin, can achieve the prolonged absorption of injectable dosage form.

Besides active compounds, the suspensions can further comprise a suspending agent, such as ethoxylated isooctadecanol, polyoxyethylene sorbitol and polyoxyethylene sorbitan, microcrystalline cellulose, meta-aluminum hydroxide, bentonite, agar and tragacanth gum, or mixtures of these substances.

In some cases, it is desired to reduce the absorption rate of subcutaneously or intramuscularly administered drug for prolonging the effect of drug. This may be reached by using a liquid suspension of crystal or amorphous form with poor water solubility. Thus, the absorption rate of drug depends on its dissolution rate, while the dissolution rate depends on the size and form of crystal. Or, the delayed absorption of drug in parenteral administration may be reached by dissolving or dispersing the drug in an oil medium.

An injectable depot dosage form may be prepared by forming microcapsule substrate of drug in a biodegradable polymer such as polylactide-polyglycolide. The release rate of drug may be controlled according to the ratio of drug to polymer and the properties of the specifically used polymer. Other examples of biodegradable polymer comprise poly (orthoesters) and poly (anhydrides). The injectable depot dosage form can also be prepared by embedding drug in a liposome or microemulsion compatible to body tissues.

The injectable preparation may be sterilized by filtration using a bacterial filter or by incorporating a sterilizing agent in the form of a sterile solid composition, and the solid composition may be dissolved or dispersed in sterile water or other sterile injectable media before clinical application.

The compounds disclosed herein may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents or coloring agents. Formulations suitable for topical administration in the mouth include lozenges comprising active agents in a flavored base, usually sucrose and acacia or tragacanth; pastilles comprising the active ingredient in an inert base such as gelatine and glycerine or sucrose and acacia; and mouthwashes comprising the active ingredient in a suitable liquid carrier. In addition, ophthalmic formulation, eardrops, and eye drops are also contemplated as being within the scope of this invention The pharmaceutically acceptable compositions disclosed herein can be in the form of a rectal or vaginal suppository. These can be prepared by mixing the agent with the appropriate non-perfusion adjuvant. The mixture prepared this way is a solid at room temperature, but it becomes a liquid at rectal or vaginal temperature and releases the drug in the rectum or vagina. Such substances include cocoa fat, beeswax and polyethylene glycol.

For intranasal administration or administration by inhalation, the active compounds disclosed herein are conveniently delivered in the form of an aerosol spray from a pressurized container or a nebulizer or from a capsule using an inhaler or insufflators. In the case of a pressurized aerosol, a suitable propellant (e.g., dichlorodifluoromethane, trichlorofluoromethane, dichlorotetrafluoroethane, carbon dioxide or other suitable gas) and the dosage unit may be determined by providing a valve to deliver a metered amount. The medicament for pressurized container or nebulizer may contain a solution or suspension of the active compound, while for a capsule, it preferably should be in the form of powder. Capsules and cartridges (made, for example, from gelatin) for use in an inhaler or insufflator may be formulated containing a powder mix of a compound disclosed herein and a suitable powder base (e.g., lactose or starch).

Aerosol formulations for treatment of the conditions referred to above (e.g., migraine) in the average adult human are preferably arranged so that each metered dose or "puff" of aerosol contains 20 μg to 1000 μg of the compound disclosed herein. The overall daily dose with an aerosol will be within the range 100 μg to 10 mg. Administration may be several times daily, for example 2, 3, 4 or 8 times, giving for example 1, 2 or 3 doses each time.

The pharmaceutical preparations are preferably in unit dosage forms. In such form, the preparation is subdivided into unit doses containing appropriate quantities of the active component. The unit dosage form can be a packaged preparation, where the package contains discrete quantities of preparation, such as packeted tablets, capsules and powders in vials or ampoules. Also, the unit dosage form can be a capsule, tablet, cachet or lozenge itself, or it can be the appropriate number of any of these in packaged form.

It should be understood that the total amount per day of the compound or composition disclosed herein must be determined by a physician within the range of reliable medical decisions. As for any specific patient, the specific therapeutically amount must be determined based on various factors, including the diseases to be treated and severity thereof; the activity of the used specific compound; the used specific composition; the age, body weight, general health status, gender and food of patient; the administration time, route and excretory rate of the used specific compound; the duration of the treatment; the drug administered in combination or simultaneously with the specific compound; and similar factors well known in the art of medicine. For example, it is a common method in the art to increase gradually the dose of compound from a level lower than that for achieving desired therapeutical effects to a level enough to achieve the desired therapeutical effects. In general, the dose of a compound of Formula (I), (II), (III), (IV) or (V) for mammals especially human may be 0.1-1000 mg/kg body weight per day, preferably 1-100 mg/kg body weight per day. The administration may be once or several times a day, and each administration may include 1, 2 or 3 doses.

The compound of Formula (I), (II), (III), (IV) or (V) may either be administered alone or in combination with another therapeutically active compound, wherein the two compounds may either be administered simultaneously or sequentially. Some non-limiting examples of the therapeutically active compound which may advantageously be combined with the compounds of Formula (I), (II), (III), (IV) or (V) include sedatives or hypnotics, such as benzodiazepines; anticonvulsants, such as lamotrigine, valproic acid, topiramate, gabapentin, and carbamazepine; mood stabilizers such as lithium; dopaminergic drugs, such as dopamine agonists and L-Dopa; drugs to treat ADHD, such as atomoxetine; psychostimulants, such as modafinil, ketamine, methylphenidate and amphetamine; other antidepressants, such as mirtazapine, mianserin and buproprion; hormones, such as T3, estrogen, DHEA and testosterone; atypical antipsychotics, such as olanzapine and aripiprazole; typical antipsychotics, such as haloperidol; drugs to treat Alzheimer's diseases, such as cholinesterase inhibitors, memantine, and folate; S-Adenosyl-Methionine; immunomodulators, such as interferons; opiates, such as buprenorphins; angiotensin II receptor 1 antagonists (ATI antagonists); ACE inhibitors; statins; and alpha adrenergic antagonist, such as prazosin.

USES OF THE COMPOUNDS AND COMPOSITIONS OF THE INVENTION

The compounds and pharmaceutical compositions disclosed herein can be used in the manufacture of a medicament for preventing, treating or lessening the severity of a central nervous system dysfunction in mammals including humans, as well as for inhibiting serotonin reuptake and/or acting as $5-HT_{1A}$ receptor agonists.

Specifically, amount of the compounds used in the compositions disclosed herein is efficient to inhibit serotonin reuptake detectably and selectively, and has agonistic action for $5-HT_{1A}$ receptor. The compounds disclosed herein may be the agents used for treatment of the human central nervous system (CNS) dysfunction such as depression, anxiety.

The compounds disclosed herein may be used for, but not limited to, preventing, treating or lessening the severity of central nervous system dysfunction in mammals including humans by administering an effective amount of the compounds or compositions disclosed herein to patient. Such human central nervous system dysfunctions responsed to 5-HT receptor further include, but are not limited to, depression, anxiety, mania, schizophrenia, bipolar disorder, sleep disorder, obsessive compulsive disorder, panic disorder, post-traumatic stress disorder, movement disorder, sexual dysfunction, musculoskeletal pain disorder, cognitive disorder, memory disorder, Parkinson's disease, Huntington's disease, phobia, substance abuse or addiction, drug addiction withdrawal symptom or premenstrual tension syndrome.

Besides being useful for human treatment, these compounds and compositions are also useful for veterinary treatment of companion animals, exotic animals and mammals of farm animals. In other embodiments, animals include horses, dogs and cats. As used herein, the compounds disclosed herein include the pharmaceutically acceptable derivatives thereof.

SYNTHESIS OF COMPOUNDS

In order to describe the invention, the following examples are set forth. It is to be understood that the invention is not limited to these embodiments, but only provides the methods to practice the invention.

Generally, the compounds disclosed herein may be prepared by methods described herein, wherein the substituents are as defined for Formula (I), except where further noted. The following non-limiting schemes and examples are presented to further exemplify the invention.

Persons skilled in the art will recognize that the chemical reactions described herein may be readily adapted to prepare a number of other compounds disclosed herein, and alternative methods for preparing the compounds disclosed herein are deemed to be within the scope of the invention. For example, the synthesis of non-exemplified compounds according to the invention may be successfully performed by modifications apparent to those skilled in the art, e.g., by appropriately protecting interfering groups, by utilizing other suitable reagents known in the art other than those described herein, and/or by making routine modifications of reaction conditions. Alternatively, other reactions disclosed herein or known in the art will be recognized as having applicability for preparing other compounds disclosed herein.

In the examples described below, unless otherwise indicated all temperatures are set forth in degrees Celsius. Reagents were purchased from commercial suppliers such as Aldrich Chemical Company, Arco Chemical Company and Alfa Chemical Company, and were used without further purification unless otherwise indicated. Common solvents were purchased from commercial suppliers such as Shantou XiLong Chemical Factory, Guangdong Guanghua Reagent Chemical Factory Co. Ltd., Guangzhou Reagent Chemical Factory, Tianjin YuYu Fine Chemical Ltd., Tianjin Fucheng Reagent Chemical Factory, Wuhan Xinhuayuan Technology Development Co. Ltd., Qingdao Tenglong Reagent Chemical Ltd., and Qingdao Ocean Chemical Factory.

Anhydrous THF, dioxane, toluene and ether were obtained by refluxing the solvent with sodium. Anhydrous $CH_2Cl_2$ and $CHCl_3$ were obtained by refluxing the solvent with $CaH_2$. EtOAc, PE, hexane, DMAC and DMF were treated with anhydrous $Na_2SO_4$ prior to use.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was conducted using a silica gel column. Silica gel (300-400 mesh) was purchased from Qingdao Ocean Chemical Factory. $^1$H NMR spectra were obtained by using $CDCl_3$, $d_6$-DMSO, $CD_3OD$ or $d_6$-acetone solutions (reported in ppm), with TMS (0 ppm) or chloroform (7.25 ppm) as the reference standard. When peak multiplicities were reported, the following abbreviations were used: s (singlet), d (doublet), t (triplet), m (multiplet), br (broadened), dd (doublet of doublets), dt (doublet of triplets). Coupling constants, when given, were reported in Hertz (Hz).

Low-resolution mass spectral (MS) data were generally determined on Agilent 1200 or Agilent 6120 Series LC-MS (Column Type: Zorbax SB-C18, 2.1×30 mm, 3.5 micron, 6 min, and 0.6 mL/min flow rate). The mobile phase was 5-95% (0.1% formic acid in $CH_3CN$) in (0.1% formic acid in $H_2O$), and the generated chromatograms were monitored at 210/254 nm by UV detector with low response EFI mode (ESI).

Purity of compounds was assessed by Agilent 1100 Series high performance liquid chromatography (HPLC) with UV detection at 210 nm and 254 nm. Column was operated at 40° C.

The following abbreviations are used throughout the specification:
aq. aqueous solution
$CH_2Cl_2$, DCM dichloromethane
$CDCl_3$ chloroform-d
DIEA, DIPEA diisopropylethylamine
DMF N,N-dimethylformamide
DMAP 4-dimethylaminopyridine
DMSO dimethyl sulfoxide
EtOAc, EA ethyl acetate
$Et_3N$, TEA triethylamine
EDTA ethylenediaminetetraacetic acid
EGTA ethylenebis(oxyethylenenitrilo)tetraacetic acid
g gram
h hour
$H_2SO_4$ sulfuric acid
HBTU O-benzotriazolyl-N,N,N',N'-tetramethyluronium hexafluorophosphate
$K_2CO_3$ potassium carbonate
KI potassium iodide
KCl potassium chloride
MeOH, $CH_3OH$ methanol
$MgSO_4$ magnesium sulfate
mL, ml milliliter
min minute
$N_2$ nitrogen
RT, rt, r.t. room temperature
$NaBH_4$ sodium borohydride
$NH_4Cl$ ammonia chloride
$NaHCO_3$ sodium bicarbonate
$NaH_2PO_4$ sodium dihydrogen phosphate
NaCl sodium chloride
$Na_2SO_4$ sodium sulfate
PCC pyridinium chlorochromate
PE petroleum ether (60-90° C.)
THF tetrahydrofuran
Tri-HCl 2-amino-2-(hydroxymethyl)-1,3-propanediol hydrochloride
TsCl tosyl chloride The following synthesis scheme describes the preparation of the compounds disclosed herein. Unless otherwise indicated, each $R^1$, $R^5$, $R^6$, $R^7$, $R^8$ and $R^9$ has the definitions as described herein.

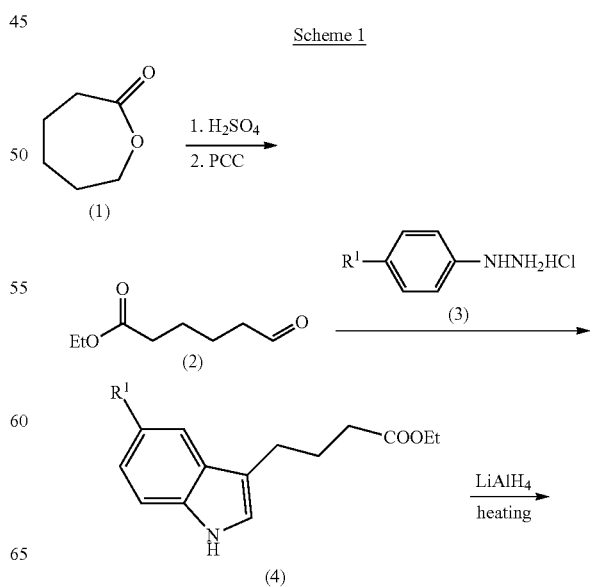

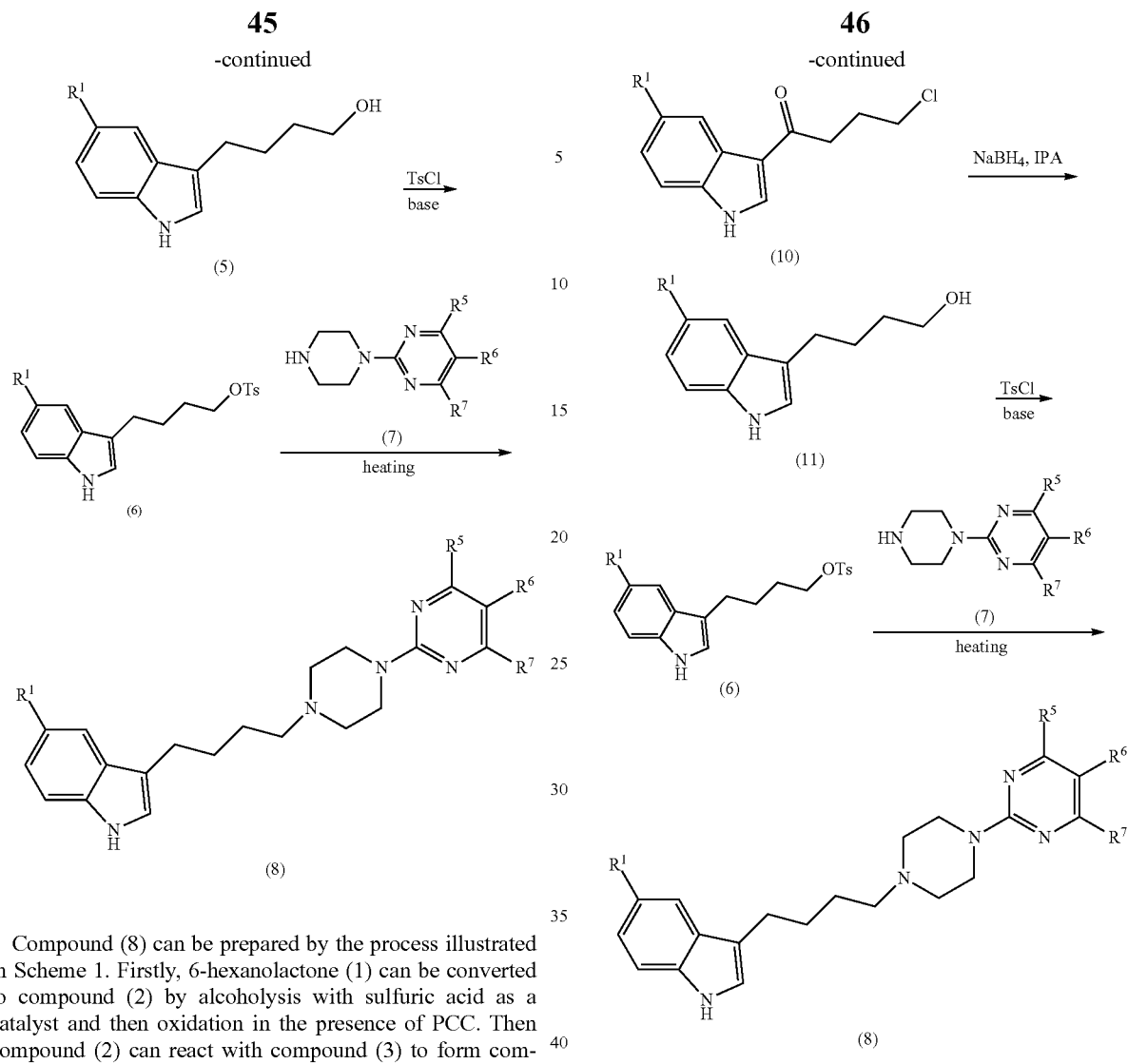

Compound (8) can be prepared by the process illustrated in Scheme 1. Firstly, 6-hexanolactone (1) can be converted to compound (2) by alcoholysis with sulfuric acid as a catalyst and then oxidation in the presence of PCC. Then compound (2) can react with compound (3) to form compound (4) by Fischer indole cyclization in an alcoholic solvent such as ethanol, isopropanol or tert-butanol. Compound (4) can further react with a reducing agent such as lithium aluminum hydride to form compound (5) at a suitable temperature such as 40-120° C. The hydroxyl group of compound (5) can be converted to p-toluenesulfonate group to form compound (6), and then compound (6) can further react with compound (7) in the presence of an inorganic base such as potassium carbonate or sodium carbonate, or an organic base such as triethylamine in a suitable solvent such as acetonitrile, tetrahydrofuran, ethanol or DMF to afford the objective compound (8) by nucleophilic substitution.

Compound (8) can also be prepared by the process illustrated in Scheme 2. Firstly, Friedel-Crafts acylation reaction of compound (9) with chlorobutyryl chloride can give compound (10). Compound (10) can then react with a reducing agent such as sodium borohydride or lithium aluminum hydride to afford compound (11) in a suitable solvent such as tert-butanol or isopropanol. Then the hydroxyl group of compound (11) can be converted to p-toluenesulfonate group to form compound (6), and compound (6) can further react with compound (7) in the presence of an inorganic base such as potassium carbonate or sodium carbonate, or an organic base such as triethylamine in a suitable solvent such as acetonitrile, tetrahydrofuran, ethanol or DMF to afford the objective compound (8) by nucleophilic substitution.

Scheme 2

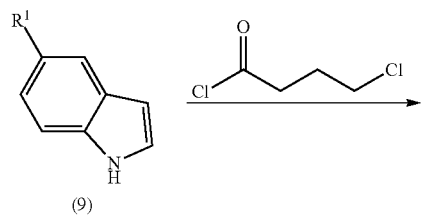

Scheme 3

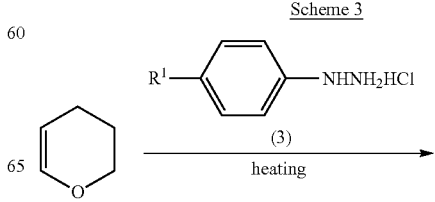

-continued

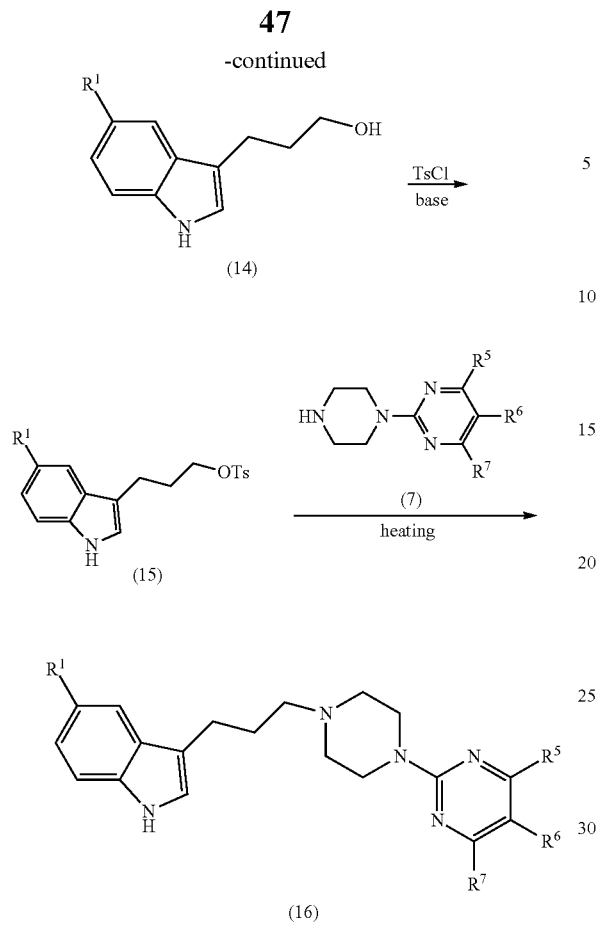

Compound (16) can be prepared by the process illustrated in Scheme 3. Firstly, tetrahydropyrane (13) can react with compound (3) to give compound (14) by Fischer indole cyclization at a suitable temperature such as 40-120° C. Then the hydroxyl group of compound (14) can be converted to p-toluenesulfonate group to form compound (15), and compound (15) can further react with compound (7) in the presence of an inorganic base such as potassium carbonate or sodium carbonate, or an organic base such as triethylamine in a suitable solvent such as acetonitrile, tetrahydrofuran, ethanol or DMF to afford the objective compound (16) by nucleophilic substitution.

Scheme 4

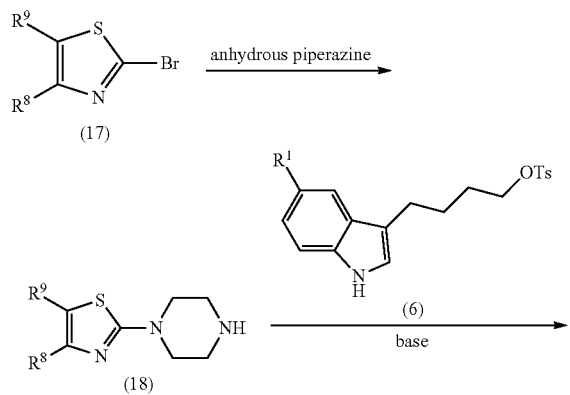

-continued

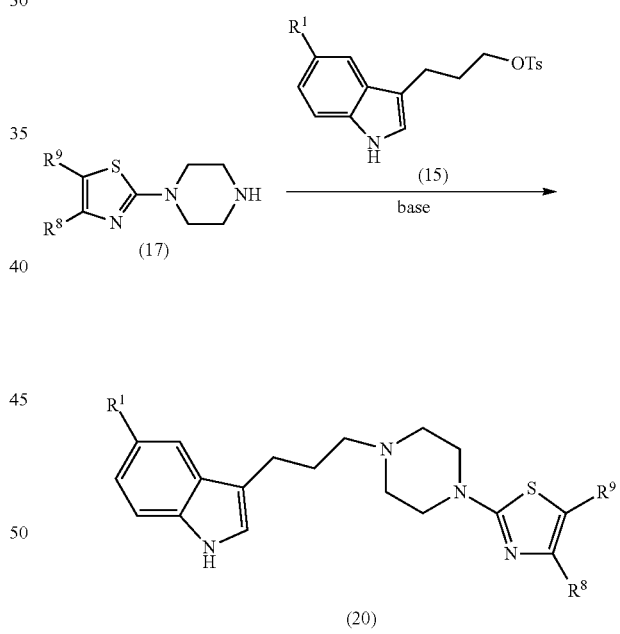

Compound (19) can be prepared by the process illustrated in Scheme 4. Firstly, compound (17) can be converted to compound (18) by reacting with anhydrous piperazine. Then nucleophilic substitution reaction of compound (18) with compound (6) can give the objective compound (19) in the presence of an inorganic base such as potassium carbonate or sodium carbonate, or an organic base such as triethylamine in a suitable solvent such as acetonitrile, tetrahydrofuran, ethanol, DMF or DMSO and at a suitable temperature such as 30-100° C.

Scheme 5

Compound (20) can be prepared by the process illustrated in Scheme 5. Nucleophilic substitution reaction of compound (17) with compound (15) can give the objective compound (20) in the presence of an inorganic base such as potassium carbonate or sodium carbonate, or an organic base such as triethylamine in a suitable solvent such as acetonitrile, tetrahydrofuran, ethanol, DMF or DMSO and at a suitable temperature such as 30-100° C.

The compounds, pharmaceutical compositions and applications thereof disclosed herein will be further illustrated in combination with the following examples.

EXAMPLES

Example 1 3-(4-(4-(4,6-Dimethoxypyrimidin-2-yl)piperazin-1-yl)butyl)-1H-indole

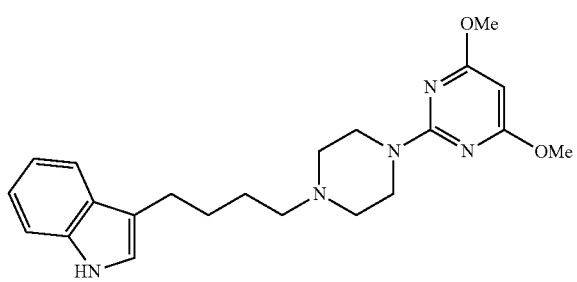 [SMILES: COc1cc(OC)nc(N2CCN(CCCCc3c[nH]c4ccccc34)CC2)n1]

Step 1) ethyl 6-oxohexanoate

To a mixture of 6-hexanolactone (15.0 g, 0.13 mol) in ethanol (125 mL) was added concentrated sulfuric acid (1.1 mL) dropwise. The reaction mixture was heated to 80° C. and stirred for 24 hours. Then the reaction mixture was cooled to rt and concentrated in vacuo. The residue was diluted with ice water (150 mL), and extracted with EtOAc (150 mL×3). The combined organic phases were dried over anhydrous $Na_2SO_4$, filtered and concentrated in vacuo. The residue was dried to obtain ethyl 6-hydroxyhexanoate (10.3 g).

To a solution of PCC (16.2 g, 75.5 mmol) in DCM (140 mL) was added a mixture of ethyl 6-hydroxyhexanoate (10.3 g, 64.3 mmol) in DCM (20 mL) dropwise at 0° C. The reaction mixture was stirred at rt for 2 hours, and then EtOAc (100 mL) was added. The resulting mixture was filtered and concentrated in vacuo. The residue was purified by silica gel column chromatography (PE/EtOAc (v/v)=10/1) to give the title compound as a white solid (9.28 g, 45%). The compound was characterized by the following spectroscopic data: LC-MS (ESI, pos. ion) m/z: 159.3 $[M+H]^+$.

Step 2) ethyl 4-(1H-indol-3-yl)butanoate

To a mixture of ethyl 6-oxohexanoate (1.0 g, 6.3 mmol) in ethanol (125 mL) was added phenylhydrazine (0.7 g, 6.8 mmol) at rt. The reaction mixture was heated to 80° C. and stirred for 20 hours. Then the reaction mixture was cooled to rt and concentrated in vacuo. The residue was diluted with ice water (100 mL) and extracted with EtOAc (150 mL×3). The combined organic phases were dried over anhydrous $Na_2SO_4$, filtered and concentrated in vacuo. The residue was purified by silica gel column chromatography (PE/EtOAc (v/v)=4/1) to give the title compound as a white solid (0.63 g, 43.0%). The compound was characterized by the following spectroscopic data: LC-MS (ESI, pos. ion) m/z: 232.2 $[M+H]^+$.

Step 3) 4-(1H-indol-3-yl)butan-1-ol

To a solution of ethyl 4-(1H-indol-3-yl)butanoate (0.29 g, 1.25 mmol) in THF (20 mL) was added lithium aluminum hydride (0.19 g, 5.08 mmol) in portions at 0° C. After the reaction mixture was stirred at rt for 1 hour, it was heated to 80° C. and stirred for 20 hours. Then the reaction mixture was cooled to 0° C., quenched with saturated aqueous sodium sulfate solution (1 mL) and diluted with EtOAc (150 mL). The resulting mixture was filtered, and the filtrate was concentrated in vacuo. The residue was purified by silica gel column chromatography (PE/EtOAc (v/v)=2/1) to give the title compound as a white solid (0.18 g, 75%). The compound was characterized by the following spectroscopic data: LC-MS (ESI, pos. ion) m/z: 190.2 $[M+H]^+$.

Step 4) 4-(1H-indol-3-yl)butyl 4-methylbenzenesulfonate

To a mixture of 4-(1H-indol-3-yl)butan-1-ol (0.36 g, 1.9 mmol) in DCM (20 mL) were added TEA (0.3 mL, 2.28 mmol) and TsCl (0.43 g, 2.28 mmol). After the reaction mixture was stirred at rt for 4 hours, it was quenched with water (100 mL). The organic phase was separated, dried over anhydrous $Na_2SO_4$, filtered and concentrated in vacuo. The residue was purified by silica gel column chromatography (PE/EtOAc (v/v)=4/1) to give the title compound as a white solid (0.42 g, 64.0%). The compound was characterized by the following spectroscopic data: LC-MS (ESI, pos. ion) m/z: 344.2 $[M+H]^+$.

Step 5) 4,6-dimethoxy-2-(piperazin-1-yl)pyrimidine

To a mixture of 2-chloro-4,6-dimethoxypyrimidine (1.26 g, 7.2 mmol) in DMF (10 mL) were added potassium carbonate (1.00 g, 7.2 mmol) and anhydrous piperazine (1.24 g, 14.4 mmol). The reaction mixture was heated to 100° C. and stirred for 10 hours. Then the reaction mixture was cooled to rt, diluted with water (10 mL) and extracted with EtOAc (20 mL×3). The combined organic phases were dried over anhydrous $Na_2SO_4$, filtered and concentrated in vacuo. The residue was purified by silica gel column chromatography ($CH_2Cl_2$/MeOH (v/v)=20/1) to give the title compound as yellow oil (1.05 g, 65.0%). The compound was characterized by the following spectroscopic data: LC-MS (ESI, pos. ion) m/z: 225.1 $[M+H]^+$ and $^1$H NMR ($CDCl_3$, 400 MHz) δ (ppm): 5.39 (s, 1H), 3.86 (s, 6H), 3.78 (t, J=4.9 Hz, 4H), 3.47 (t, J=5.0 Hz, 4H).

Step 6) 3-(4-(4-(4,6-dimethoxypyrimidin-2-yl)piperazin-1-yl)butyl)-1H-indole To a mixture of 4-(1H-indol-3-yl)butyl 4-methylbenzenesulfonate (0.2 g, 0.58 mmol) and 4,6-dimethoxy-2-(piperazin-1-yl)pyrimidine (0.13 g, 0.58 mmol) in acetonitrile (15 mL) were added potassium carbonate (0.12 g, 0.87 mmol) and potassium iodide (20 mg, 0.12 mmol) under an nitrogen atmosphere. The reaction mixture was heated to 80° C. and stirred for 20 hours. Then the reaction mixture was cooled to rt and concentrated in vacuo. The residue was purified by silica gel column chromatography (PE/EtOAc (v/v)=1/1) to give the title compound as a white solid (149 mg, 65.0%). The compound was characterized by the following spectroscopic data: LC-MS (ESI, pos. ion) m/z: 396.3 $[M+H]^+$ and $^1$H NMR ($CDCl_3$, 400 MHz) δ (ppm): 7.95 (br s, 1H), 7.61 (d, J=7.8 Hz, 1H), 7.35 (d, J=8.0 Hz, 1H), 7.20-7.16 (m, 1H), 7.12-7.09 (m, 1H), 6.98 (t, J=1.8 Hz, 1H), 5.36 (s, 1H), 3.85 (s, 6H), 3.82-3.78 (m, 4H), 2.79 (t, J=7.4 Hz, 2H), 2.47 (t, J=5.0 Hz, 4H), 2.42 (t, J=7.6 Hz, 2H), 1.78-1.72 (m, 2H), 1.67-1.61 (m, 2H).

Example 2 3-(4-(4-(4,6-Dimethoxypyrimidin-2-yl)piperazin-1-yl)butyl)-5-methoxy-1H-indole

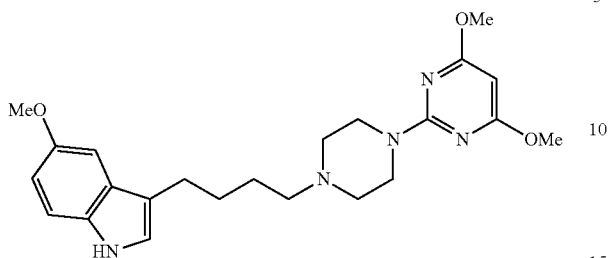

Step 1) ethyl 4-(5-methoxy-1H-indol-3-yl)butanoate

The title compound was prepared by the procedure described in step 2 of example 1, using ethyl 6-oxohexanoate (1.0 g, 6.3 mmol) and 4-methoxyphenylhydrazine hydrochloride (1.2 g, 6.8 mmol) in ethanol (125 mL) to give the crude product, which was purified by silica gel column chromatography (PE/EtOAc (v/v)=4/1) to give the title compound as a white solid (0.49 g, 30.0%). The compound was characterized by the following spectroscopic data: LC-MS (ESI, pos. ion) m/z: 262.2 [M+H]$^+$.

Step 2) 4-(5-methoxy-1H-indol-3-yl)butan-1-ol

The title compound was prepared by the procedure described in step 3 of example 1, using ethyl 4-(5-methoxy-1H-indol-3-yl)butanoate (0.33 g, 1.27 mmol) and lithium aluminum hydride (0.19 g, 5.08 mmol) in THF (25 mL) to give the crude product, which was purified by silica gel column chromatography (PE/EtOAc (v/v)=2/1) to give the title compound as a white solid (0.21 g, 75%). The compound was characterized by the following spectroscopic data: LC-MS (ESI, pos. ion) m/z: 220.2 [M+H]$^+$.

Step 3) 4-(5-methoxy-1H-indol-3-yl)butyl 4-methylbenzenesulfonate

The title compound was prepared by the procedure described in step 4 of example 1, using 4-(5-methoxy-1H-indol-3-yl)butan-1-ol (0.42 g, 1.9 mmol), TEA (0.3 mL, 2.28 mmol) and TsCl (0.43 g, 2.28 mmol) in DCM (20 mL) to give the crude product, which was purified by silica gel column chromatography (PE/EtOAc (v/v)=4/1) to give the title compound as a white solid (0.46 g, 65.0%). The compound was characterized by the following spectroscopic data: LC-MS (ESI, pos. ion) m/z: 374.1 [M+H]$^+$.

Step 4) 3-(4-(4-(4,6-dimethoxypyrimidin-2-yl)piperazin-1-yl)butyl)-5-methoxy-1H-indole The title compound was prepared by the procedure described in step 6 of example 1, using 4-(5-methoxy-1H-indol-3-yl)butyl 4-methylbenzenesulfonate (216 mg, 0.58 mmol), 4,6-dimethoxy-2-(piperazin-1-yl)pyrimidine (130 mg, 0.58 mmol), potassium carbonate (120 mg, 0.87 mmol) and potassium iodide (20 mg, 0.12 mmol) in acetonitrile (15 mL) to give the title compound as a white solid (148 mg, 60.0%). The compound was characterized by the following spectroscopic data: LC-MS (ESI, pos. ion) m/z: 426.3 [M+H]$^+$ and $^1$H NMR (CDCl$_3$, 400 MHz) δ (ppm): 7.98 (br s, 1H), 7.23 (d, J=8.8 Hz, 1H), 7.03 (d, J=2.0 Hz, 1H), 6.95 (d, J=1.2 Hz, 1H), 6.84 (dd, J=8.8, 2.2 Hz, 1H), 6.98 (s, 1H), 3.87 (s, 3H), 3.85 (s, 6H), 3.80 (t, J=5.0 Hz, 4H), 2.75 (t, J=7.3 Hz, 2H), 2.47 (t, J=4.9 Hz, 4H), 2.42 (t, J=7.6 Hz, 2H), 1.74-1.72 (m, 2H), 1.65-1.64 (m, 2H).

Example 3 5-Chloro-3-(4-(4-(4,6-dimethoxypyrimidin-2-yl)piperazin-1-yl)butyl)-1H-indole

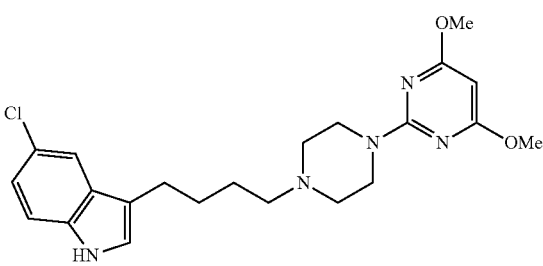 [SMILES: COc1cc(OC)nc(N2CCN(CCCCc3c[nH]c4ccc(Cl)cc34)CC2)n1]

Step 1) ethyl 4-(5-chloro-1H-indol-3-yl)butanoate

The title compound was prepared by the procedure described in step 2 of example 1, using ethyl 6-oxohexanoate (2.0 g, 12.6 mmol) and 4-chlorophenylhydrazine hydrochloride (2.4 g, 13.6 mmol) in ethanol (125 mL) to give the crude product, which was purified by silica gel column chromatography (PE/EtOAc (v/v)=4/1) to give the title compound as a white solid (1.16 g, 35%). The compound was characterized by the following spectroscopic data: LC-MS (ESI, pos. ion) m/z: 266.2 [M+H]$^+$.

Step 2) 4-(5-chloro-1H-indol-3-yl)butan-1-ol

The title compound was prepared by the procedure described in step 3 of example 1, using ethyl 4-(5-chloro-1H-indol-3-yl)butanoate (0.67 g, 2.54 mmol) with lithium aluminum hydride (0.39 g, 10.16 mmol) in THF (25 mL) to give the crude product, which was purified by silica gel column chromatography (PE/EtOAc (v/v)=2/1) to give the title compound as a white solid (0.42 g, 74%). The compound was characterized by the following spectroscopic data: LC-MS (ESI, pos. ion) m/z: 224.2 [M+H]$^+$.

Step 3) 4-(5-chloro-1H-indol-3-yl)butyl 4-methylbenzenesulfonate

The title compound was prepared by the procedure described in step 4 of example 1, using 4-(5-chloro-1H-indol-3-yl)butan-1-ol (0.43 g, 1.9 mmol), TEA (0.3 mL, 2.28 mmol) and TsCl (0.43 g, 2.28 mmol) in DCM (20 mL) to give the crude product, which was purified by silica gel column chromatography (PE/EtOAc (v/v)=4/1) to give the title compound as a white solid (0.57 g, 79%). The compound was characterized by the following spectroscopic data: LC-MS (ESI, pos. ion) m/z: 378.1 [M+H]$^+$.

Step 4) 5-chloro-3-(4-(4-(4,6-dimethoxypyrimidin-2-yl)piperazin-1-yl)butyl)-1H-indole The title compound was prepared by the procedure described in step 6 of example 1, using 4-(5-chloro-1H-indol-3-yl)butyl 4-methylbenzenesulfonate (0.22 g, 0.58 mmol), 4,6-dimethoxy-2-(piperazin-1-yl)pyrimidine (0.13 g, 0.58 mmol), potassium carbonate (0.12 g, 0.87 mmol) and potassium iodide (20 mg, 0.12 mmol) in acetonitrile (15 mL) to give the title compound as a white solid (160 mg, 64%). The compound was characterized by the following spectroscopic data: LC-MS (ESI, pos. ion) m/z: 430.3 [M+H]$^+$ and $^1$H NMR (CDCl$_3$, 400 MHz) δ (ppm): 8.43 (br s, 1H), 7.55 (s, 1H), 7.20 (d, J=8.6 Hz, 1H), 7.10 (d, J=8.5 Hz, 1H), 6.95 (s, 1H), 5.36 (s, 1H), 3.84 (s, 6H), 3.82 (d, J=4.7 Hz, 4H), 2.72 (t, J=7.2 Hz, 2H), 2.47-2.44 (m, 4H), 2.41 (t, J=7.5 Hz, 2H), 1.73-1.67 (m, 2H), 1.64-1.61 (m, 2H).

Example 4 3-(4-(4-(4,6-Dimethoxypyrimidin-2-yl)piperazin-1-yl)butyl)-5-fluoro-1H-indole

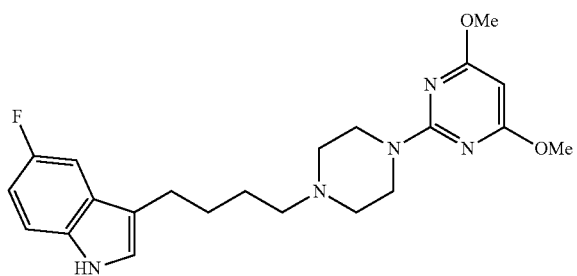 [SMILES: COc1cc(OC)nc(N2CCN(CCCCc3c[nH]c4ccc(F)cc34)CC2)n1]

Step 1) ethyl 4-(5-fluoro-1H-indol-3-yl)butanoate

The title compound was prepared by the procedure described in step 2 of example 1, using ethyl 6-oxohexanoate (1.0 g, 6.3 mmol) and 4-fluorophenylhydrazine hydrochloride (1.1 g, 6.8 mmol) in ethanol (125 mL) to give the crude product, which was purified by silica gel column chromatography (PE/EtOAc (v/v)=4/1) to give the title compound as a white solid (0.94 g, 60%). The compound was characterized by the following spectroscopic data: LC-MS (ESI, pos. ion) m/z: 250.2 [M+H]$^+$.

Step 2) 4-(5-fluoro-1H-indol-3-yl)butan-1-ol

The title compound was prepared by the procedure described in step 3 of example 1, using ethyl 4-(5-fluoro-1H-indol-3-yl)butanoate (0.32 g, 1.27 mmol) and lithium aluminum hydride (0.19 g, 5.08 mmol) in THF (25 mL) to give the crude product, which was purified by silica gel column chromatography (PE/EtOAc (v/v)=2/1) to give the title compound as a white solid (0.20 g, 76%). The compound was characterized by the following spectroscopic data: LC-MS (ESI, pos. ion) m/z: 208.2 [M+H]$^+$.

Step 3) 4-(5-fluoro-1H-indol-3-yl)butyl 4-methylbenzenesulfonate

The title compound was prepared by the procedure described in step 4 of example 1, using 4-(5-fluoro-1H-indol-3-yl)butan-1-ol (0.39 g, 1.9 mmol), TEA (0.3 mL, 2.28 mmol) and TsCl (0.43 g, 2.28 mmol) in DCM (20 mL) to give the crude product, which was purified by silica gel column chromatography (PE/EtOAc (v/v)=4/1) to give the title compound as a white solid (0.45 g, 65.0%). The compound was characterized by the following spectroscopic data: LC-MS (ESI, pos. ion) m/z: 362.2 [M+H]$^+$.

Step 4) 3-(4-(4-(4,6-dimethoxypyrimidin-2-yl)piperazin-1-yl)butyl)-5-fluoro-1H-indole The title compound was prepared by the procedure described in step 6 of example 1, using 4-(5-fluoro-1H-indol-3-yl)butyl 4-methylbenzenesulfonate (210 mg, 0.58 mmol), 4,6-dimethoxy-2-(piperazin-1-yl)pyrimidine (130 mg, 0.58 mmol), potassium carbonate (120 mg, 0.87 mmol) and potassium iodide (20 mg, 0.12 mmol) in acetonitrile (15 mL) to give the title compound as a white solid (168 mg, 70%). The compound was characterized by the following spectroscopic data: LC-MS (ESI, pos. ion) m/z: 414.3 [M+H]$^+$ and $^1$H NMR (CDCl$_3$, 400 MHz) δ (ppm): 8.01 (br s, 1H), 7.26-7.22 (m, 2H), 7.02 (d, J=1.6 Hz, 1H), 6.92 (td, J=9.1, 2.4 Hz, 1H), 5.36 (s, 1H), 3.85 (s, 6H), 3.81 (t, J=4.9 Hz, 4H), 2.74 (t, J=7.4 Hz, 2H), 2.46 (t, J=5.1 Hz, 4H), 2.41 (t, J=7.6 Hz, 2H), 1.75-1.69 (m, 2H), 1.66-1.58 (m, 2H).

Example 5 3-(4-(4-(4,6-Dimethoxypyrimidin-2-yl)piperazin-1-yl)butyl)-1H-indole-5-carbonitrile

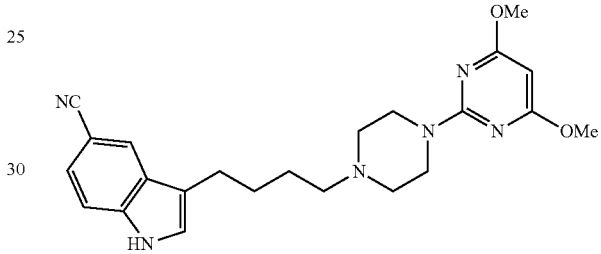

Step 1) 3-(4-chlorobutanoyl)-1H-indole-5-carbonitrile

To a mixture of aluminium chloride (9.0 g, 68.0 mmol) in DCM (90 mL) was added 4-chlorobutyryl chloride (9.6 g, 68.0 mmol) dropwise at 0° C. After the mixture was stirred at 0° C. for 30 mins, to it was added a mixture of 5-cyanoindole (8.1 g, 57.0 mmol) in DCM (800 mL) dropwise. The reaction mixture was heated to rt and stirred for 2 hours. Then the reaction mixture was poured into a mixture of ice water (50 g) in concentrated hydrochloric acid (50 mL), and stirred at rt for 20 hours. The resulting mixture was filtered, and the filter cake was washed with water (10 mL) and EtOAc (10 mL) in turn. Then the filter cake was dried to give the title compound as a yellow solid (8.9 g, 63%). The compound was characterized by the following spectroscopic data: LC-MS (ESI, pos. ion) m/z: 247.1 [M+H]$^+$ and $^1$H NMR (CD$_3$OD, 400 MHz) δ (ppm): 8.63 (d, J=0.7 Hz, 1H), 8.35 (s, 1H), 7.62-7.60 (m, 1H), 7.52 (dd, J=8.4, 1.5 Hz, 1H), 3.69 (t, J=6.5 Hz, 2H), 3.11 (t, J=7.2 Hz, 2H), 2.24-2.17 (m, 2H).

Step 2) 3-(4-hydroxybutyl)-1H-indole-5-carbonitrile

To a mixture of 3-(4-chlorobutanoyl)-1H-indole-5-carbonitrile (0.49 g, 2.0 mmol) in isopropanol (20 mL) was added sodium borohydride (0.23 g, 6.0 mmol) in portions at 0° C. The reaction mixture was heated to 80° C. and stirred for 6 hours. Then the reaction mixture was cooled to 0° C. and quenched with saturated aqueous sodium carbonate solution (1 mL). The resulting mixture was filtered, and the filtrate was concentrated in vacuo. The residue was purified by silica gel column chromatography (PE/EtOAc (v/v)=2/1) to give the title compound as a white solid (343 mg, 80%). The compound was characterized by the following spectroscopic data: LC-MS (ESI, pos. ion) m/z: 215.2 [M+H]+ and ¹H NMR (CDCl₃, 400 MHz) δ (ppm): 7.96 (d, J=0.8 Hz, 1H), 7.46-7.44 (m, 1H), 7.34 (dd, J=8.4, 1.4 Hz, 1H), 7.20 (s, 1H), 4.58 (s, 1H), 3.59 (t, J=6.5 Hz, 2H), 2.79 (t, J=7.5 Hz, 2H), 1.79-1.73 (m, 2H), 1.65-1.60 (m, 2H).

Step 3) 4-(5-cyano-1H-indol-3-yl)butyl 4-methylbenzenesulfonate

The title compound was prepared by the procedure described in step 4 of example 1, using 3-(4-hydroxybutyl)-1H-indole-5-carbonitrile (0.41 g, 1.9 mmol), TEA (0.3 mL, 2.28 mmol) and TsCl (0.43 g, 2.28 mmol) in DCM (20 mL) to give the crude product, which was purified by silica gel column chromatography (PE/EtOAc (v/v)=4/1) to give the title compound as a white solid (0.56 g, 80.0%). The compound was characterized by the following spectroscopic data: LC-MS (ESI, pos. ion) m/z: 369.2 [M+H]+.

Step 4) 3-(4-(4-(4,6-dimethoxypyrimidin-2-yl)piperazin-1-yl)butyl)-1H-indole-5-carbonitrile The title compound was prepared by the procedure described in step 6 of example 1, using 4-(5-cyano-1H-indol-3-yl)butyl 4-methylbenzenesulfonate (214 mg, 0.58 mmol), 4,6-dimethoxy-2-(piperazin-1-yl)pyrimidine (130 mg, 0.58 mmol), potassium carbonate (120 mg, 0.87 mmol) and potassium iodide (20 mg, 0.12 mmol) in acetonitrile (15 mL) to give the title compound as a white solid (163 mg, 67.0%). The compound was characterized by the following spectroscopic data: LC-MS (ESI, pos. ion) m/z: 421.3 [M+H]+ and ¹H NMR (CDCl₃, 400 MHz) δ (ppm): 8.34 (br s, 1H), 7.95 (s, 1H), 7.42-7.38 (m, 2H), 7.10 (s, 1H), 5.36 (s, 1H), 3.85 (s, 6H), 3.81 (t, J=4.9 Hz, 4H), 2.78 (t, J=7.4 Hz, 2H), 2.48 (t, J=5.0 Hz, 4H), 2.43 (t, J=7.6 Hz, 2H), 1.75-1.72 (m, 2H), 1.64-1.62 (m, 2H).

Example 6 3-(3-(4-(4,6-Dimethoxypyrimidin-2-yl)piperazin-1-yl)propyl)-1H-indole

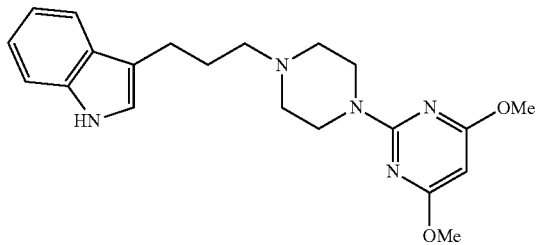 [SMILES: COc1cc(OC)nc(N2CCN(CCCc3c[nH]c4ccccc34)CC2)n1]

Step 1) 3-(1H-indol-3-yl)propan-1-ol

To a solution of phenylhydrazine (2.25 g, 20.8 mmol) in a mixture of dilute sulphuric acid (4%, 50 mL) and N,N-dimethylacetamide (10 mL) was added 3,4-dihydro-2H-pyran (1.9 mL, 20.8 mmol) dropwise at 100° C. The reaction mixture was stirred at 100° C. for 20 hours. Then the reaction mixture was cooled to rt and extracted with EtOAc (50 mL×3). The combined organic phases were washed with water (50 mL×3), dried over anhydrous Na₂SO₄, filtered and concentrated in vacuo. The residue was purified by silica gel column chromatography (PE/EtOAc (v/v)=2/1) to give the title compound as a white solid (2.29 g, 63%). The compound was characterized by the following spectroscopic data: LC-MS (ESI, pos. ion) m/z: 176.3 [M+H]+ and ¹H NMR (CDCl₃, 400 MHz) δ (ppm): 8.02 (br s, 1H), 7.60 (d, J=7.8 Hz, 1H), 7.32 (d, J=8.1 Hz, 1H), 7.20-7.16 (m, 1H), 7.13-7.09 (m, 1H), 6.95 (t, J=1.0 Hz, 1H), 3.71 (t, J=6.4 Hz, 2H), 2.84 (t, J=7.4 Hz, 2H), 2.00-1.94 (m, 2H).

Step 2) 3-(1H-indol-3-yl)propyl 4-methylbenzenesulfonate

The title compound was prepared by the procedure described in step 4 of example 1, using 3-(1H-indol-3-yl)propan-1-ol (0.88 g, 5.0 mmol), TEA (0.8 mL, 6.0 mmol) and TsCl (1.14 g, 6.0 mmol) in DCM (20 mL) to give the crude product, which was purified by silica gel column chromatography (PE/EtOAc (v/v)=4/1) to give the title compound as a white solid (1.04 g, 63%). The compound was characterized by the following spectroscopic data: LC-MS (ESI, pos. ion) m/z: 330.2 [M+H]+.

Step 3) 3-(3-(4-(4,6-dimethoxypyrimidin-2-yl)piperazin-1-yl)propyl)-1H-indole The title compound was prepared by the procedure described in step 6 of example 1, using 3-(1H-indol-3-yl)propyl 4-methylbenzenesulfonate (191 mg, 0.58 mmol), 4,6-dimethoxy-2-(piperazin-1-yl)pyrimidine (130 mg, 0.58 mmol), potassium carbonate (120 mg, 0.87 mmol) and potassium iodide (20 mg, 0.12 mmol) in acetonitrile (15 mL) to give the title compound as a white solid (155 mg, 70%). The compound was characterized by the following spectroscopic data: LC-MS (ESI, pos. ion) m/z: 382.2 [M+H]+ and ¹H NMR (CDCl₃, 400 MHz) δ (ppm): 7.99 (br s, 1H), 7.62 (d, J=7.8 Hz, 1H), 7.35 (d, J=8.0 Hz, 1H), 7.19 (t, J=7.5 Hz, 1H), 7.11 (t, J=7.4 Hz, 1H), 6.99 (s, 1H), 5.36 (s, 1H), 3.85 (s, 6H), 3.82 (t, J=4.7 Hz, 4H), 2.81 (t, J=7.5 Hz, 2H), 2.50-2.46 (m, 6H), 1.98-1.92 (m, 2H).

Example 7 3-(3-(4-(4,6-Dimethoxypyrimidin-2-yl)piperazin-1-yl)propyl)-5-methoxy-1H-indole

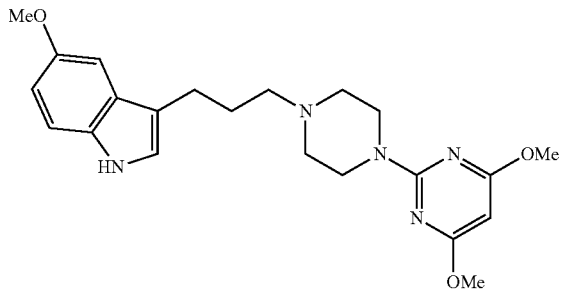 [SMILES: COc1ccc2[nH]cc(CCCN3CCN(c4nc(OC)cc(OC)n4)CC3)c2c1]

Step 1) 3-(5-methoxy-1H-indol-3-yl)propan-1-ol

The title compound was prepared by the procedure described in step 1 of example 6, using 4-methoxyphenylhydrazine hydrochloride (3.63 g, 20.8 mmol) and 3,4-dihydro-2H-pyran (1.9 mL, 20.8 mmol) in a mixture of dilute sulphuric acid (4%, 50 mL) and N,N-dimethylacetamide (10 mL) to give the crude product, which was purified by silica gel column chromatography (PE/EtOAc (v/v)=2/1) to give the title compound as a white solid (1.5 g, 35%). The compound was characterized by the following spectroscopic data: LC-MS (ESI, pos. ion) m/z: 206.0 [M+H]$^+$.

Step 2) 3-(5-methoxy-1H-indol-3-yl)propyl 4-methylbenzenesulfonate

The title compound was prepared by the procedure described in step 4 of example 1, using 3-(5-methoxy-1H-indol-3-yl)propan-1-ol (1.03 g, 5.0 mmol), TEA (0.8 mL, 6.0 mmol) and TsCl (1.14 g, 6.0 mmol) in DCM (20 mL) to give the crude product, which was purified by silica gel column chromatography (PE/EtOAc (v/v)=4/1) to give the title compound as a white solid (1.26 g, 70.%). The compound was characterized by the following spectroscopic data: LC-MS (ESI, pos. ion) m/z: 360.1 [M+H]$^+$.

Step 3) 3-(3-(4-(4,6-dimethoxypyrimidin-2-yl)piperazin-1-yl)propyl)-5-methoxy-1H-indole The title compound was prepared by the procedure described in step 6 of example 1, using 3-(5-methoxy-1H-indol-3-yl)propyl 4-methylbenzenesulfonate (208 mg, 0.58 mmol), 4,6-dimethoxy-2-(piperazin-1-yl)pyrimidine (130 mg, 0.58 mmol), potassium carbonate (120 mg, 0.87 mmol) and potassium iodide (20 mg, 0.12 mmol) in acetonitrile (15 mL) to give the title compound as a white solid (167 mg, 70.0%). The compound was characterized by the following spectroscopic data: LC-MS (ESI, pos. ion) m/z: 412.2 [M+H]$^+$ and $^1$H NMR (CDCl$_3$, 400 MHz) δ (ppm): 7.96 (br s, 1H), 7.26-7.24 (m, 1H), 7.03-7.01 (m, 2H), 6.86 (dd, J=8.7, 2.2 Hz, 1H), 5.39 (s, 1H), 3.95 (t, J=4.5 Hz, 4H), 3.87 (s, 3H), 3.85 (s, 6H), 2.79 (t, J=7.3 Hz, 2H), 2.67-2.61 (m, 6H), 2.09-2.05 (m, 2H).

Example 8 5-Chloro-3-(3-(4-(4,6-dimethoxypyrimidin-2-yl)piperazin-1-yl)propyl)-1H-indole

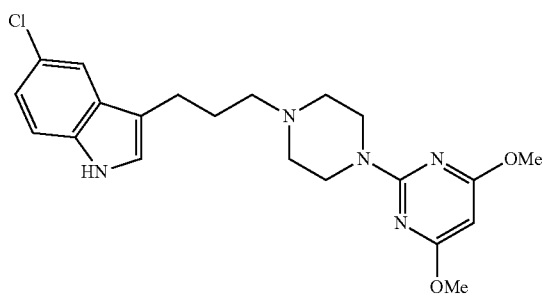 [SMILES: COc1cc(OC)nc(N2CCN(CCCc3c[nH]c4ccc(Cl)cc34)CC2)n1]

Step 1) 3-(5-chloro-1H-indol-3-yl)propan-1-ol

The title compound was prepared by the procedure described in step 1 of example 6, using 4-chlorophenylhydrazine hydrochloride (3.72 g, 20.8 mmol) and 3,4-dihydro-2H-pyran (1.9 mL, 20.8 mmol) in a mixture of dilute sulphuric acid (4%, 50 mL) and N,N-dimethylacetamide (10 mL) to give the crude product, which was purified by silica gel column chromatography (PE/EtOAc (v/v)=2/1) to give the title compound as a white solid (2.35 g, 54%). The compound was characterized by the following spectroscopic data: LC-MS (ESI, pos. ion) m/z: 210.2 [M+H]$^+$ and $^1$H NMR (CDCl$_3$, 400 MHz) δ (ppm): 8.10 (br s, 1H), 7.56 (d, J=1.8 Hz, 1H), 7.26-7.24 (m, 2H), 7.11 (dd, J=8.6, 1.9 Hz, 1H), 6.99 (s, 1H), 3.71 (t, J=6.4 Hz, 2H), 2.80 (t, J=7.5 Hz, 2H), 1.99-1.92 (m, 2H).

Step 2) 3-(5-chloro-1H-indol-3-yl)propyl 4-methylbenzenesulfonate

The title compound was prepared by the procedure described in step 4 of example 1, using 3-(5-chloro-1H-indol-3-yl)propan-1-ol (1.05 g, 5.0 mmol), TEA (0.8 mL, 6.0 mmol) and TsCl (1.14 g, 6.0 mmol) in DCM (20 mL) to give the crude product, which was purified by silica gel column chromatography (PE/EtOAc (v/v)=4/1) to give the title compound as a white solid (1.09 g, 60%). The compound was characterized by the following spectroscopic data: LC-MS (ESI, pos. ion) m/z: 364.1 [M+H]$^+$.

Step 3) 5-chloro-3-(3-(4-(4,6-dimethoxypyrimidin-2-yl)piperazin-1-yl)propyl)-1H-indole The title compound was prepared by the procedure described in step 6 of example 1, using 3-(5-chloro-1H-indol-3-yl)propyl 4-methylbenzenesulfonate (0.21 g, 0.58 mmol), 4,6-dimethoxy-2-(piperazin-1-yl)pyrimidine (0.13 g, 0.58 mmol), potassium carbonate (0.12 g, 0.87 mmol) and potassium iodide (20 mg, 0.12 mmol) in acetonitrile (15 mL) to give the title compound as a white solid (159 mg, 66%). The compound was characterized by the following spectroscopic data: LC-MS (ESI, pos. ion) m/z: 416.1 [M+H]$^+$ and $^1$H NMR (CDCl$_3$, 400 MHz) δ (ppm): 8.05 (br s, 1H), 7.59 (d, J=1.6 Hz, 1H), 7.27-7.25 (m, 1H), 7.13 (dd, J=8.6, 1.8 Hz, 1H), 7.01 (d, J=1.7 Hz, 1H), 5.36 (s, 1H), 3.85 (s, 6H), 3.83 (t, J=5.1 Hz, 4H), 2.76 (t, J=7.5 Hz, 2H), 2.48 (t, J=5.2 Hz, 4H), 2.45-2.43 (m, 2H), 1.96-1.89 (m, 2H).

Example 9 3-(3-(4-(4,6-Dimethoxypyrimidin-2-yl)piperazin-1-yl)propyl)-5-fluoro-1H-indole

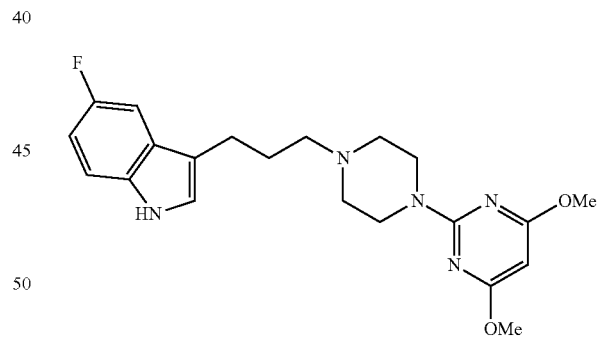

Step 1) 3-(5-fluoro-1H-indol-3-yl)propan-1-ol

The title compound was prepared by the procedure described in step 1 of example 6, using 4-fluorophenylhydrazine hydrochloride (3.38 g, 20.8 mmol) and 3,4-dihydro-2H-pyran (1.9 mL, 20.8 mmol) in a mixture of dilute sulphuric acid (4%, 50 mL) and N,N-dimethylacetamide (10 mL) to give the crude product, which was purified by silica gel column chromatography (PE/EtOAc (v/v)=2/1) to give the title compound as a white solid (3.53 g, 88%). The compound was characterized by the following spectroscopic data: LC-MS (ESI, pos. ion) m/z: 194.2 [M+H]$^+$ and $^1$H NMR (CDCl$_3$, 400 MHz) δ (ppm): 8.05 (br s, 1H), 7.27-7.23

(m, 1H), 7.03 (d, J=2.0 Hz, 1H), 6.96-6.91 (m, 1H), 3.72 (t, J=6.4 Hz, 2H), 2.81 (t, J=7.5 Hz, 2H), 2.00-1.93 (m, 2H).

Step 2) 3-(5-fluoro-1H-indol-3-yl)propyl 4-methylbenzenesulfonate

The title compound was prepared by the procedure described in step 4 of example 1, using 3-(5-fluoro-1H-indol-3-yl)propan-1-ol (0.97 g, 5.0 mmol), TEA (0.8 mL, 6.0 mmol) and TsCl (1.14 g, 6.0 mmol) in DCM (20 mL) to give the crude product, which was purified by silica gel column chromatography (PE/EtOAc (v/v)=4/1) to give the title compound as a white solid (1.28 g, 74%). The compound was characterized by the following spectroscopic data: LC-MS (ESI, pos. ion) m/z: 348.1 [M+H]$^+$.

Step 3) 3-(3-(4-(4,6-dimethoxypyrimidin-2-yl)piperazin-1-yl)propyl)-5-fluoro-1H-indole The title compound was prepared by the procedure described in step 6 of example 1, using 3-(5-fluoro-1H-indol-3-yl)propyl 4-methylbenzenesulfonate (201 mg, 0.58 mmol), 4,6-dimethoxy-2-(piperazin-1-yl)pyrimidine (130 mg, 0.58 mmol), potassium carbonate (120 mg, 0.87 mmol) and potassium iodide (20 mg, 0.12 mmol) in acetonitrile (15 mL) to give the title compound as a white solid (180 mg, 78%). The compound was characterized by the following spectroscopic data: LC-MS (ESI, pos. ion) m/z: 400.2 [M+H]$^+$ and $^1$H NMR (CDCl$_3$, 400 MHz) δ (ppm): 8.03 (br s, 1H), 7.25-7.24 (m, 2H), 7.03 (d, J=1.8 Hz, 1H), 6.93 (td, J=9.1, 2.4 Hz, 1H), 5.36 (s, 1H), 3.85 (s, 6H), 3.82 (t, J=5.0 Hz, 4H), 2.76 (t, J=7.5 Hz, 2H), 2.50-2.44 (m, 6H), 1.95-1.77 (m, 2H).

Example 10 3-(3-(4-(4,6-Dimethoxypyrimidin-2-yl)piperazin-1-yl)propyl)-1H-indole-5-carbonitrile

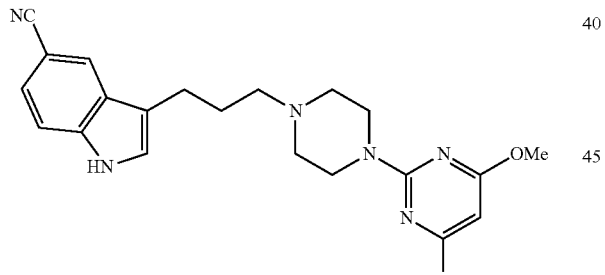

Step 1) 3-(3-hydroxypropyl)-1H-indole-5-carbonitrile

The title compound was prepared by the procedure described in step 1 of example 6, using 4-cyanophenylhydrazine hydrochloride (3.53 g, 20.8 mmol) and 3,4-dihydro-2H-pyran (1.9 mL, 20.8 mmol) in a mixture of dilute sulphuric acid (4%, 50 mL) and N,N-dimethylacetamide (10 mL) to give the crude product, which was purified by silica gel column chromatography (PE/EtOAc (v/v)=2/1) to give the title compound as a white solid (1.46 g, 35%). The compound was characterized by the following spectroscopic data: LC-MS (ESI, pos. ion) m/z: 201.1 [M+H]$^+$ and $^1$H NMR (DMSO-d$_6$, 400 MHz) δ (ppm): 11.36 (s, 1H), 7.50-7.48 (m, 1H), 7.38 (dd, J=8.4, 1.5 Hz, 1H), 7.31 (d, J=2.0 Hz, 1H), 4.46 (t, J=5.1, 1H), 3.47-3.43 (m, 2H), 2.74 (d, J=7.6 Hz, 2H), 1.81-1.74 (m, 2H).

Step 2) 3-(5-cyano-1H-indol-3-yl)propyl 4-methylbenzenesulfonate

The title compound was prepared by the procedure described in step 4 of example 1, using 3-(3-hydroxypropyl)-1H-indole-5-carbonitrile (1.00 g, 5.0 mmol), TEA (0.8 mL, 6.0 mmol) and TsCl (1.14 g, 6.0 mmol) in DCM (20 mL) to give the crude product, which was purified by silica gel column chromatography (PE/EtOAc (v/v)=4/1) to give the title compound as a white solid (1.33 g, 75%). The compound was characterized by the following spectroscopic data: LC-MS (ESI, pos. ion) m/z: 355.1 [M+H]$^+$ and $^1$H NMR (CDCl$_3$, 400 MHz) δ (ppm): 8.51 (br s, 1H), 7.83 (s, 1H), 7.77 (d, J=8.3 Hz, 2H), 7.40 (s, 2H), 7.33 (d, J=8.1 Hz, 2H), 7.08 (d, J=2.2 Hz, 1H), 4.08 (t, J=6.1 Hz, 2H), 2.81 (t, J=7.3 Hz, 2H), 2.45 (s, 3H), 2.06-1.99 (m, 2H).

Step 3) 3-(3-(4-(4,6-dimethoxypyrimidin-2-yl)piperazin-1-yl)propyl)-1H-indole-5-carbonitrile The title compound was prepared by the procedure described in step 6 of example 1, using 3-(5-cyano-1H-indol-3-yl)propyl 4-methylbenzenesulfonate (206 mg, 0.58 mmol), 4,6-dimethoxy-2-(piperazin-1-yl)pyrimidine (130 mg, 0.58 mmol), potassium carbonate (120 mg, 0.87 mmol) and potassium iodide (20 mg, 0.12 mmol) in acetonitrile (15 mL) to give the title compound as a white solid (155 mg, 66%). The compound was characterized by the following spectroscopic data: LC-MS (ESI, pos. ion) m/z: 407.5 [M+H]$^+$ and $^1$H NMR (CDCl$_3$, 400 MHz) δ (ppm): 8.33 (br s, 1H), 7.98 (s, 1H), 7.41-7.38 (m, 2H), 7.12 (s, 1H), 5.36 (s, 1H), 3.85 (s, 6H), 3.83 (t, J=5.0 Hz, 4H), 2.81 (t, J=7.5 Hz, 2H), 2.48 (t, J=4.9 Hz, 4H), 2.45-2.44 (m, 2H), 1.96-1.92 (m, 2H).

Example 11 3-(4-(4-(4,6-Dimethylpyrimidin-2-yl)piperazin-1-yl)butyl)-1H-indole

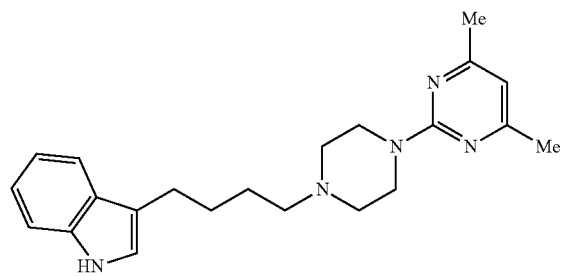 [SMILES: Cc1cc(C)nc(N2CCN(CCCCc3c[nH]c4ccccc34)CC2)n1]

Step 1) 4,6-dimethyl-2-(piperazin-1-yl)pyrimidine

The title compound was prepared by the procedure described in step 5 of example 1, using 2-chloro-4,6-dimethylpyrimidine (1.03 g, 7.2 mmol), potassium carbonate (1.00 g, 7.2 mmol) and anhydrous piperazine (1.24 g, 14.4 mmol) in DMF (10 mL) to give the title compound as a white solid (0.80 g, 58%). The compound was characterized by the following spectroscopic data: LC-MS (ESI, pos. ion)

m/z: 193.3 [M+H]⁺ and ¹H NMR (CDCl₃, 400 MHz) δ (ppm): 6.26 (s, 1H), 3.80 (t, J=5.1 Hz, 4H), 2.92 (t, J=5.1 Hz, 4H), 2.28 (s, 6H).

Step 2) 3-(4-(4-(4,6-dimethylpyrimidin-2-yl)piperazin-1-yl)butyl)-1H-indole

The title compound was prepared by the procedure described in step 6 of example 1, using 4-(1H-indol-3-yl)butyl 4-methylbenzenesulfonate (200 mg, 0.58 mmol), 4,6-dimethyl-2-(piperazin-1-yl)pyrimidine (112 mg, 0.58 mmol), potassium carbonate (120 mg, 0.87 mmol) and potassium iodide (20 mg, 0.12 mmol) in acetonitrile (15 mL) to give the title compound as a white solid (126 mg, 60%). The compound was characterized by the following spectroscopic data: LC-MS (ESI, pos. ion) m/z: 364.3 [M+H]⁺ and ¹H NMR (CDCl₃, 400 MHz) δ (ppm): 7.97 (br s, 1H), 7.61 (d, J=7.8 Hz, 1H), 7.35 (d, J=8.0 Hz, 1H), 7.20-7.16 (m, 1H), 7.12-7.09 (m, 1H), 6.98 (d, J=1.7 Hz, 1H), 6.26 (s, 1H), 3.84 (t, J=4.9 Hz, 4H), 2.79 (d, J=7.4 Hz, 2H), 2.49 (t, J=5.0 Hz, 4H), 2.42 (t, J=7.6 Hz, 2H), 2.28 (s, 6H), 1.79-1.72 (m, 2H), 1.68-1.62 (m, 2H).

Example 12 3-(4-(4-(4,6-Dimethylpyrimidin-2-yl)piperazin-1-yl)butyl)-5-methoxy-1H-indole

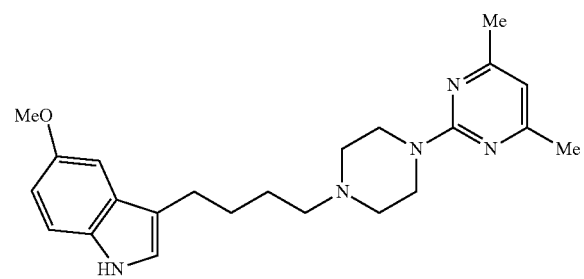 [SMILES: COc1ccc2[nH]cc(CCCCN3CCN(c4nc(C)cc(C)n4)CC3)c2c1]

The title compound was prepared by the procedure described in step 6 of example 1, using 4-(5-methoxy-1H-indol-3-yl)butyl 4-methylbenzenesulfonate (216 mg, 0.58 mmol), 4,6-dimethyl-2-(piperazin-1-yl)pyrimidine (112 mg, 0.58 mmol), potassium carbonate (120 mg, 0.87 mmol) and potassium iodide (20 mg, 0.12 mmol) in acetonitrile (15 mL) to give the title compound as a white solid (114 mg, 50%). The compound was characterized by the following spectroscopic data: LC-MS (ESI, pos. ion) m/z: 394.3 [M+H]⁺ and ¹H NMR (CDCl₃, 400 MHz) δ (ppm): 7.92 (br s, 1H), 7.26-7.22 (m, 1H), 7.03 (d, J=1.8 Hz, 1H), 6.96 (s, 1H), 6.86 (dd, J=8.7, 2.1 Hz, 1H), 6.26 (s, 1H), 3.87 (s, 3H), 3.84 (d, J=4.6 Hz, 4H), 2.79 (s, 6H), 2.75 (t, J=7.2 Hz, 2H), 2.49 (t, J=4.7 Hz, 4H), 2.43 (t, J=7.5 Hz, 2H), 1.76-1.68 (m, 2H), 1.66-1.63 (m, 2H).

Example 13 5-Chloro-3-(4-(4-(4,6-dimethylpyrimidin-2-yl)piperazin-1-yl)butyl)-1H-indole

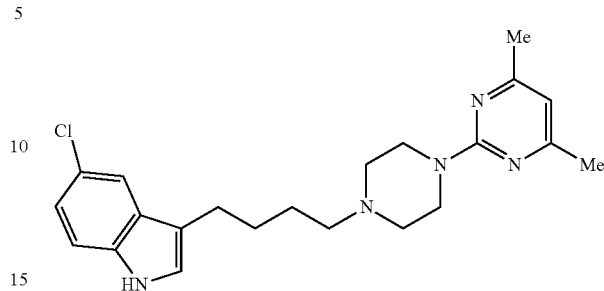

The title compound was prepared by the procedure described in step 6 of example 1, using 4-(5-chloro-1H-indol-3-yl)butyl 4-methylbenzenesulfonate (219 mg, 0.58 mmol), 4,6-dimethyl-2-(piperazin-1-yl)pyrimidine (112 mg, 0.58 mmol), potassium carbonate (120 mg, 0.87 mmol) and potassium iodide (20 mg, 0.12 mmol) in acetonitrile (15 mL) to give the title compound as a white solid (145 mg, 63%). The compound was characterized by the following spectroscopic data: LC-MS (ESI, pos. ion) m/z: 398.2 [M+H]⁺ and ¹H NMR (CDCl₃, 400 MHz) δ (ppm): 7.99 (br s, 1H), 7.56 (d, J=1.9 Hz, 1H), 7.27-7.25 (m, 1H), 7.13 (dd, J=8.6, 2.1 Hz, 1H), 7.00 (d, J=2.1 Hz, 1H), 6.26 (s, 1H), 3.84 (t, J=5.0 Hz, 4H), 2.74 (t, J=7.3 Hz, 2H), 2.49 (t, J=5.1 Hz, 4H), 2.42 (t, J=7.6 Hz, 2H), 2.28 (s, 6H), 1.73-1.71 (m, 2H), 1.65-1.60 (m, 2H).

Example 14 3-(4-(4-(4,6-Dimethylpyrimidin-2-yl)piperazin-1-yl)butyl)-5-fluoro-1H-indole

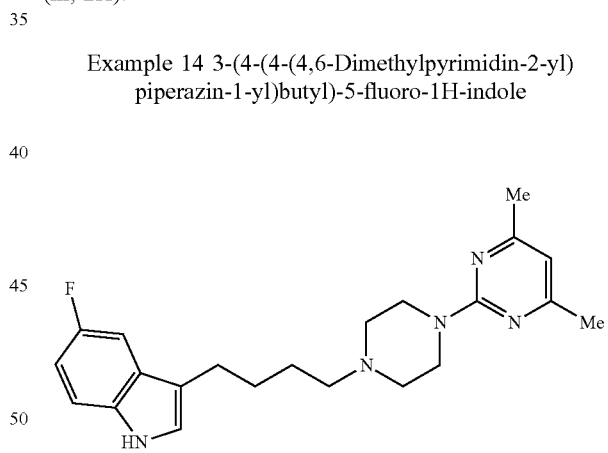

The title compound was prepared by the procedure described in step 6 of example 1, using 4-(5-fluoro-1H-indol-3-yl)butyl 4-methylbenzenesulfonate (210 mg, 0.58 mmol), 4,6-dimethyl-2-(piperazin-1-yl)pyrimidine (112 mg, 0.58 mmol), potassium carbonate (120 mg, 0.87 mmol) and potassium iodide (20 mg, 0.12 mmol) in acetonitrile (15 mL) to give the title compound as a white solid (177 mg, 80.0%). The compound was characterized by the following spectroscopic data: LC-MS (ESI, pos. ion) m/z: 382.3 [M+H]⁺ and ¹H NMR (CDCl₃, 400 MHz) δ (ppm): 7.96 (br s, 1H), 7.25-7.22 (m, 2H), 7.02 (s, 1H), 6.92 (d, J=9.0, 2.4 Hz, 1H), 6.26 (s, 1H), 3.83 (t, J=4.8 Hz, 4H), 2.74 (t, J=7.3 Hz, 2H), 2.48 (t, J=5.0 Hz, 4H), 2.41 (t, J=7.6 Hz, 2H), 2.28 (s, 6H), 1.77-1.71 (m, 2H), 1.65-1.59 (m, 2H).

Example 15 3-(4-(4-(4,6-Dimethylpyrimidin-2-yl)piperazin-1-yl)butyl)-1H-indole-5-carbonitrile

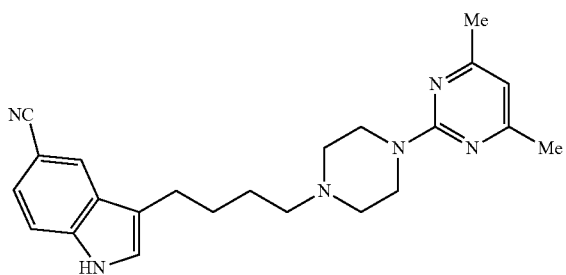 [SMILES: Cc1cc(C)nc(N2CCN(CCCCc3c[nH]c4ccc(C#N)cc34)CC2)n1]

The title compound was prepared by the procedure described in step 6 of example 1, using 4-(5-cyano-1H-indol-3-yl)butyl 4-methylbenzenesulfonate (214 mg, 0.58 mmol), 4,6-dimethyl-2-(piperazin-1-yl)pyrimidine (112 mg, 0.58 mmol), potassium carbonate (120 mg, 0.87 mmol) and potassium iodide (20 mg, 0.12 mmol) in acetonitrile (15 mL) to give the title compound as a white solid (148 mg, 66%). The compound was characterized by the following spectroscopic data: LC-MS (ESI, pos. ion) m/z: 389.3 [M+H]$^+$ and $^1$H NMR (CDCl$_3$, 400 MHz) δ (ppm): 8.31 (br s, 1H), 7.95 (s, 1H), 7.43-7.37 (m, 2H), 7.10 (s, 1H), 6.26 (s, 1H), 3.83 (t, J=4.9 Hz, 4H), 2.79-2.77 (m, 2H), 2.48 (t, J=5.0 Hz, 4H), 2.42-2.39 (m, 2H), 2.28 (s, 6H), 1.76-1.72 (m, 2H), 1.66-1.63 (m, 2H).

Example 16 3-(3-(4-(4,6-Dimethylpyrimidin-2-yl)piperazin-1-yl)propyl)-1H-indole

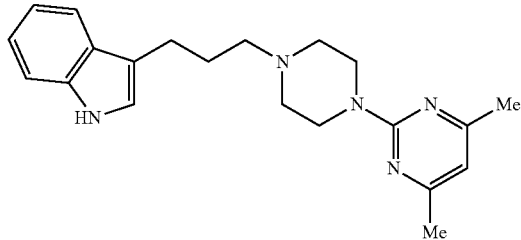 [SMILES: Cc1cc(C)nc(N2CCN(CCCc3c[nH]c4ccccc34)CC2)n1]

The title compound was prepared by the procedure described in step 6 of example 1, using 3-(1H-indol-3-yl)propyl 4-methylbenzenesulfonate (191 mg, 0.58 mmol), 4,6-dimethyl-2-(piperazin-1-yl)pyrimidine (112 mg, 0.58 mmol), potassium carbonate (120 mg, 0.87 mmol) and potassium iodide (20 mg, 0.12 mmol) in acetonitrile (15 mL) to give the title compound as a white solid (167 mg, 82%). The compound was characterized by the following spectroscopic data: LC-MS (ESI, pos. ion) m/z: 350.2 [M+H]$^+$ and $^1$H NMR (CDCl$_3$, 400 MHz) δ (ppm): 7.98 (br s, 1H), 7.62 (d, J=7.8 Hz, 1H), 7.36 (d, J=8.0 Hz, 1H), 7.19 (t, J=7.2 Hz, 1H), 7.11 (t, J=7.2 Hz, 1H), 7.00 (d, J=2.0 Hz, 1H), 6.26 (s, 1H), 3.85 (t, J=4.9 Hz, 4H), 2.81 (t, J=7.6 Hz, 2H), 2.52-2.47 (m, 6H), 2.28 (s, 6H), 1.99-1.93 (m, 2H).

Example 17 3-(3-(4-(4,6-Dimethylpyrimidin-2-yl)piperazin-1-yl)propyl)-5-methoxy-1H-indole

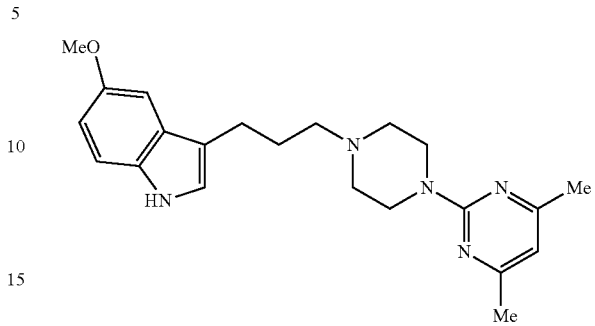

The title compound was prepared by the procedure described in step 6 of example 1, using 3-(5-methoxy-1H-indol-3-yl)propyl 4-methylbenzenesulfonate (208 mg, 0.58 mmol), 4,6-dimethyl-2-(piperazin-1-yl)pyrimidine (112 mg, 0.58 mmol), potassium carbonate (120 mg, 0.87 mmol) and potassium iodide (20 mg, 0.12 mmol) in acetonitrile (15 mL) to give the title compound as a white solid (132 mg, 60.0%). The compound was characterized by the following spectroscopic data: LC-MS (ESI, pos. ion) m/z: 380.3 [M+H]$^+$ and $^1$H NMR (CDCl$_3$, 400 MHz) δ (ppm): 8.03 (br s, 1H), 7.22 (d, J=8.6 Hz, 1H), 7.04 (s, 1H), 6.95 (s, 1H), 6.84 (d, J=8.2 Hz, 1H), 6.26 (s, 1H), 3.86 (s, 3H), 3.83 (t, J=4.9 Hz, 4H), 2.76 (t, J=6.8 Hz, 2H), 2.51 (t, J=5.1 Hz, 4H), 2.46 (d, J=7.6 Hz, 2H), 2.28 (s, 6H), 1.97-1.90 (m, 2H).

Example 18 5-Chloro-3-(3-(4-(4,6-dimethylpyrimidin-2-yl)piperazin-1-yl)propyl)-1H-indole

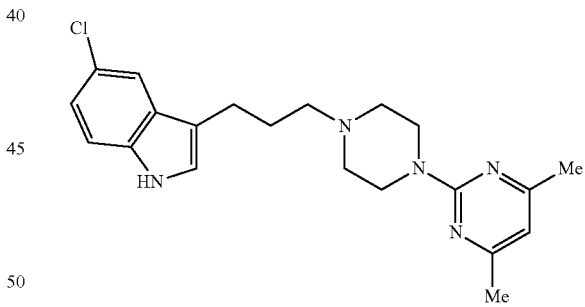

The title compound was prepared by the procedure described in step 6 of example 1, using 3-(5-chloro-1H-indol-3-yl)propyl 4-methylbenzenesulfonate (211 mg, 0.58 mmol), 4,6-dimethyl-2-(piperazin-1-yl)pyrimidine (112 mg, 0.58 mmol), potassium carbonate (120 mg, 0.87 mmol) and potassium iodide (20 mg, 0.12 mmol) in acetonitrile (15 mL) to give the title compound as a white solid (144 mg, 65%). The compound was characterized by the following spectroscopic data: LC-MS (ESI, pos. ion) m/z: 384.2 [M+H]$^+$ and $^1$H NMR (CDCl$_3$, 400 MHz) δ (ppm): 8.01 (br s, 1H), 7.59 (d, J=1.8 Hz, 1H), 7.27-7.25 (m, 1H), 7.13 (dd, J=8.6, 2.0 Hz, 1H), 7.02 (d, J=2.0 Hz, 1H), 6.26 (s, 1H), 3.86 (t, J=5.0 Hz, 4H), 2.76 (t, J=7.5 Hz, 2H), 2.50 (t, J=5.1 Hz, 4H), 2.46 (d, J=7.6 Hz, 2H), 2.28 (s, 6H), 1.97-1.90 (m, 2H).

Example 19 3-(3-(4-(4,6-Dimethylpyrimidin-2-yl)piperazin-1-yl)propyl)-5-fluoro-1H-indole

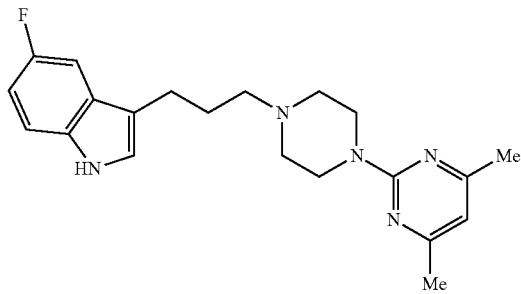 [SMILES: Cc1cc(C)nc(N2CCN(CCCc3c[nH]c4ccc(F)cc34)CC2)n1]

The title compound was prepared by the procedure described in step 6 of example 1, using 3-(5-fluoro-1H-indol-3-yl)propyl 4-methylbenzenesulfonate (201 mg, 0.58 mmol), 4,6-dimethyl-2-(piperazin-1-yl)pyrimidine (112 mg, 0.58 mmol), potassium carbonate (120 mg, 0.87 mmol) and potassium iodide (20 mg, 0.12 mmol) in acetonitrile (15 mL) to give the title compound as a white solid (170 mg, 80%). The compound was characterized by the following spectroscopic data: LC-MS (ESI, pos. ion) m/z: 368.2 [M+H]$^+$ and $^1$H NMR (CDCl$_3$, 400 MHz) δ (ppm): 8.00 (br s, 1H), 7.26-7.24 (m, 2H), 7.04 (d, J=1.7 Hz, 1H), 6.93 (td, J=9.1, 2.4 Hz, 1H), 6.26 (s, 1H), 3.85 (t, J=4.9 Hz, 4H), 2.75 (t, J=7.5 Hz, 2H), 2.50 (t, J=5.1 Hz, 4H), 2.46 (t, J=7.7 Hz, 2H), 2.28 (s, 6H), 1.95-1.90 (m, 2H).

Example 20 3-(3-(4-(4,6-Dimethylpyrimidin-2-yl)piperazin-1-yl)propyl)-1H-indole-5-carbonitrile

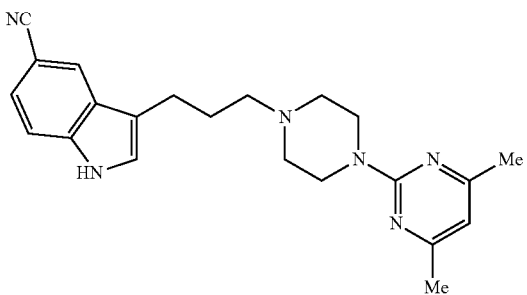 [SMILES: Cc1cc(C)nc(N2CCN(CCCc3c[nH]c4ccc(C#N)cc34)CC2)n1]

The title compound was prepared by the procedure described in step 6 of example 1, using 3-(5-cyano-1H-indol-3-yl)propyl 4-methylbenzenesulfonate (206 mg, 0.58 mmol), 4,6-dimethyl-2-(piperazin-1-yl)pyrimidine (112 mg, 0.58 mmol), potassium carbonate (120 mg, 0.87 mmol) and potassium iodide (20 mg, 0.12 mmol) in acetonitrile (15 mL) to give the title compound as a white solid (152 mg, 70.0%). The compound was characterized by the following spectroscopic data: LC-MS (ESI, pos. ion) m/z: 375.2 [M+H]$^+$ and $^1$H NMR (CDCl$_3$, 400 MHz) δ (ppm): 8.32 (br s, 1H), 7.98 (s, 1H), 7.43-7.38 (m, 2H), 7.12 (d, J=2.0 Hz, 1H), 6.27 (s, 1H), 3.86 (t, J=4.9 Hz, 4H), 2.81 (t, J=7.5 Hz, 2H), 2.51 (t, J=5.0 Hz, 4H), 2.46 (t, J=7.6 Hz, 2H), 2.28 (s, 6H), 1.99-1.91 (m, 2H).

Example 21 3-(4-(4-(4-Methoxy-6-methylpyrimidin-2-yl)piperazin-1-yl)butyl)-1H-indole-5-carbonitrile

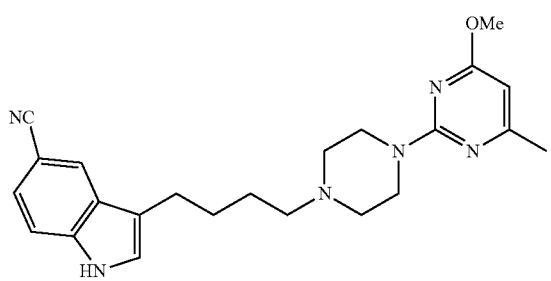 [SMILES: COc1cc(C)nc(N2CCN(CCCCc3c[nH]c4ccc(C#N)cc34)CC2)n1]

Step 1) 4-methoxy-6-methyl-2-(piperazin-1-yl)pyrimidine

The title compound was prepared by the procedure described in step 5 of example 1, using 2-chloro-4-methoxy-6-methylpyrimidine (1.14 g, 7.2 mmol), potassium carbonate (1.00 g, 7.2 mmol) and anhydrous piperazine (1.24 g, 14.4 mmol) in DMF (10 mL) to give the title compound as a white solid (0.75 g, 50.0%). The compound was characterized by the following spectroscopic data: LC-MS (ESI, pos. ion) m/z: 209.2 [M+H]$^+$ and $^1$H NMR (CDCl$_3$, 400 MHz) δ (ppm): 5.84 (s, 1H), 3.85 (s, 3H), 3.79 (t, J=5.1 Hz, 4H), 2.92 (t, J=5.1 Hz, 4H), 2.46 (s, 3H).

Step 2) 3-(4-(4-(4-methoxy-6-methylpyrimidin-2-yl)piperazin-1-yl)butyl)-1H-indole-5-carbonitrile The title compound was prepared by the procedure described in step 6 of example 1, using 4-(5-cyano-1H-indol-3-yl)butyl 4-methylbenzenesulfonate (214 mg, 0.58 mmol), 4-methoxy-6-methyl-2-(piperazin-1-yl)pyrimidine (121 mg, 0.58 mmol), potassium carbonate (120 mg, 0.87 mmol) and potassium iodide (20 mg, 0.12 mmol) in acetonitrile (15 mL) to give the title compound as a white solid (147 mg, 63%). The compound was characterized by the following spectroscopic data: LC-MS (ESI, pos. ion) m/z: 405.3 [M+H]$^+$ and $^1$H NMR (CDCl$_3$, 400 MHz) δ (ppm): 8.34 (br s, 1H), 7.95 (s, 1H), 7.40 (t, J=7.2 Hz, 2H), 7.11 (t, J=10.6 Hz, 1H), 5.85 (s, 1H), 3.86 (s, 3H), 3.84 (m, 4H), 2.79 (t, J=7.3 Hz, 2H), 2.52 (t, J=4.9 Hz, 4H), 2.46 (t, J=7.5 Hz, 2H), 2.25 (s, 3H), 1.76-1.71 (m, 2H), 1.68-1.65 (m, 2H).

Example 22 3-(3-(4-(4-Methoxy-6-methylpyrimidin-2-yl)piperazin-1-yl)propyl)-1H-indole-5-carbonitrile

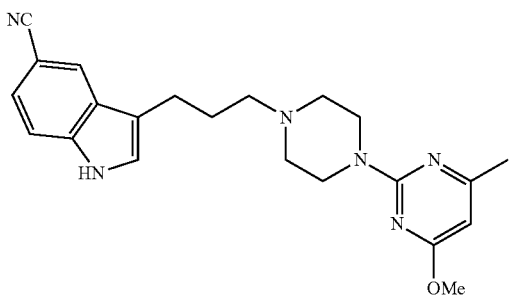 [SMILES: COc1cc(C)nc(N2CCN(CCCc3c[nH]c4ccc(C#N)cc34)CC2)n1]

The title compound was prepared by the procedure described in step 6 of example 1, using 3-(5-cyano-1H-indol-3-yl)propyl 4-methylbenzenesulfonate (206 mg, 0.58 mmol), 4-methoxy-6-methyl-2-(piperazin-1-yl)pyrimidine (121 mg, 0.58 mmol), potassium carbonate (120 mg, 0.87 mmol) and potassium iodide (20 mg, 0.12 mmol) in acetonitrile (15 mL) to give the title compound as a white solid (130 mg, 57%). The compound was characterized by the following spectroscopic data: LC-MS (ESI, pos. ion) m/z: 391.2 [M+H]$^+$ and $^1$H NMR (CDCl$_3$, 400 MHz) δ (ppm): 8.35 (br s, 1H), 7.96 (s, 1H), 7.41-7.38 (m, 2H), 7.16 (s, 1H), 5.85 (s, 1H), 4.09-4.07 (m, 4H), 3.86 (s, 3H), 2.81 (t, J=7.4 Hz, 2H), 2.56-2.50 (m, 4H), 2.25 (s, 3H), 2.04-1.97 (m, 2H), 1.28-1.24 (m, 2H).

Example 23 2-(4-(4-(5-Fluoro-1H-indol-3-yl)butyl)piperazin-1-yl)pyrimidine-4-carbonitrile

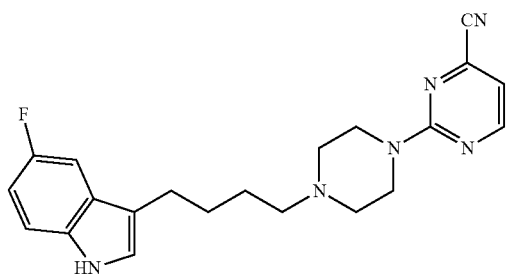 [SMILES: N#Cc1ccnc(N2CCN(CCCCc3c[nH]c4ccc(F)cc34)CC2)n1]

Step 1) 2-(piperazin-1-yl)pyrimidine-4-carbonitrile

The title compound was prepared by the procedure described in step 5 of example 1, using 2-chloro-4-cyanopyrimidine (1.00 g, 7.2 mmol), potassium carbonate (1.00 g, 7.2 mmol) and anhydrous piperazine (1.24 g, 14.4 mmol) in DMF (10 mL) to give the title compound as a yellow solid (0.81 g, 60%). The compound was characterized by the following spectroscopic data: LC-MS (ESI, pos. ion) m/z: 190.1 [M+H]$^+$ and $^1$H NMR (CDCl$_3$, 400 MHz) δ (ppm): 8.43 (d, J=4.6 Hz, 1H), 6.72 (d, J=4.6 Hz, 1H), 3.81 (t, J=5.1 Hz, 4H), 2.92 (t, J=5.1 Hz, 4H).

Step 2) 2-(4-(4-(5-fluoro-1H-indol-3-yl)butyl)piperazin-1-yl)pyrimidine-4-carbonitrile The title compound was prepared by the procedure described in step 6 of example 1, using 4-(5-fluoro-1H-indol-3-yl)butyl 4-methylbenzenesulfonate (210 mg, 0.58 mmol), 2-(piperazin-1-yl)pyrimidine-4-carbonitrile (110 mg, 0.58 mmol), potassium carbonate (120 mg, 0.87 mmol) and potassium iodide (20 mg, 0.12 mmol) in acetonitrile (15 mL) to give the title compound as a white solid (186 mg, 85%). The compound was characterized by the following spectroscopic data: LC-MS (ESI, pos. ion) m/z: 379.3 [M+H]$^+$ and $^1$H NMR (CDCl$_3$, 400 MHz) δ (ppm): 8.45 (d, J=4.7 Hz, 1H), 7.97 (s, 1H), 7.30-7.28 (m, 2H), 7.05 (d, J=1.0 Hz, 1H), 6.95 (d, J=9.0, 2.5 Hz, 1H), 6.75 (d, J=4.7 Hz, 1H), 3.82-3.80 (m, 4H), 2.68 (t, J=7.3 Hz, 2H), 2.56-2.49 (m, 4H), 2.38-2.35 (t, J=7.2 Hz, 2H), 1.83-1.75 (m, 2H).

Example 24 3-(4-(4-(4-Cyanopyrimidin-2-yl)piperazin-1-yl)butyl)-1H-indole-5-carbonitrile

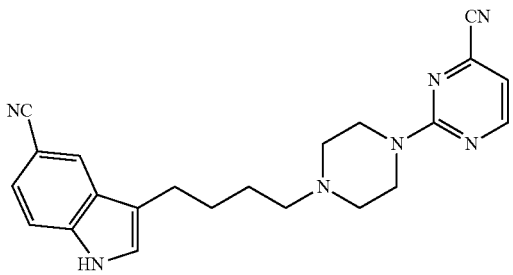 [SMILES: N#Cc1ccc2[nH]cc(CCCCN3CCN(c4nccc(C#N)n4)CC3)c2c1]

The title compound was prepared by the procedure described in step 6 of example 1, using 4-(5-cyano-1H-indol-3-yl)butyl 4-methylbenzenesulfonate (214 mg, 0.58 mmol), 2-(piperazin-1-yl)pyrimidine-4-carbonitrile (110 mg, 0.58 mmol), potassium carbonate (120 mg, 0.87 mmol) and potassium iodide (20 mg, 0.12 mmol) in acetonitrile (15 mL) to give the title compound as a white solid (156 mg, 70%). The compound was characterized by the following spectroscopic data: LC-MS (ESI, pos. ion) m/z: 386.3 [M+H]$^+$ and $^1$H NMR (CDCl$_3$, 400 MHz) δ (ppm): 8.42 (d, J=4.7 Hz, 1H), 8.36 (s, 1H), 7.95 (s, 1H), 7.43-7.38 (m, 1H), 7.11 (d, J=2.0 Hz, 1H), 6.73 (d, J=4.6 Hz, 1H), 6.75 (d, J=4.7 Hz, 1H), 3.87 (t, J=4.6 Hz, 4H), 2.79 (t, J=7.3 Hz, 2H), 2.52 (t, J=4.6 Hz, 4H), 2.46 (t, J=7.5 Hz, 2H), 1.75-1.70 (m, 2H), 1.68-1.60 (m, 2H).

Example 25 2-(4-(3-(5-Fluoro-1H-indol-3-yl)propyl)piperazin-1-yl)pyrimidine-4-carbonitrile

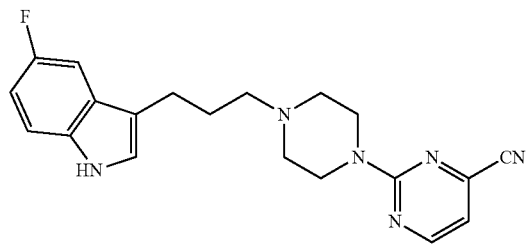 [SMILES: N#Cc1ccnc(N2CCN(CCCc3c[nH]c4ccc(F)cc34)CC2)n1]

The title compound was prepared by the procedure described in step 6 of example 1, using 3-(5-fluoro-1H-indol-3-yl)propyl 4-methylbenzenesulfonate (201 mg, 0.58 mmol), 2-(piperazin-1-yl)pyrimidine-4-carbonitrile (110 mg, 0.58 mmol), potassium carbonate (120 mg, 0.87 mmol) and potassium iodide (20 mg, 0.12 mmol) in acetonitrile (15 mL) to give the title compound as a white solid (145 mg, 69%). The compound was characterized by the following spectroscopic data: LC-MS (ESI, pos. ion) m/z: 365.3 [M+H]$^+$ and $^1$H NMR (CDCl$_3$, 400 MHz) δ (ppm): 8.42 (d, J=4.6 Hz, 1H), 7.99 (s, 1H), 7.28-7.23 (m, 2H), 7.05 (d, J=2.0 Hz, 1H), 6.93 (d, J=8.8 Hz, 1H), 6.73 (d, J=4.7 Hz, 1H), 3.89 (t, J=4.9 Hz, 4H), 2.77 (t, J=7.5 Hz, 2H), 2.53 (t, J=5.0 Hz, 4H), 2.49 (t, J=7.6 Hz, 2H), 1.95-1.87 (m, 2H).

Example 26 3-(3-(4-(4-Cyanopyrimidin-2-yl)piperazin-1-yl)propyl)-1H-indole-5-carbonitrile

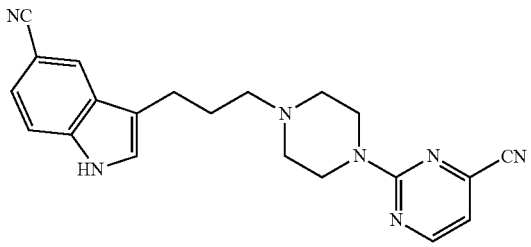 [SMILES: N#Cc1ccc2[nH]cc(CCCN3CCN(c4nccc(C#N)n4)CC3)c2c1]

The title compound was prepared by the procedure described in step 6 of example 1, using 3-(5-cyano-1H-indol-3-yl)propyl 4-methylbenzenesulfonate (206 mg, 0.58 mmol), 2-(piperazin-1-yl)pyrimidine-4-carbonitrile (110 mg, 0.58 mmol), potassium carbonate (120 mg, 0.87 mmol) and potassium iodide (20 mg, 0.12 mmol) in acetonitrile (15 mL) to give the title compound as a white solid (130 mg, 60%). The compound was characterized by the following spectroscopic data: LC-MS (ESI, pos. ion) m/z: 372.3 [M+H]$^+$ and $^1$H NMR (CDCl$_3$, 400 MHz) δ (ppm): 8.43 (d, J=4.7 Hz, 1H), 8.33 (s, 1H), 7.97 (s, 1H), 7.42-7.41 (m, 2H), 7.16 (s, 1H), 6.74 (d, J=4.6 Hz, 1H), 3.93-3.91 (m, 4H), 2.82 (t, J=7.4 Hz, 2H), 2.57-2.52 (m, 6H), 2.04-1.99 (m, 2H).

Example 27 2-(4-(4-(5-Fluoro-1H-indol-3-yl)butyl)piperazin-1-yl)pyrimidine-4-carboxamide

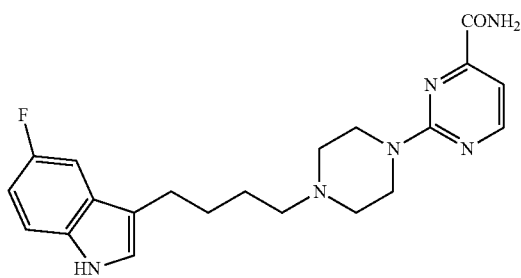 [SMILES: NC(=O)c1ccnc(N2CCN(CCCCc3c[nH]c4ccc(F)cc34)CC2)n1]

Step 1) 2-(piperazin-1-yl)pyrimidine-4-carboxamide

The title compound was prepared by the procedure described in step 5 of example 1, using 2-chloropyrimidine-4-carboxamide (1.13 g, 7.2 mmol), potassium carbonate (1.00 g, 7.2 mmol) and anhydrous piperazine (1.24 g, 14.4 mmol) in DMF (10 mL) to give the title compound as a yellow solid (1.04 g, 70.0%). The compound was characterized by the following spectroscopic data: LC-MS (ESI, pos. ion) m/z: 208.1 [M+H]$^+$ and $^1$H NMR (DMSO-d$_6$, 400 MHz) δ (ppm): 8.55 (d, J=4.8 Hz, 1H), 8.18 (s, 1H), 7.72 (s, 1H), 7.10 (d, J=4.8 Hz, 1H), 3.82 (t, J=4.9 Hz, 4H), 2.84 (t, J=5.1 Hz, 4H).

Step 2) 2-(4-(4-(5-fluoro-1H-indol-3-yl)butyl)piperazin-1-yl)pyrimidine-4-carboxamide The title compound was prepared by the procedure described in step 6 of example 1, using 4-(5-fluoro-1H-indol-3-yl)butyl 4-methylbenzenesulfonate (210 mg, 0.58 mmol), 2-(piperazin-1-yl)pyrimidine-4-carboxamide (120 mg, 0.58 mmol), potassium carbonate (120 mg, 0.87 mmol) and potassium iodide (20 mg, 0.12 mmol) in acetonitrile (15 mL) to give the title compound as a white solid (180 mg, 78%). The compound was characterized by the following spectroscopic data: LC-MS (ESI, pos. ion) m/z: 397.3 [M+H]$^+$ and $^1$H NMR (DMSO-d$_6$, 400 MHz) δ (ppm): 10.83 (s, 1H), 8.53 (d, J=4.8 Hz, 1H), 8.16 (s, 1H), 7.70-7.68 (m, 1H), 7.33-7.29 (m, 1H), 7.25 (dd, J=10.1, 2.5 Hz, 1H), 7.18 (d, J=2.2 Hz, 1H), 7.08 (d, J=4.8 Hz, 1H), 6.88 (dd, J=9.2, 2.5 Hz, 1H), 3.79 (m, 4H), 2.67 (t, J=7.3 Hz, 2H), 2.49 (t, J=7.6 Hz, 2H), 2.41-2.37 (m, 4H), 1.67-1.61 (m, 2H), 1.56-1.49 (m, 2H).

Example 28 2-(4-(4-(5-Cyano-1H-indol-3-yl)butyl)piperazin-1-yl)pyrimidine-4-carboxamide

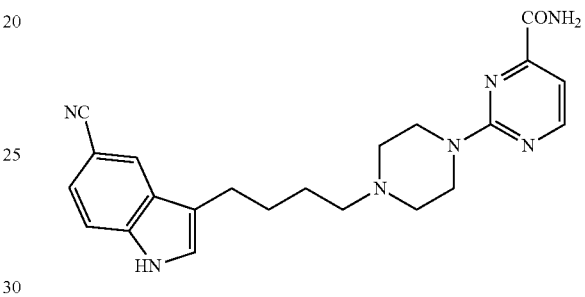

The title compound was prepared by the procedure described in step 6 of example 1, using 4-(5-cyano-1H-indol-3-yl)butyl 4-methylbenzenesulfonate (214 mg, 0.58 mmol), 2-(piperazin-1-yl)pyrimidine-4-carboxamide (120 mg, 0.58 mmol), potassium carbonate (120 mg, 0.87 mmol) and potassium iodide (20 mg, 0.12 mmol) in acetonitrile (15 mL) to give the title compound as a white solid (145 mg, 62%). The compound was characterized by the following spectroscopic data: LC-MS (ESI, pos. ion) m/z: 404.3 [M+H]$^+$ and $^1$H NMR (DMSO-d$_6$, 400 MHz) δ (ppm): 11.35 (s, 1H), 8.53 (d, J=4.8 Hz, 1H), 8.15 (s, 1H), 8.07 (s, 1H), 7.70 (s, 1H), 7.49 (d, J=8.4 Hz, 1H), 7.40 (d, J=8.4 Hz, 1H), 7.33 (s, 1H), 7.08 (d, J=4.8 Hz, 1H), 3.79-3.78 (m, 4H), 2.74 (t, J=7.4 Hz, 2H), 2.39 (t, J=4.8 Hz, 4H), 2.35 (t, J=7.5 Hz, 2H), 1.69-1.65 (m, 2H), 1.54-1.51 (m, 2H).

Example 29 2-(4-(3-(5-Fluoro-1H-indol-3-yl)propyl)piperazin-1-yl)pyrimidine-4-carboxamide

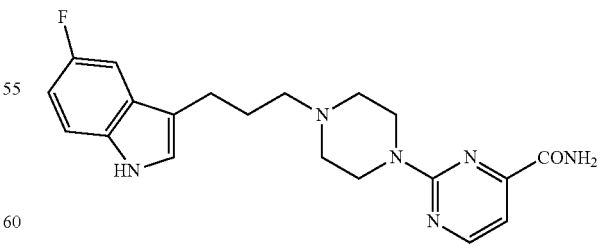

The title compound was prepared by the procedure described in step 6 of example 1, using 3-(5-fluoro-1H-indol-3-yl)propyl 4-methylbenzenesulfonate (201 mg, 0.58 mmol), 2-(piperazin-1-yl)pyrimidine-4-carboxamide (120 mg, 0.58 mmol), potassium carbonate (120 mg, 0.87 mmol)

and potassium iodide (20 mg, 0.12 mmol) in acetonitrile (15 mL) to give the title compound as a white solid (188 mg, 85%). The compound was characterized by the following spectroscopic data: LC-MS (ESI, pos. ion) m/z: 383.1 [M+H]$^+$ and $^1$H NMR (DMSO-d$_6$, 400 MHz) δ (ppm): 10.84 (s, 1H), 8.53 (d, J=4.8 Hz, 1H), 8.16 (s, 1H), 7.70 (s, 1H), 7.33-7.30 (m, 1H), 7.25 (dd, J=10.1, 2.5 Hz, 1H), 7.20 (d, J=2.1 Hz, 1H), 7.08 (d, J=4.8 Hz, 1H), 6.88 (dd, J=9.2, 2.5 Hz, 1H), 3.82-3.79 (m, 4H), 2.68 (t, J=7.4 Hz, 2H), 2.42-2.39 (m, 4H), 2.37 (t, J=7.2 Hz, 2H), 1.78-1.68 (m, 2H).

Example 30 2-(4-(3-(5-Cyano-1H-indol-3-yl)propyl)piperazin-1-yl)pyrimidine-4-carboxamide

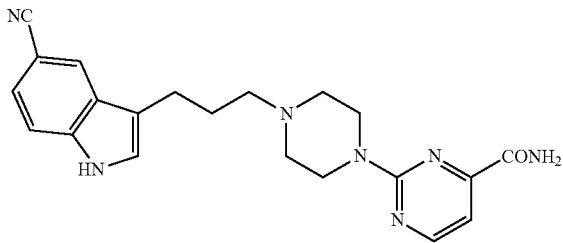 [SMILES: N#Cc1ccc2[nH]cc(CCCN3CCN(c4nccc(C(N)=O)n4)CC3)c2c1]

The title compound was prepared by the procedure described in step 6 of example 1, using 3-(5-cyano-1H-indol-3-yl)propyl 4-methylbenzenesulfonate (206 mg, 0.58 mmol), 2-(piperazin-1-yl)pyrimidine-4-carboxamide (120 mg, 0.58 mmol), potassium carbonate (120 mg, 0.87 mmol) and potassium iodide (20 mg, 0.1 mol) in acetonitrile (15 mL) to give the title compound as a white solid (157 mg, 70%). The compound was characterized by the following spectroscopic data: LC-MS (ESI, pos. ion) m/z: 390.1 [M+H]$^+$ and $^1$H NMR (DMSO-d$_6$, 400 MHz) δ (ppm): 11.37 (s, 1H), 8.54 (d, J=4.8 Hz, 1H), 8.16 (s, 1H), 8.09 (s, 1H), 7.70 (s, 1H), 7.49 (d, J=8.4 Hz, 1H), 7.39 (dd, J=8.4, 1.4 Hz, 1H), 7.34 (d, J=2.0 Hz, 1H), 7.08 (d, J=4.8 Hz, 1H), 3.82 (t, J=4.7 Hz, 4H), 2.75 (t, J=7.4 Hz, 2H), 2.41 (t, J=4.7 Hz, 4H), 2.36 (t, J=7.2 Hz, 2H), 1.87-1.80 (m, 2H).

Example 31 5-Fluoro-3-(4-(4-(4-(trifluoromethyl)pyrimidin-2-yl)piperazin-1-yl)butyl)-1H-indole

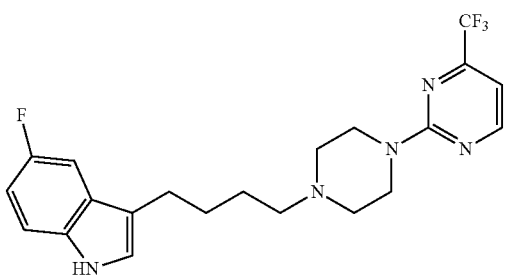 [SMILES: Fc1ccc2[nH]cc(CCCCN3CCN(c4nccc(C(F)(F)F)n4)CC3)c2c1]

Step 1)
2-(piperazin-1-yl)-4-(trifluoromethyl)pyrimidine

The title compound was prepared by the procedure described in step 5 of example 1, using 2-chloro-4-(trifluoromethyl)pyrimidine (1.31 g, 7.2 mmol), potassium carbonate (1.00 g, 7.2 mmol) and anhydrous piperazine (1.24 g, 14.4 mmol) in DMF (10 mL) to give the title compound as yellow oil (1.25 g, 75%). The compound was characterized by the following spectroscopic data: LC-MS (ESI, pos. ion) m/z: 233.1 [M+H]$^+$ and $^1$H NMR (CDCl$_3$, 400 MHz) δ (ppm): 8.48 (d, J=4.8 Hz, 1H), 6.73 (d, J=4.8 Hz, 1H), 3.84 (t, J=5.1 Hz, 4H), 2.93 (t, J=5.1 Hz, 4H).

Step 2) 5-fluoro-3-(4-(4-(4-(trifluoromethyl)pyrimidin-2-yl)piperazin-1-yl)butyl)-1H-indole The title compound was prepared by the procedure described in step 6 of example 1, using 4-(5-fluoro-1H-indol-3-yl)butyl 4-methylbenzenesulfonate (210 mg, 0.58 mmol), 2-(piperazin-1-yl)-4-(trifluoromethyl)pyrimidine (135 mg, 0.58 mmol), potassium carbonate (120 mg, 0.87 mmol) and potassium iodide (20 mg, 0.12 mmol) in acetonitrile (15 mL) to give the title compound as a white solid (198 mg, 81.0%). The compound was characterized by the following spectroscopic data: LC-MS (ESI, pos. ion) m/z: 422.2 [M+H]$^+$ and $^1$H NMR (CDCl$_3$, 400 MHz) δ (ppm): 8.47 (d, J=4.8 Hz, 1H), 8.33 (s, 1H), 7.97-7.95 (m, 1H), 7.25-7.21 (m, 2H), 7.03 (d, J=1.9 Hz, 1H), 6.92 (td, J=9.1, 2.5 Hz, 1H), 6.74 (d, J=4.8 Hz, 1H), 3.91 (t, J=4.7 Hz, 4H), 2.74 (t, J=7.3 Hz, 2H), 2.54 (t, J=4.7 Hz, 4H), 2.46 (t, J=7.5 Hz, 2H), 1.77-1.61 (m, 4H).

Example 32 3-(4-(4-(4-(Trifluoromethyl)pyrimidin-2-yl)piperazin-1-yl)butyl)-1H-indole-5-carbonitrile

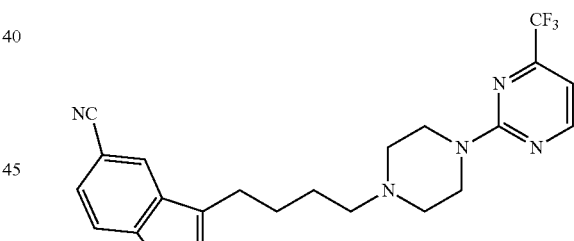

The title compound was prepared by the procedure described in step 6 of example 1, using 4-(5-cyano-1H-indol-3-yl)butyl 4-methylbenzenesulfonate (214 mg, 0.58 mmol), 2-(piperazin-1-yl)-4-(trifluoromethyl)pyrimidine (135 mg, 0.58 mmol), potassium carbonate (120 mg, 0.87 mmol) and potassium iodide (20 mg, 0.12 mmol) in acetonitrile (15 mL) to give the title compound as a white solid (132 mg, 53%). The compound was characterized by the following spectroscopic data: LC-MS (ESI, pos. ion) m/z: 429.2 [M+H]$^+$ and $^1$H NMR (CDCl$_3$, 400 MHz), δ (ppm): 8.47 (d, J=4.8 Hz, 1H), 8.33 (s, 1H), 7.95 (s, 1H), 7.41-7.40 (m, 2H), 7.11 (d, J=2.2 Hz, 1H), 6.75 (d, J=4.8 Hz, 1H), 3.92 (t, J=4.6 Hz, 4H), 2.79 (t, J=7.3 Hz, 2H), 2.56 (t, J=4.7 Hz, 4H), 2.48 (t, J=7.5 Hz, 2H), 1.79-1.66 (m, 4H).

Example 33 5-Fluoro-3-(3-(4-(4-(trifluoromethyl)pyrimidin-2-yl)piperazin-1-yl)propyl)-1H-indole

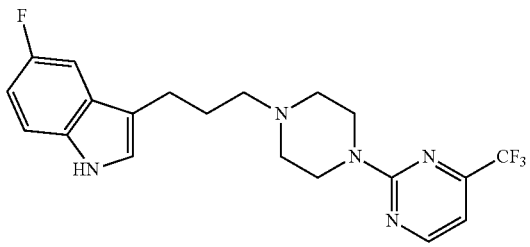 [SMILES: Fc1ccc2[nH]cc(CCCN3CCN(c4nccc(C(F)(F)F)n4)CC3)c2c1]

The title compound was prepared by the procedure described in step 6 of example 1, using 3-(5-fluoro-1H-indol-3-yl)propyl 4-methylbenzenesulfonate (201 mg, 0.58 mmol), 2-(piperazin-1-yl)-4-(trifluoromethyl)pyrimidine (135 mg, 0.58 mmol), potassium carbonate (120 mg, 0.87 mmol) and potassium iodide (20 mg, 0.12 mmol) in acetonitrile (15 mL) to give the title compound as a white solid (208 mg, 88.0%). The compound was characterized by the following spectroscopic data: LC-MS (ESI, pos. ion) m/z: 408.2 [M+H]$^+$ and $^1$H NMR (CDCl$_3$, 400 MHz) δ (ppm): 8.47 (d, J=4.8 Hz, 1H), 7.99 (s, 1H), 7.28-7.23 (m, 2H), 7.05 (d, J=2.0 Hz, 1H), 6.93 (td, J=9.0, 2.5 Hz, 1H), 6.74 (d, J=4.8 Hz, 1H), 3.92 (t, J=5.0 Hz, 4H), 2.77 (t, J=7.5 Hz, 2H), 2.55 (t, J=5.0 Hz, 4H), 2.50 (t, J=7.6 Hz, 2H), 1.99-1.92 (m, 2H).

Example 34 3-(3-(4-(4-(Trifluoromethyl)pyrimidin-2-yl)piperazin-1-yl)propyl)-1H-indole-5-carbonitrile

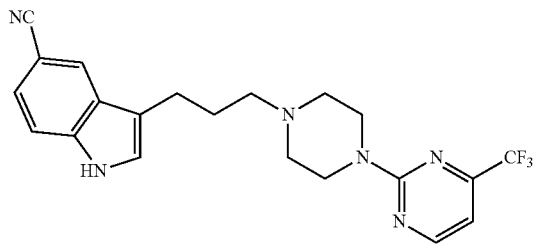 [SMILES: N#Cc1ccc2[nH]cc(CCCN3CCN(c4nccc(C(F)(F)F)n4)CC3)c2c1]

The title compound was prepared by the procedure described in step 6 of example 1, using 3-(5-cyano-1H-indol-3-yl)propyl 4-methylbenzenesulfonate (206 mg, 0.58 mmol), 2-(piperazin-1-yl)-4-(trifluoromethyl)pyrimidine (135 mg, 0.58 mmol), potassium carbonate (120 mg, 0.87 mmol) and potassium iodide (20 mg, 0.12 mmol) in acetonitrile (15 mL) to give the title compound as a white solid (146 mg, 61%). The compound was characterized by the following spectroscopic data: LC-MS (ESI, pos. ion) m/z: 415.1 [M+H]$^+$ and $^1$H NMR (CDCl$_3$, 400 MHz) δ (ppm): 8.47 (d, J=4.8 Hz, 1H), 8.39 (s, 1H), 7.98 (s, 1H), 7.41-7.37 (m, 2H), 7.14 (d, J=2.1 Hz, 1H), 6.74 (d, J=4.8 Hz, 1H), 3.92 (t, J=4.9 Hz, 4H), 2.82 (t, J=7.4 Hz, 2H), 2.55 (t, J=5.0 Hz, 4H), 2.50 (t, J=7.5 Hz, 2H), 1.98-1.93 (m, 2H).

Example 35 3-(4-(4-(5-Fluoropyrimidin-2-yl)piperazin-1-yl)butyl)-1H-indole-5-carbonitrile

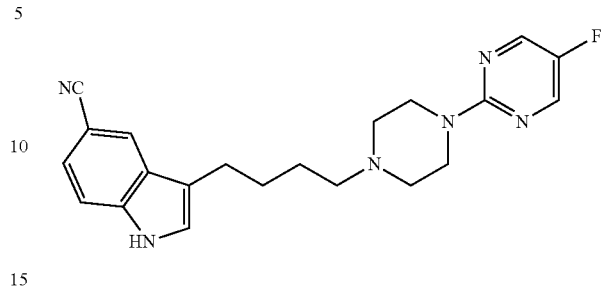

Step 1) 5-fluoro-2-(piperazin-1-yl)pyrimidine

The title compound was prepared by the procedure described in step 5 of example 1, using 2-chloro-5-fluoropyrimidine (0.95 g, 7.2 mmol), potassium carbonate (1.00 g, 7.2 mmol) and anhydrous piperazine (1.24 g, 14.4 mmol) in DMF (10 mL) to give the title compound as a white solid (0.72 g, 55%). The compound was characterized by the following spectroscopic data: LC-MS (ESI, pos. ion) m/z: 183.2 [M+H]$^+$ and $^1$H NMR (CDCl$_3$, 400 MHz) δ (ppm): 8.19 (s, 2H), 3.74 (t, J=5.1 Hz, 4H), 2.93 (t, J=5.1 Hz, 4H).

Step 2) 3-(4-(4-(5-fluoropyrimidin-2-yl)piperazin-1-yl)butyl)-1H-indole-5-carbonitrile The title compound was prepared by the procedure described in step 6 of example 1, using 4-(5-cyano-1H-indol-3-yl)butyl 4-methylbenzenesulfonate (214 mg, 0.58 mmol), 5-fluoro-2-(piperazin-1-yl)pyrimidine (106 mg, 0.58 mmol), potassium carbonate (120 mg, 0.87 mmol) and potassium iodide (20 mg, 0.12 mmol) in acetonitrile (15 mL) to give the title compound as a white solid (131 mg, 60%). The compound was characterized by the following spectroscopic data: LC-MS (ESI, pos. ion) m/z: 379.3 [M+H]$^+$ and $^1$H NMR (CD$_3$OD, 400 MHz) δ (ppm): 8.26 (d, J=0.5 Hz, 2H), 7.98 (s, 1H), 7.45 (dd, J=8.4, 0.4 Hz, 1H), 7.35 (dd, J=8.4, 1.5 Hz, 1H), 7.21 (s, 1H), 3.75 (t, J=5.1 Hz, 4H), 2.82 (t, J=7.3 Hz, 2H), 2.50 (t, J=5.1 Hz, 4H), 2.44 (t, J=7.7 Hz, 2H), 1.79-1.71 (m, 2H), 1.67-1.59 (m, 2H).

Example 36 3-(3-(4-(5-Fluoropyrimidin-2-yl)piperazin-1-yl)propyl)-1H-indole-5-carbonitrile

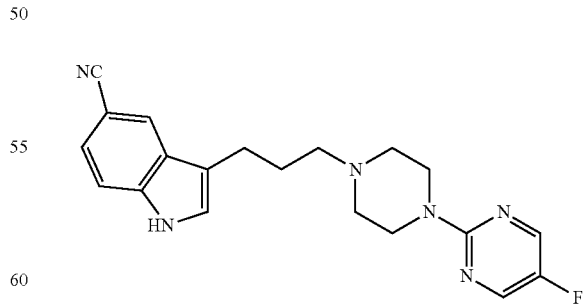

The title compound was prepared by the procedure described in step 6 of example 1, using 3-(5-cyano-1H-indol-3-yl)propyl 4-methylbenzenesulfonate (206 mg, 0.58 mmol), 5-fluoro-2-(piperazin-1-yl)pyrimidine (106 mg, 0.58 mmol), potassium carbonate (120 mg, 0.87 mmol) and potassium iodide (20 mg, 0.12 mmol) in acetonitrile (15 mL) to give the title compound as a white solid (135 mg, 64%). The compound was characterized by the following spectroscopic data: LC-MS (ESI, pos. ion) m/z: 365.3 [M+H]+ and 1H NMR (CD3OD, 400 MHz) δ (ppm): 8.14 (m, 2H), 7.90 (s, 1H), 7.39-7.37 (m, 1H), 7.31 (dd, J=8.4, 1.5 Hz, 1H), 7.10 (s, 1H), 3.73 (d, J=5.1 Hz, 4H), 2.75 (d, J=7.4 Hz, 2H), 2.50 (t, J=5.1 Hz, 4H), 2.46-2.43 (m, 2H), 1.95-1.87 (m, 2H).

Example 37 Ethyl 2-(4-(4-(5-fluoro-1H-indol-3-yl)butyl)piperazin-1-yl)-4-methylthiazole-5-carboxylate

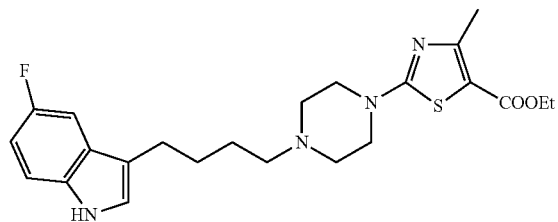 [SMILES: CCOC(=O)c1sc(N2CCN(CCCCc3c[nH]c4ccc(F)cc34)CC2)nc1C]

Step 1) ethyl 4-methyl-2-(piperazin-1-yl)thiazole-5-carboxylate

The title compound was prepared by the procedure described in step 5 of example 1, using ethyl 2-bromo-4-methylthiazole-5-carboxylate (1.80 g, 7.2 mmol), potassium carbonate (1.00 g, 7.2 mmol) and anhydrous piperazine (1.24 g, 14.4 mmol) in DMF (10 mL) to give the title compound as a yellow solid (1.65 g, 90%). The compound was characterized by the following spectroscopic data: LC-MS (ESI, pos. ion) m/z: 256.1 [M+H]+ and 1H NMR (CDCl3, 400 MHz) δ (ppm): 4.25 (q, J=7.2 Hz, 2H), 3.52-3.49 (m, 4H), 2.97-2.94 (m, 4H), 2.54 (s, 3H), 1.32 (t, J=7.2 Hz, 3H).

Step 2) ethyl 2-(4-(4-(5-fluoro-1H-indol-3-yl)butyl)piperazin-1-yl)-4-methylthiazole-5-carboxylate The title compound was prepared by the procedure described in step 6 of example 1, using 4-(5-fluoro-1H-indol-3-yl)butyl 4-methylbenzenesulfonate (210 mg, 0.58 mmol), ethyl 4-methyl-2-(piperazin-1-yl)thiazole-5-carboxylate (148 mg, 0.58 mmol), potassium carbonate (120 mg, 0.87 mmol) and potassium iodide (20 mg, 0.12 mmol) in acetonitrile (15 mL) to give the title compound as a white solid (211 mg, 82%). The compound was characterized by the following spectroscopic data: LC-MS (ESI, pos. ion) m/z: 445.1 [M+H]+ and 1H NMR (CDCl3, 400 MHz) δ (ppm): 8.19 (br s, 1H), 7.23-7.28 (m, 2H), 7.03 (d, J=2.0 Hz, 1H), 6.93 (td, J=8.8, 2.4 Hz, 1H), 4.27 (q, J=7.2 Hz, 2H), 3.54-3.57 (m, 4H), 2.75 (t, J=7.2 Hz, 2H), 2.57 (s, 3H), 2.54-2.51 (m, 4H), 2.45-2.42 (m, 2H), 1.76-1.71 (m, 2H), 1.65-1.59 (m, 2H), 1.34 (t, J=7.2 Hz, 3H).

Example 38 Ethyl 2-(4-(3-(5-fluoro-1H-indol-3-yl)propyl)piperazin-1-yl)-4-methylthiazole-5-carboxylate

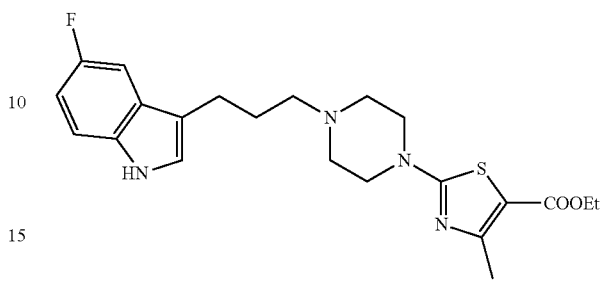

The title compound was prepared by the procedure described in step 6 of example 1, using 3-(5-fluoro-1H-indol-3-yl)propyl 4-methylbenzenesulfonate (201 mg, 0.58 mmol), ethyl 4-methyl-2-(piperazin-1-yl)thiazole-5-carboxylate (148 mg, 0.58 mmol), potassium carbonate (120 mg, 0.87 mmol) and potassium iodide (20 mg, 0.12 mmol) in acetonitrile (15 mL) to give the title compound as a white solid (200 mg, 80%). The compound was characterized by the following spectroscopic data: LC-MS (ESI, pos. ion) m/z: 431.3 [M+H]+ and 1H NMR (CDCl3, 400 MHz) δ (ppm): 7.98 (br s, 1H), 7.25-7.22 (m, 2H), 7.02 (d, J=1.6 Hz, 1H), 6.93 (td, J=8.8, 2.4 Hz, 1H), 4.25 (q, J=7.2 Hz, 2H), 3.57-3.54 (m, 4H), 2.76 (t, J=7.2 Hz, 2H), 2.55-2.52 (m, 7H), 2.48-2.44 (m, 2H), 1.94-1.86 (m, 2H), 1.32 (t, J=7.2 Hz, 3H).

Example 39 Ethyl 2-(4-(4-(5-cyano-1H-indol-3-yl)butyl)piperazin-1-yl)-4-methylthiazole-5-carboxylate

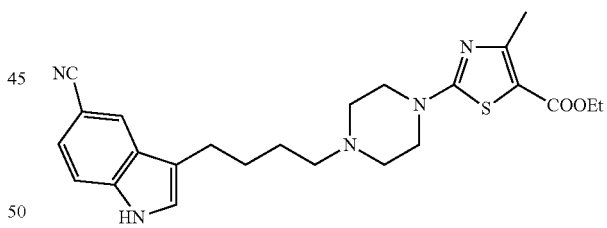

The title compound was prepared by the procedure described in step 6 of example 1, using 4-(5-cyano-1H-indol-3-yl)butyl 4-methylbenzenesulfonate (214 mg, 0.58 mmol), ethyl 4-methyl-2-(piperazin-1-yl)thiazole-5-carboxylate (148 mg, 0.58 mmol), potassium carbonate (120 mg, 0.87 mmol) and potassium iodide (20 mg, 0.12 mmol) in acetonitrile (15 mL) to give the title compound as a white solid (196 mg, 75%). The compound was characterized by the following spectroscopic data: LC-MS (ESI, pos. ion) m/z: 452.1 [M+H]+ and 1H NMR (CDCl3, 400 MHz) δ (ppm): 8.47 (br s, 1H), 7.94 (s, 1H), 7.40-7.36 (m, 2H), 7.09 (d, J=2.0 Hz, 1H), 4.25 (q, J=7.2 Hz, 2H), 3.55-3.52 (m, 4H), 2.77 (t, J=7.2 Hz, 2H), 2.54 (s, 3H), 2.52-2.50 (m, 4H), 2.44-2.40 (m, 2H), 1.74-1.70 (m, 2H), 1.63-1.57 (m, 2H), 1.32 (t, J=7.2 Hz, 3H).

Example 40 Ethyl 2-(4-(3-(5-cyano-1H-indol-3-yl)propyl)piperazin-1-yl)-4-methylthiazole-5-carboxylate

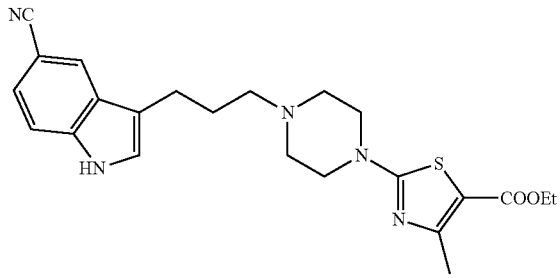 [SMILES: CCOC(=O)c1sc(N2CCN(CCCc3c[nH]c4ccc(C#N)cc34)CC2)nc1C]

The title compound was prepared by the procedure described in step 6 of example 1, using 3-(5-cyano-1H-indol-3-yl)propyl 4-methylbenzenesulfonate (205 mg, 0.58 mmol), ethyl 4-methyl-2-(piperazin-1-yl)thiazole-5-carboxylate (148 mg, 0.58 mmol), potassium carbonate (120 mg, 0.87 mmol) and potassium iodide (20 mg, 0.12 mmol) in acetonitrile (15 mL) to give the title compound as a white solid (195 mg, 77%). The compound was characterized by the following spectroscopic data: LC-MS (ESI, pos. ion) m/z: 438.3 [M+H]$^+$ and $^1$H NMR (CDCl$_3$, 400 MHz) δ (ppm): 8.40 (br s, 1H), 7.90 (s, 1H), 7.34-7.32 (m, 2H), 7.04 (d, J=1.6 Hz, 1H), 4.18 (q, J=7.2 Hz, 2H), 3.50-3.48 (m, 4H), 2.73 (t, J=7.2 Hz, 2H), 2.47 (s, 3H), 2.46-2.45 (m, 4H), 2.40-2.36 (m, 2H), 1.88-1.80 (m, 2H), 1.25 (t, 3H, J=7.2 Hz).

Example 41 2-(4-(4-(5-Fluoro-1H-indol-3-yl)butyl)piperazin-1-yl)-4-methylthiazole-5-carboxamide

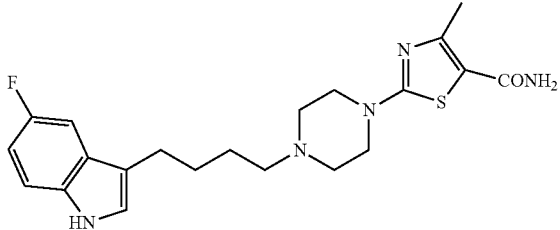 [SMILES: Cc1nc(N2CCN(CCCCc3c[nH]c4ccc(F)cc34)CC2)sc1C(N)=O]

Step 1) 2-bromo-4-methylthiazole-5-carboxamide

A mixture of ethyl 2-bromo-4-methylthiazole-5-carboxylate (6.0 g, 23.99 mmol) in concentrated ammonia (175 mL) was stirred at rt for 20 hours. Then the reaction mixture was filtered. The filter cake was washed with water and dried to give the title compound as a red solid (3.03 g, 57%). The compound was characterized by the following spectroscopic data: LC-MS (ESI, pos. ion) m/z: 223.0 [M+H]$^+$ and $^1$H NMR (CDCl$_3$, 400 MHz) δ (ppm): 5.79 (br s, 2H), 2.71 (s, 3H).

Step 2) 4-methyl-2-(piperazin-1-yl)thiazole-5-carboxamide

The title compound was prepared by the procedure described in step 5 of example 1, using 2-bromo-4-methylthiazole-5-carboxamide (1.60 g, 7.2 mmol), potassium carbonate (1.00 g, 7.2 mmol) and anhydrous piperazine (1.24 g, 14.4 mmol) in DMF (10 mL) to give the title compound as a yellow solid (1.59 g, 98%). The compound was characterized by the following spectroscopic data: LC-MS (ESI, pos. ion) m/z: 227.0 [M+H]$^+$.

Step 3) 2-(4-(4-(5-fluoro-1H-indol-3-yl)butyl)piperazin-1-yl)-4-methylthiazole-5-carboxamide The title compound was prepared by the procedure described in step 6 of example 1, using 4-(5-fluoro-1H-indol-3-yl)butyl 4-methylbenzenesulfonate (210 mg, 0.58 mmol), 4-methyl-2-(piperazin-1-yl)thiazole-5-carboxamide (131 mg, 0.58 mmol), potassium carbonate (120 mg, 0.87 mmol) and potassium iodide (20 mg, 0.12 mmol) in acetonitrile (15 mL) to give the title compound as a white solid (210 mg, 87%). The compound was characterized by the following spectroscopic data: LC-MS (ESI, pos. ion) m/z: 416.1 [M+H]$^+$ and $^1$H NMR (CDCl$_3$/CD$_3$OD=1/1, 400 MHz) δ (ppm): 7.25 (dd, J=8.8, 4.4 Hz, 1H), 7.15 (dd, J=9.6, 2.4 Hz, 1H), 7.03 (s, 1H), 6.83 (td, J=8.8, 2.4 Hz, 1H), 3.51-3.49 (m, 4H), 2.73 (t, J=7.2 Hz, 2H), 2.55-2.53 (m, 4H), 2.47 (s, 3H), 2.45-2.41 (m, 2H), 1.74-1.70 (m, 2H), 1.62-1.57 (m, 2H).

Example 42 2-(4-(3-(5-Fluoro-1H-indol-3-yl)propyl)piperazin-1-yl)-4-methylthiazole-5-carboxamide

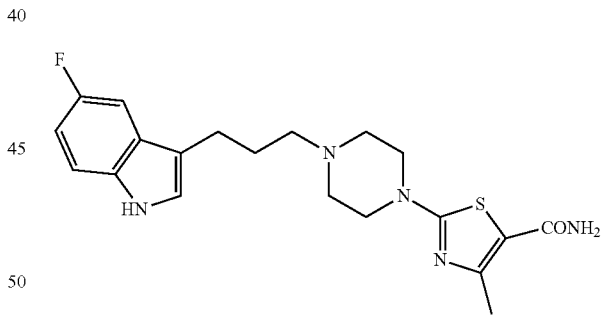

The title compound was prepared by the procedure described in step 6 of example 1, using 3-(5-fluoro-1H-indol-3-yl)propyl 4-methylbenzenesulfonate (201 mg, 0.58 mmol), 4-methyl-2-(piperazin-1-yl)thiazole-5-carboxamide (131 mg, 0.58 mmol), potassium carbonate (120 mg, 0.87 mmol) and potassium iodide (20 mg, 0.12 mmol) in acetonitrile (15 mL) to give the title compound as a white solid (198 mg, 85%). The compound was characterized by the following spectroscopic data: LC-MS (ESI, pos. ion) m/z: 402.2 [M+H]$^+$ and $^1$H NMR (CDCl$_3$, 400 MHz) δ (ppm): 8.07 (br s, 1H), 7.24-7.22 (m, 2H), 7.03 (d, J=2.0 Hz, 1H), 6.93 (td, J=8.8, 2.0 Hz, 1H), 5.50 (br s, 2H), 3.55-3.52 (m, 4H), 2.75 (t, J=7.2 Hz, 2H), 2.55-2.51 (m, 7H), 2.47-2.44 (m, 2H), 1.92-1.86 (m, 2H).

Example 43 2-(4-(4-(5-Cyano-1H-indol-3-yl)butyl)piperazin-1-yl)-4-methylthiazole-5-carboxamide

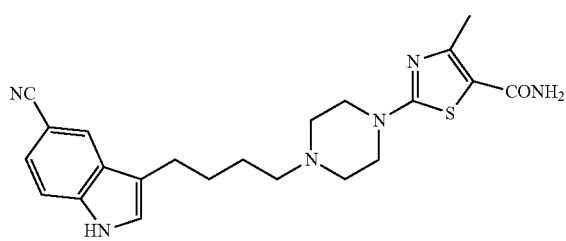 [SMILES: Cc1nc(N2CCN(CCCCc3c[nH]c4ccc(C#N)cc34)CC2)sc1C(N)=O]

The title compound was prepared by the procedure described in step 6 of example 1, using 4-(5-cyano-1H-indol-3-yl)butyl 4-methylbenzenesulfonate (214 mg, 0.58 mmol), 4-methyl-2-(piperazin-1-yl)thiazole-5-carboxamide (131 mg, 0.58 mmol), potassium carbonate (120 mg, 0.87 mmol) and potassium iodide (20 mg, 0.12 mmol) in acetonitrile (15 mL) to give the title compound as a white solid (198 mg, 81%). The compound was characterized by the following spectroscopic data: LC-MS (ESI, pos. ion) m/z: 423.1 [M+H]$^+$ and $^1$H NMR (CDCl$_3$/CD$_3$OD=1/1, 400 MHz) δ (ppm): 7.90 (s, 1H), 7.41 (d, J=8.4 Hz, 1H), 7.31 (dd, J=8.4, 0.8 Hz, 1H), 7.12 (s, 1H), 3.50-3.48 (m, 4H), 2.77 (t, J=7.2 Hz, 2H), 2.55-2.52 (m, 4H), 2.47-2.41 (m, 5H), 1.74-1.70 (m, 2H), 1.62-1.59 (m, 2H).

Example 44 2-(4-(3-(5-Cyano-1H-indol-3-yl)propyl)piperazin-1-yl)-4-methylthiazole-5-carboxamide

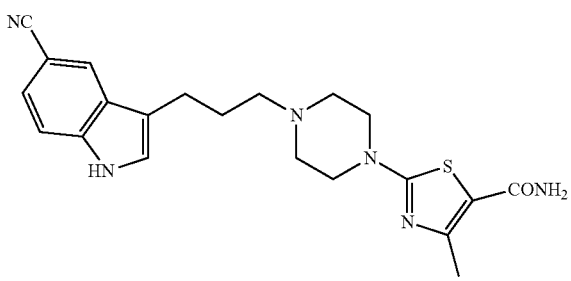 [SMILES: Cc1nc(N2CCN(CCCc3c[nH]c4ccc(C#N)cc34)CC2)sc1C(N)=O]

The title compound was prepared by the procedure described in step 6 of example 1, using 3-(5-cyano-1H-indol-3-yl)propyl 4-methylbenzenesulfonate (206 mg, 0.58 mmol), 4-methyl-2-(piperazin-1-yl)thiazole-5-carboxamide (131 mg, 0.58 mmol), potassium carbonate (120 mg, 0.87 mmol) and potassium iodide (20 mg, 0.12 mmol) in acetonitrile (15 mL) to give the title compound as a white solid (139 mg, 59%). The compound was characterized by the following spectroscopic data: LC-MS (ESI, pos. ion) m/z: 409.3 [M+H]$^+$ and $^1$H NMR (CDCl$_3$/CD$_3$OD=1/1, 400 MHz) δ (ppm): 7.94 (s, 1H), 7.43 (d, J=8.4 Hz, 1H), 7.15 (s, 1H), 7.11 (dd, J=8.4, 1.2 Hz, 1H), 3.54-3.52 (m, 4H), 2.80 (t, J=7.2 Hz, 2H), 2.58-2.56 (m, 4H), 2.50-2.47 (m, 5H), 1.97-1.89 (m, 2H).

Example 45 2-(4-(4-(5-Fluoro-1H-indol-3-yl)butyl)piperazin-1-yl)-4-methylthiazole-5-carbonitrile

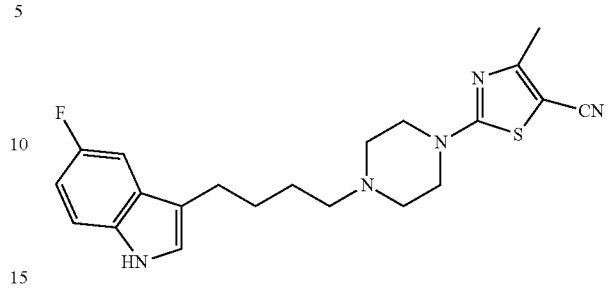

Step 1) 2-bromo-4-methylthiazole-5-carbonitrile

To a mixture of 2-bromo-4-methylthiazole-5-carboxamide (1.02 g, 4.60 mmol) in DCM (40 mL) was added TEA (1.6 mL, 11.50 mmol) at 0° C., and then added trifluoroacetic anhydride (1.2 mL) dropwise. After the reaction mixture was stirred at 0° C. for 0.5 hour, it was further stirred at rt for 3 hours. The reaction mixture was diluted with saturated aqueous sodium bicarbonate solution (120 mL) and extracted with DCM (90 mL×2). The combined organic phases were dried over anhydrous Na$_2$SO$_4$, filtered, concentrated in vacuo. and then dried to give the title compound as a red solid (0.88 g, 94%). The compound was characterized by the following spectroscopic data: GC-MS: 203.9 M$^+$ and $^1$H NMR (CDCl$_3$, 400 MHz) δ (ppm): 2.61 (s, 3H).

Step 2) 4-methyl-2-(piperazin-1-yl)thiazole-5-carbonitrile

The title compound was prepared by the procedure described in step 5 of example 1, using 2-bromo-4-methylthiazole-5-carbonitrile (1.46 g, 7.2 mmol), potassium carbonate (1.00 g, 7.2 mmol) and anhydrous piperazine (1.24 g, 14.4 mmol) in DMF (10 mL) to give the title compound as a yellow solid (1.47 g, 98.0%). The compound was characterized by the following spectroscopic data: LC-MS (ESI, pos. ion) m/z: 209.0 [M+H]$^+$ and $^1$H NMR (CD$_3$Cl, 400 MHz) δ (ppm): 3.51-3.49 (m, 4H), 2.97-2.95 (m, 4H), 2.38 (s, 3H).

Step 3) 2-(4-(4-(5-fluoro-1H-indol-3-yl)butyl)piperazin-1-yl)-4-methylthiazole-5-carbonitrile The title compound was prepared by the procedure described in step 6 of example 1, using 4-(5-fluoro-1H-indol-3-yl)butyl 4-methylbenzenesulfonate (210 mg, 0.58 mmol), 4-methyl-2-(piperazin-1-yl)thiazole-5-carbonitrile (120 mg, 0.58 mmol), potassium carbonate (120 mg, 0.87 mmol) and potassium iodide (20 mg, 0.12 mmol) in acetonitrile (15 mL) to give the title compound as a white solid (194 mg, 84%). The compound was characterized by the following spectroscopic data: LC-MS (ESI, pos. ion) m/z: 398.2 [M+H]$^+$ and $^1$H NMR (CDCl$_3$, 400 MHz) δ (ppm): 8.01 (br s, 1H), 7.30-7.23 (m, 2H), 7.04 (d, J=2.0 Hz, 1H), 6.95 (td, J=8.8, 2.4 Hz, 1H), 3.57-3.54 (m, 4H), 2.76 (t, J=7.2 Hz, 2H), 2.56-2.53 (m, 4H), 2.47-2.43 (m, 2H), 2.40 (s, 3H), 1.77-1.72 (m, 2H), 1.63-1.59 (m, 2H).

Example 46 2-(4-(3-(5-Fluoro-1H-indol-3-yl)propyl)piperazin-1-yl)-4-methylthiazole-5-carbonitrile

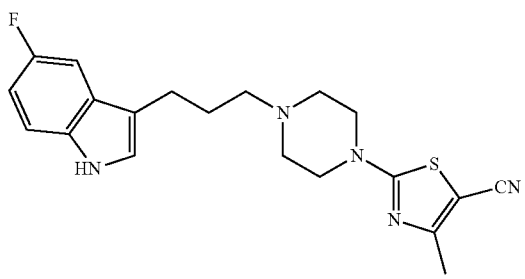 [SMILES: Cc1nc(N2CCN(CCCc3c[nH]c4ccc(F)cc34)CC2)sc1C#N]

The title compound was prepared by the procedure described in step 6 of example 1, using 3-(5-fluoro-1H-indol-3-yl)propyl 4-methylbenzenesulfonate (201 mg, 0.58 mmol), 4-methyl-2-(piperazin-1-yl)thiazole-5-carbonitrile (120 mg, 0.58 mmol), potassium carbonate (120 mg, 0.87 mmol) and potassium iodide (20 mg, 0.12 mmol) in acetonitrile (15 mL) to give the title compound as a white solid (188 mg, 85%). The compound was characterized by the following spectroscopic data: LC-MS (ESI, pos. ion) m/z: 384.2 [M+H]$^+$ and $^1$H NMR (CDCl$_3$, 400 MHz) δ (ppm): 8.10 (br s, 1H), 7.25-7.24 (m, 2H), 7.04 (d, J=2.0 Hz, 1H), 6.95 (td, J=8.8, 2.4 Hz, 1H), 3.59-3.56 (m, 4H), 2.78 (t, J=7.2 Hz, 2H), 2.57-2.55 (m, 4H), 2.50-2.47 (m, 2H), 2.41 (s, 3H), 1.96-1.90 (m, 2H).

Example 47 2-(4-(4-(5-Cyano-1H-indol-3-yl)butyl)piperazin-1-yl)-4-methylthiazole-5-carbonitrile

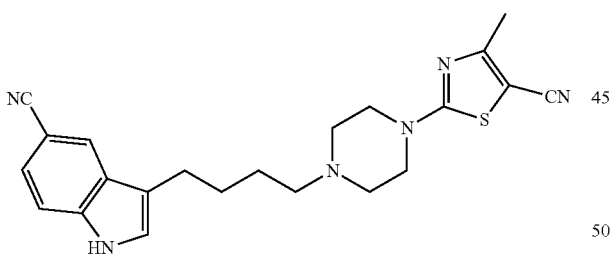

The title compound was prepared by the procedure described in step 6 of example 1, using 4-(5-cyano-1H-indol-3-yl)butyl 4-methylbenzenesulfonate (214 mg, 0.58 mmol), 4-methyl-2-(piperazin-1-yl)thiazole-5-carbonitrile (120 mg, 0.58 mmol), potassium carbonate (120 mg, 0.87 mmol) and potassium iodide (20 mg, 0.12 mmol) in acetonitrile (15 mL) to give the title compound as a white solid (182 mg, 78%). The compound was characterized by the following spectroscopic data: LC-MS (ESI, pos. ion) m/z: 405.1 [M+H]$^+$ and $^1$H NMR (CDCl$_3$, 400 MHz) δ (ppm): 8.41 (br s, 1H), 7.94 (s, 1H), 7.40-7.36 (m, 2H), 7.10-7.08 (m, 1H), 3.56-3.53 (m, 4H), 2.78 (t, J=7.2 Hz, 2H), 2.55-2.52 (m, 4H), 2.46-2.43 (m, 2H), 2.38 (s, 3H), 1.76-1.70 (m, 2H), 1.62-1.58 (m, 2H).

Example 48 2-(4-(3-(5-Cyano-1H-indol-3-yl)propyl)piperazin-1-yl)-4-methylthiazole-5-carbonitrile

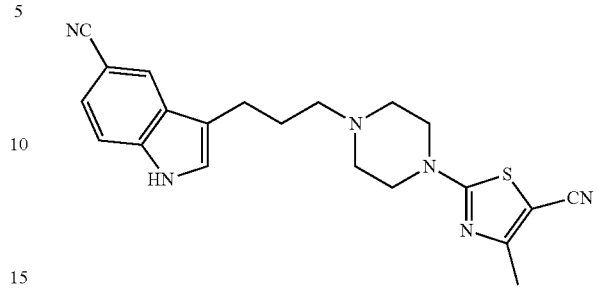

The title compound was prepared by the procedure described in step 6 of example 1, using 3-(5-cyano-1H-indol-3-yl)propyl 4-methylbenzenesulfonate (206 mg, 0.58 mmol), 4-methyl-2-(piperazin-1-yl)thiazole-5-carbonitrile (120 mg, 0.58 mmol), potassium carbonate (120 mg, 0.87 mmol) and potassium iodide (20 mg, 0.12 mmol) in acetonitrile (15 mL) to give the title compound as a white solid (181 mg, 80%). The compound was characterized by the following spectroscopic data: LC-MS (ESI, pos. ion) m/z: 391.1 [M+H]$^+$ and $^1$H NMR (CDCl$_3$, 400 MHz) δ (ppm): 8.49 (br s, 1H), 7.96 (s, 1H), 7.40-7.38 (m, 2H), 7.11-7.10 (m, 1H), 3.58-3.55 (m, 4H), 2.80 (t, J=7.2 Hz, 2H), 2.56-2.53 (m, 4H), 2.48-2.44 (m, 2H), 2.38 (s, 3H), 1.95-1.87 (m, 2H).

Example 49 2-(4-(3-(5-Cyano-1H-indol-3-yl)propyl)-3-methylpiperazin-1-yl)pyrimidine-4-carboxamide

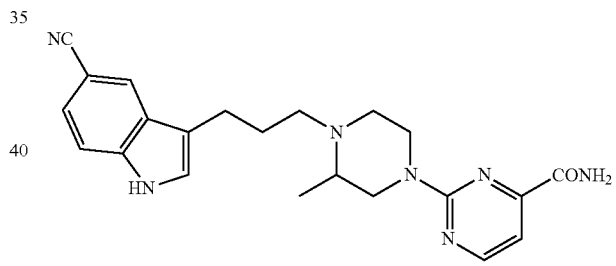

Step 1) 2-(3-methylpiperazin-1-yl)pyrimidine-4-carboxamide

The title compound was prepared by the procedure described in step 5 of example 1, using 2-chloropyrimidine-4-carboxamide (1.13 g, 7.2 mmol), potassium carbonate (1.00 g, 7.2 mmol) and 2-methylpiperazine (1.44 g, 14.4 mmol) in DMF (10 mL) to give the title compound as a yellow solid (1.03 g, 65.0%). The compound was characterized by the following spectroscopic data: LC-MS (ESI, pos. ion) m/z: 222.2 [M+H]$^+$ and $^1$H NMR (DMSO-d$_6$, 400 MHz) δ (ppm): 8.52 (d, J=4.6 Hz, 1H), 8.17 (br s, 1H), 7.75 (br s, 1H), 7.07 (d, J=4.6 Hz, 1H), 4.62 (s, 2H), 2.92 (d, J=11.7 Hz, 1H), 2.80 (td, J=11.8 Hz, 5.9 Hz, 1H), 2.62 (dd, J=11.5, 9.4 Hz, 2H), 2.43 (t, J=11.4 Hz, 1H), 1.02 (d, J=6.1 Hz, 3H).

Step 2) 2-(4-(3-(5-cyano-1H-indol-3-yl)propyl)-3-methylpiperazin-1-yl)pyrimidine-4-carboxamide The title compound was prepared by the procedure described in step 6 of example 1, using 3-(5-cyano-1H- indol-3-yl)propyl 4-methylbenzenesulfonate (206 mg, 0.58 mmol), 2-(3-methylpiperazin-1-yl)pyrimidine-4-carboxamide (128 mg, 0.58 mmol), potassium carbonate (120 mg, 0.87 mmol) and potassium iodide (20 mg, 0.12 mmol) in acetonitrile (15 mL) to give the title compound as a white solid (163 mg, 70.0%). The compound was characterized by the following spectroscopic data: LC-MS (ESI, pos. ion) m/z: 404.3 [M+H]$^+$ and $^1$H NMR (DMSO-d$_6$, 400 MHz) δ (ppm): 11.38 (s, 1H), 8.54 (d, J=4.8 Hz, 1H), 8.19 (s, 1H), 8.09 (s, 1H), 7.73 (s, 1H), 7.50 (d, J=8.4 Hz, 1H), 7.40 (dd, J=8.4, 1.2 Hz, 1H), 7.36 (d, J=1.1 Hz, 1H), 7.08 (d, J=4.8 Hz, 1H), 4.32 (d, J=1.6 Hz, 2H), 3.32-3.28 (m, 1H), 3.04-2.97 (m, 1H), 2.86 (d, J=9.8 Hz, 1H), 2.79-2.70 (m, 3H), 2.41-2.37 (m, 1H), 2.31-2.27 (m, 1H), 2.24-2.20 (m, 1H), 1.85-1.77 (m, 2H), 1.00 (d, J=5.9 Hz, 3H).

Example 50 2-(4-(4-(5-Cyano-1H-indol-3-yl)butyl)-3-methylpiperazin-1-yl)pyrimidine-4-carboxamide

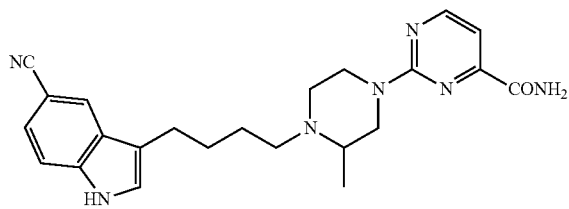 [SMILES: CC1CN(c2nccc(C(N)=O)n2)CCN1CCCCc1c[nH]c2ccc(C#N)cc12]

The title compound was prepared by the procedure described in step 6 of example 1, using 4-(5-cyano-1H-indol-3-yl)butyl 4-methylbenzenesulfonate (214 mg, 0.58 mmol), 2-(3-methylpiperazin-1-yl)pyrimidine-4-carboxamide (128 mg, 0.58 mmol), potassium carbonate (120 mg, 0.87 mmol) and potassium iodide (20 mg, 0.12 mmol) in acetonitrile (15 mL) to give the title compound as a white solid (164 mg, 68.0%). The compound was characterized by the following spectroscopic data: LC-MS (ESI, pos. ion) m/z: 418.3 [M+H]$^+$ and $^1$H NMR (DMSO-d$_6$, 400 MHz) δ (ppm): 11.37 (s, 1H), 8.53 (d, J=4.8 Hz, 1H), 8.19 (s, 1H), 8.09 (s, 1H), 7.74 (s, 1H), 7.50 (d, J=8.4 Hz, 1H), 7.40 (dd, J=8.4, 1.2 Hz, 1H), 7.34 (d, J=1.2 Hz, 1H), 7.08 (d, J=4.8 Hz, 1H), 4.32 (d, J=7.5 Hz, 2H), 3.27 (t, J=10.3 Hz, 1H), 2.97 (dd, J=12.2, 9.3 Hz, 1H), 2.83-2.79 (m, 1H), 2.76-2.72 (m, 3H), 2.37-2.33 (m, 1H), 2.25-2.20 (m, 1H), 2.16 (t, J=9.4 Hz, 1H), 1.70-1.60 (m, 2H), 1.52-1.47 (m, 2H), 1.03 (d, J=6.1 Hz, 3H).

BIOLOGICAL TEST

Example A: Evaluation of the Inhibitory Effect on [$^3$H]5-HT Uptake in Rat Synaptosome Test Method The synaptosomes (150 μg) prepared from the rat brain were incubated at 37° C. for 15 minutes with 0.1 μCi [$^3$H]5-HT in the absence or presence of the test compound or the reference compound in a buffer solution containing 106.2 mM NaCl, 4.5 mM KCl, 2.25 mM MgSO$_4$, 1.08 mM NaH$_2$PO$_4$, 22.5 mM NaHCO$_3$, 9.9 mM glucose, 9 μM EGTA and 45 μM ascorbic acid (pH 7.4).

The basal control activity was determined by incubating the same mixture at 4° C. for 15 minutes in the presence of 10 μM imipramine to block the uptake of 5-HT, which was taken as the standard reference compound and tested in each experiment at several concentrations to obtain an inhibition curve.

Following the incubation, the samples were filtered rapidly under vacuum through glass fiber filters (GF/B, Packard) and rinsed twice with an ice-cold incubation buffer using a 96-sample cell harvester (Unifilter, Packard) to eliminate free [$^3$H]5-HT. The filters were dried and the retained radioactivity was measured in a scintillation counter (Topcount, Packard) using a scintillation cocktail (Microscint 0, Packard). The experimental results were expressed as a percent inhibition of the control uptake of [$^3$H]5-HT.

Data Analysis

Inhibition of serotonin transporter in rat synaptosome was measured by the concentrations of [$^3$H]5-HT. The test compounds were required to be tested at least twice in the case of the concentration thereof being greater than 6 log, and the obtained data were subjected to a nonlinear regression analysis via a curve of Hill equation, to obtain IC$_{50}$ value. The experimental results of the compounds provided herein inhibiting [$^3$H]5-HT uptake in rat synaptosome were showed in Table 1.

TABLE 1

Inhibitory effect of the compounds provided herein on [$^3$H]5-HT uptake in rat synaptosome

| Example No. | IC$_{50}$ (nM) |
| --- | --- |
| 4 | 6.4 |
| 5 | 11 |
| 6 | 24 |
| 8 | 81 |
| 9 | 4.4 |
| 10 | 3.6 |
| 11 | 82 |
| 14 | 12 |
| 15 | 6.9 |
| 16 | 53 |
| 18 | 31 |
| 19 | 7.9 |
| 20 | 2.0 |
| 21 | 2.6 |
| 22 | 2.7 |
| 23 | 6.1 |
| 24 | 1.9 |
| 25 | 4.5 |
| 26 | 2.6 |
| 27 | 2.7 |
| 28 | 1.0 |
| 29 | 1.4 |
| 30 | 0.75 |
| 31 | 16 |
| 32 | 10 |
| 33 | 11 |
| 34 | 5.9 |
| 35 | 4.7 |
| 36 | 8.2 |
| 37 | 7.0 |
| 38 | 11 |
| 39 | 2.9 |
| 40 | 3.5 |
| 41 | 2.4 |
| 42 | 5.3 |
| 43 | 0.85 |
| 44 | 4.3 |
| 45 | 8.3 |
| 46 | 18 |
| 47 | 1.5 |
| 48 | 7.7 |
| 49 | 0.28 |
| 50 | 0.36 |

The experimental results indicated that the compounds provided herein exhibited potent inhibitory activity on 5-HT reuptake.

Example B: Evaluation of the Affinity for Human 5-HT$_{1A}$ Receptor

Test Method

Human HEK-293 cell homogenates (36 μg protein) were incubated at 22° C. for 60 minutes with 0.3 nM [$^3$H]8-OH-DPAT (Perkin-Elmer) in the absence or presence of the test compound in a buffer solution containing 50 mM Tris-HCl (pH 7.4), 10 mM MgSO$_4$, 0.5 mM EDTA, 2 μg/ml aprotinine.

The non-specific binding value was determined by incubating the same mixture in the presence of 10 μM 8-OH-DPAT, which was used as the standard reference compound and tested in each experiment at several concentrations to obtain a competition curve.

Following the incubation, the samples were filtered rapidly under vacuum through glass fiber filter (GF/B, Packard) presoaked with 0.3% PEI and rinsed several times with ice-cold 50 mM Tris-HCl using a 96-sample cell harvester (Unifilter, Packard). The filters were dried and the retained radioactivity was measured in a scintillation counter (Topcount, Packard) using a scintillation cocktail (Microscint 0, Packard). The experimental results were expressed as a percent inhibition of the control radioligand specific binding, and Ki was the inhibition constant.

Data Analysis

Binding assay of [$^3$H] 8-OH-DPAT (0.3 nM) with 5-HT$_{1A}$ receptor in human HEK-293 cell was tested by scintillation proximity assay of membrane. The test compounds were required to be tested at least three times in the case of the concentration thereof being greater than 6 log, and the obtained data were subjected to a nonlinear regression analysis via a curve of Hill equation, to obtain IC$_{50}$ value, and then calculated by ChengPrusoff equation to obtain Ki value. The experimental results of the binding affinity of the compounds provided herein for 5-HT$_{1A}$ receptor were showed in Table 2.

TABLE 2

Binding affinity of the compounds provided herein for 5-HT$_{1A}$ receptor

| Example No. | K$_i$ (nM) |
|---|---|
| 1 | 3.3 |
| 2 | 1.4 |
| 3 | 1.1 |
| 4 | 2.8 |
| 5 | 2.3 |
| 6 | 4.8 |
| 7 | 0.19 |
| 8 | 2.0 |
| 9 | 3.4 |
| 10 | 1.3 |
| 11 | 1.1 |
| 12 | 1.1 |
| 13 | 1.8 |
| 14 | 1.7 |
| 15 | 2.9 |
| 16 | 4.1 |
| 17 | 0.29 |
| 18 | 0.71 |
| 19 | 1.4 |
| 20 | 1.1 |
| 21 | 0.65 |

TABLE 2-continued

Binding affinity of the compounds provided herein for 5-HT$_{1A}$ receptor

| Example No. | K$_i$ (nM) |
|---|---|
| 22 | 1.5 |
| 23 | 18 |
| 24 | 6.2 |
| 25 | 4.0 |
| 26 | 8.0 |
| 27 | 60 |
| 28 | 10 |
| 29 | 12 |
| 30 | 14 |
| 31 | 2.0 |
| 32 | 0.7 |
| 33 | 1.0 |
| 34 | 0.2 |
| 37 | 5.5 |
| 38 | 0.27 |
| 39 | 0.79 |
| 40 | 0.3 |
| 41 | 23 |
| 42 | 4.5 |
| 43 | 12 |
| 44 | 3.7 |
| 45 | 14 |
| 46 | 4.2 |
| 47 | 5.0 |
| 48 | 2.6 |

The experimental results indicated that the compounds disclosed herein exhibited high binding affinity for 5-HT$_{1A}$ receptor.

Example C: Evaluation of the Affinity for Human Dopamine D$_{2S}$ Receptor

Test Method

Cell membrane homogenates (24 μg protein) were incubated at 22° C. for 60 minutes with 0.3 nM [3H]methylspiperone in the absence or presence of the test compound in a buffer solution containing 50 mM Tris-HCl (pH 7.4), 120 mM NaCl, 5 mM KCl, 5 mM MgCl2 and 1 mM EDTA.

The non-specific binding value was determined by incubating the same mixture in the presence of 10 μM (+)butaclamol.

Following the incubation, the samples were filtered rapidly under vacuum through glass fiber filter (GF/B, Packard) presoaked with 0.3% PEI and rinsed several times with ice-cold 50 mM Tris-HCl using a 96-sample cell harvester (Unifilter, Packard). The filters were dried and the retained radioactivity was measured in a scintillation counter (Topcount, Packard) using a scintillation cocktail (Microscint 0, Packard).

Data Analysis

The experimental results were expressed as a percent inhibition of the control radioligand specific binding, and Ki was the inhibition constant. The standard reference compound was (+)butaclamol, which was tested in each experiment at several concentrations to obtain a competition curve from which its IC$_{50}$ was calculated, and then Ki value was calculated by ChengPrusoff equation. The experimental results of the binding affinity of the compounds provided herein for D$_{2S}$ receptor were showed in Table 3.

TABLE 3

Binding affinity of the compounds provided herein for $D_{2S}$ receptor

| Example No. | $K_i$ (nM) |
|---|---|
| 4 | 110 |
| 10 | 200 |
| 16 | 110 |
| 26 | 190 |
| 27 | >1000 |
| 28 | 310 |
| 29 | 230 |
| 30 | >1000 |
| 37 | 130 |
| 38 | 270 |
| 40 | >1000 |
| 41 | 140 |
| 42 | 310 |
| 44 | >1000 |
| 45 | >1000 |
| 46 | >1000 |
| 47 | 130 |

The experimental results indicated that the compounds disclosed herein exhibited good selectivity for $D_{2S}$ receptor Example D: Pharmacokinetic Evaluation In vivo pharmacokinetic studies of the compounds disclosed herein in rats, dogs and monkeys were assessed. The compounds disclosed herein were administered in the form of a saline solution containing 5% DMSO, 5% Kolliphor HS 15, 2% (2% HCl) and 88% Saline, or the solution containing 10% DMSO, 10% Kolliphor HS 15 and 80% physiological saline. For intravenous administration, the animals were administered with a dose of 1 mg/kg, and 0.3 mL of blood was collected at the time points of 0.083, 0.25, 0.5, 1.0, 2.0, 4.0, 6.0, 8.0 and 24 h after drug administration (the time point of drug administration was set as 0 h). For oral (p.o.) administration, the animals were administered with a dose of 5 mg/kg, and 0.3 mL of blood was collected at the time points of 0.25, 0.5, 1.0, 2.0, 4.0, 6.0, 8.0 and 24 h after drug administration (the time point of drug administration was set as 0 h). All the blood samples were processed to separate plasma by centrifugation at 3000 rpm or 4000 rpm for 10 minutes. The plasma was collected and stored at −20° C. or −70° C. until LC/MS/MS analysis.

The experimental results indicated that the compounds disclosed herein exhibited good pharmacokinetic properties in rats, dogs and monkeys.

Reference throughout this specification to "one embodiment", "an embodiment", "some embodiments", "explanatory embodiment", "an example", "a specific example" or "some examples", means that a particular feature, structure, material or characteristic described in connection with the embodiment or example is included in at least one embodiment or example of the present disclosure. Thus, the appearances of the phrases such as "in some embodiments", "in one embodiment", "in an embodiment", "in another example", "in an example", "in a specific examples", or "in some examples" in various places throughout this specification are not necessarily referring to the same embodiment or example of the present disclosure. Furthermore, the particular features, structures, materials or characteristics may be combined in any suitable manner in one or more embodiments or examples. In addition, those skilled in the art can integrate and combine different embodiments, examples or the features of them as long as they are not contradictory to one another.

Although explanatory embodiments have been shown and described, it would be appreciated by those skilled in the art that the above embodiments can not be construed to limit the present disclosure, and changes, alternatives, and modifications can be made in the embodiments without departing from spirit, principles and scope of the present disclosure.

What is claimed is:

1. A compound having Formula (I) or a stereoisomer, a tautomer, an N-oxide, a solvate, or a pharmaceutically acceptable salt thereof,

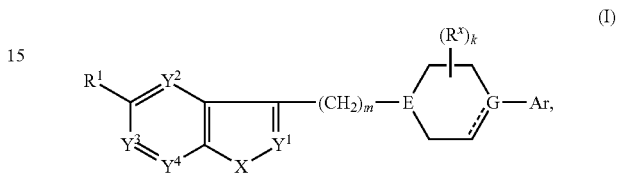

wherein
X is O, S or NH;
$Y^1$ is CH or N;
$Y^2$ is $CR^2$ or N;
$Y^3$ is $CR^3$ or N;
$Y^4$ is $CR^4$ or N;
E is N or CH;
==== is either a single bond or a double bond, provided that: (1) when ==== is a single bond, G is CH or N; or (2) when ==== is a double bond, G is C;
Ar is

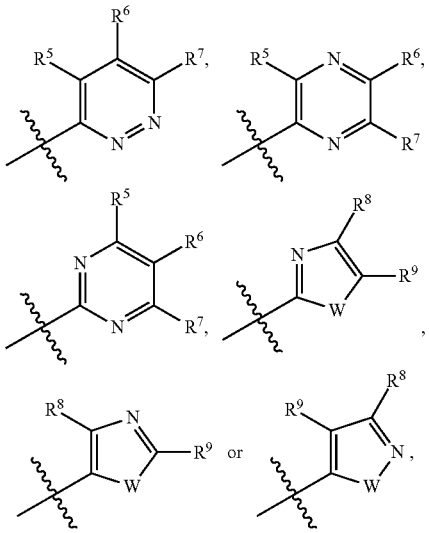

wherein each W is independently O or NH;
each $R^x$ is independently D, F, Cl, $C_1$-$C_6$ alkyl, $C_1$-$C_6$ haloalkyl, —$NR^{11}R^{11a}$, —$OR^{10}$, —($C_1$-$C_6$ alkylene)-$NR^{11}R^{11a}$, —($C_1$-$C_6$ alkylene)-$OR^{10}$, —C(=O)$R^{10}$, —C(=O)$OR^{10}$, —C(=O)$NR^{11}R^{11a}$ or —($C_1$-$C_6$ alkylene)-aryl, or two $R^x$ on two adjacent ring carbon atoms, together with the ring carbon atoms to which they are attached, form a $C_3$-$C_6$ carbocyclic or 3-6 membered heterocyclic ring;
k is 0, 1, 2, 3 or 4;
each of $R^1$, $R^2$, $R^3$ and $R^4$ is independently H, D, F, Cl, Br, I, $NO_2$, CN, —SCN, —$OR^{10}$, —$SR^{10}$, —$NR^{11}R^{11a}$, —C(=O)R¹⁰, —C(=O)OR¹⁰, —C(=O)NR¹¹R¹¹ᵃ, —OC(=O)R¹⁰, —S(=O)R¹⁰, —S(=O)₂R¹⁰, —S(=O)₂OR¹⁰, —S(=O)₂NR¹¹R¹¹ᵃ, —N(R¹¹)C(=O)R¹⁰, —N(R¹¹)S(=O)₂R¹⁰, alkyl, alkenyl, alkynyl, haloalkyl, cycloalkyl, cycloalkylalkylene, heterocyclyl, heterocyclylalkylene, aryl, arylalkylene, heteroaryl or heteroarylalkylene, wherein each of alkyl, alkenyl, alkynyl, haloalkyl, cycloalkyl, cycloalkylalkylene, heterocyclyl, heterocyclylalkylene, aryl, arylalkylene, heteroaryl and heteroarylalkylene is optionally substituted with one or more substituents independently selected from D, F, Cl, N₃, CN, OH, SH, NH₂, alkyl, alkoxy, alkylthio and alkylamino;

each R⁵, R⁶ and R⁷ is independently H, D, F, Cl, Br, I, NO₂, CN, NH₂, —C(=O)R¹⁰, —C(=O)OR¹⁰, —C(=O)NR¹¹R¹¹ᵃ, -alkylene-C(=O)NR¹¹R¹¹ᵃ, —OC(=O)R¹⁰, —N(R¹¹)C(=O)R¹⁰, —S(=O)R¹⁰, —S(=O)₂R¹⁰, —S(=O)₂OR¹⁰, —S(=O)₂NR¹¹R¹¹ᵃ, —N(R¹¹)S(=O)₂R¹⁰, alkyl, alkenyl, alkynyl, haloalkyl, alkoxy, alkylthio, alkylamino, cycloalkyl, cycloalkylalkylene, heterocyclyl, heterocyclylalkylene, aryl, arylalkylene, heteroaryl or heteroarylalkylene, with the proviso that at least one of R⁵, R⁶ and R⁷ is not H, wherein each of alkyl, alkenyl, alkynyl, haloalkyl, alkoxy, alkylthio, alkylamino, cycloalkyl, cycloalkylalkylene, heterocyclyl, heterocyclylalkylene, aryl, arylalkylene, heteroaryl and heteroarylalkylene is optionally substituted with one or more substituents independently selected from D, F, Cl, N₃, CN, OH, SH, NH₂, alkyl, alkoxy, alkylthio and alkylamino;

each R⁸ is independently H, D, alkyl, alkenyl, alkynyl, alkoxy or cycloalkyl, wherein each of alkenyl, alkynyl, alkoxy and cycloalkyl is optionally substituted with one or more substituents independently selected from D, F, Cl, N₃, CN, OH, SH, NH₂, alkyl, alkoxy, alkylthio, alkylamino, cycloalkyl, heterocyclyl, aryl and heteroaryl;

each R⁹ is independently F, Cl, Br, I, NO₂, CN, NH₂, —C(=O)R¹⁰, —C(=O)OR¹⁰, —C(=O)NR¹¹R¹¹ᵃ, —OC(=O)R¹⁰, —N(R¹¹)C(=O)R¹⁰, —S(=O)R¹⁰, —S(=O)₂R¹⁰, —S(=O)₂OR¹⁰, —S(=O)₂NR¹¹R¹¹ᵃ, —N(R¹¹)S(=O)₂R¹⁰, alkyl, alkenyl, alkynyl, haloalkyl, alkoxy, alkylthio, alkylamino, cycloalkyl, cycloalkylalkylene, heterocyclyl, heterocyclylalkylene, aryl, arylalkylene, heteroaryl or heteroarylalkylene, wherein each of alkyl, alkenyl, alkynyl, haloalkyl, alkoxy, alkylthio, alkylamino, cycloalkyl, cycloalkylalkylene, heterocyclyl, heterocyclylalkylene, aryl, arylalkylene, heteroaryl and heteroarylalkylene is optionally substituted with one or more substituents independently selected from D, F, Cl, N₃, CN, OH, SH, NH₂, alkyl, alkoxy, alkylthio and alkylamino;

each R¹⁰ is independently H, D, alkyl, alkenyl, alkynyl, haloalkyl, cycloalkyl, cycloalkylalkylene, heterocyclyl, heterocyclylalkylene, aryl, arylalkylene, heteroaryl or heteroarylalkylene, wherein each of alkyl, alkenyl, alkynyl, haloalkyl, cycloalkyl, cycloalkylalkylene, heterocyclyl, heterocyclylalkylene, aryl, arylalkylene, heteroaryl and heteroarylalkylene is optionally substituted with one or more substituents independently selected from D, F, Cl, N₃, CN, OH, SH, NH₂, alkyl, alkoxy, alkylthio and alkylamino;

each R¹¹ and R¹¹ᵃ is independently H, D, alkyl, alkenyl, alkynyl, haloalkyl, cycloalkyl, cycloalkylalkylene, heterocyclyl, heterocyclylalkylene, aryl, arylalkylene, heteroaryl or heteroarylalkylene, or R¹¹ and R¹¹ᵃ, together with the nitrogen atom to which they are attached, form a heterocyclic ring, wherein each of alkyl, alkenyl, alkynyl, haloalkyl, cycloalkyl, cycloalkylalkylene, heterocyclyl, heterocyclylalkylene, aryl, arylalkylene, heteroaryl, heteroarylalkylene and heterocyclic ring is optionally substituted with one or more substituents independently selected from D, F, Cl, N₃, CN, OH, SH, NH₂, alkyl, alkoxy, alkylthio and alkylamino; and m is 3, 4, 5 or 6.

2. The compound according to claim 1 having Formula (II) or a stereoisomer, a tautomer, an N-oxide, a solvate, or a pharmaceutically acceptable salt thereof,

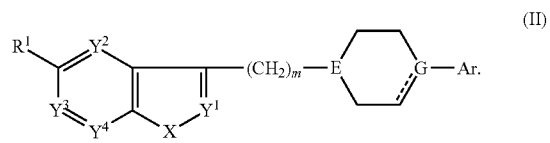

3. The compound according to claim 1, wherein each of R¹, R², R³ and R⁴ is independently H, D, F, Cl, NO₂, CN, —OR¹⁰, —SR¹⁰, —NR¹¹R¹¹ᵃ, —C(=O)R¹⁰, —C(=O)OR¹⁰, —C(=O)NR¹¹R¹¹ᵃ, —OC(=O)R¹⁰, —S(=O)R¹⁰, —S(=O)₂R¹⁰, —S(=O)₂OR¹⁰, —S(=O)₂NR¹¹R¹¹ᵃ, —N(R¹)C(=O)R¹⁰, —N(R¹¹)S(=O)₂R¹⁰, C₁-C₆ alkyl, C₂-C₆ alkenyl, C₂-C₆ alkynyl, C₁-C₆ haloalkyl, C₃-C₁₀ cycloalkyl, (C₃-C₁₀ cycloalkyl)-(C₁-C₆ alkylene)-, C₂-C₁₀ heterocyclyl, (C₂-C₁₀ heterocyclyl)-(C₁-C₆ alkylene)-, C₆-C₁₀ aryl, (C₆-C₁₀ aryl)-(C₁-C₆ alkylene)-, C₁-C₉ heteroaryl or (C₁-C₉ heteroaryl)-(C₁-C₆ alkylene)-, wherein each of C₁-C₆ alkyl, C₂-C₆ alkenyl, C₂-C₆ alkynyl, C₁-C₆ haloalkyl, C₃-C₁₀ cycloalkyl, (C₃-C₁₀ cycloalkyl)-(C₁-C₆ alkylene)-, C₂-C₁₀ heterocyclyl, (C₂-C₁₀ heterocyclyl)-(C₁-C₆ alkylene)-, C₆-C₁₀ aryl, (C₆-C₁₀ aryl)-(C₁-C₆ alkylene)-, C₁-C₉ heteroaryl and (C₁-C₉ heteroaryl)-(C₁-C₆ alkylene)- is optionally substituted with one or more substituents independently selected from D, F, Cl, N₃, CN, OH, SH, NH₂, C₁-C₆ alkyl, C₁-C₆ alkoxy, C₁-C₆ alkylthio and C₁-C₆ alkylamino; or wherein each of R¹, R², R³ and R⁴ is independently H, D, F, Cl, NO₂, CN, —OR¹⁰, —SR¹⁰, —NR¹¹R¹¹ᵃ, C₁-C₄ alkyl, C₁-C₄ haloalkyl, C₃-C₈ cycloalkyl, (C₃-C₈ cycloalkyl)-(C₁-C₄ alkylene)-, C₂-C₇ heterocyclyl, (C₂-C₇ heterocyclyl)-(C₁-C₄ alkylene)-, phenyl, (phenyl)-(C₁-C₄ alkylene)-, C₁-C₅ heteroaryl or (C₁-C₅ heteroaryl)-(C₁-C₄ alkylene)-, wherein each of C₁-C₄ alkyl, C₁-C₄ haloalkyl, C₃-C₈ cycloalkyl, (C₃-C₈ cycloalkyl)-(C₁-C₄ alkylene)-, C₂-C₇ heterocyclyl, (C₂-C₇ heterocyclyl)-(C₁-C₄ alkylene)-, phenyl, (phenyl)-(C₁-C₄ alkylene)-, C₁-C₅ heteroaryl and (C₁-C₅ heteroaryl)-(C₁-C₄ alkylene)- is optionally substituted with one or more substituents independently selected from D, F, Cl, N₃, CN, OH, SH, NH₂, C₁-C₄ alkyl, C₁-C₄ alkoxy, C₁-C₄ alkylthio and C₁-C₄ alkylamino.

4. The compound according to claim 1, wherein each R⁵, R⁶ and R⁷ is independently H, D, F, Cl, NO₂, CN, NH₂, —C(=O)R¹⁰, —C(=O)OR¹⁰, —C(=O)NR¹¹R¹¹ᵃ, —(C₁-C₆ alkylene)-C(=O)NR¹¹R¹¹ᵃ, —OC(=O)R¹⁰, —N(R¹¹)C(=O)R¹⁰, —S(=O)R¹⁰, —S(=O)₂R¹⁰, —S(=O)₂OR¹⁰, —S(=O)₂NR¹¹R¹¹ᵃ, —N(R¹¹)S(=O)₂R¹⁰, C₁-C₆ alkyl, C₂-C₆ alkenyl, C₂-C₆ alkynyl, C₁-C₆ haloalkyl, C₁-C₆ alkoxy, C₁-C₆ alkylthio, C₁-C₆ alkylamino, C₃-C₁₀ cycloalkyl, (C₃-C₁₀ cycloalkyl)-(C₁-C₆ alkylene)-, C₂-C₁₀ heterocyclyl, (C₂-C₁₀ heterocyclyl)-(C₁-C₆ alkylene)-, C₆-C₁₀ aryl, (C₆-C₁₀ aryl)-(C₁-C₆ alkylene)-, C₁-C₉ heteroaryl or (C₁-C₉ heteroaryl)-(C₁-C₆ alkylene)-, with the proviso that at least one of $R^5$, $R^6$ and $R^7$ is not H, wherein each of $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ alkylthio, $C_1$-$C_6$ alkylamino, $C_3$-$C_{10}$ cycloalkyl, ($C_3$-$C_{10}$ cycloalkyl)-($C_1$-$C_6$ alkylene)-, $C_2$-$C_{10}$ heterocyclyl, ($C_2$-$C_{10}$ heterocyclyl)-($C_1$-$C_6$ alkylene)-, $C_6$-$C_{10}$ aryl, ($C_6$-$C_{10}$ aryl)-($C_1$-$C_6$ alkylene)-, $C_1$-$C_9$ heteroaryl and ($C_1$-$C_9$ heteroaryl)-($C_1$-$C_6$ alkylene)- is optionally substituted with one or more substituents independently selected from D, F, Cl, $N_3$, CN, OH, SH, $NH_2$, $C_1$-$C_6$ alkyl, $C_1$-$C_6$ alkoxy, $C_1$-$C_6$ alkylthio and $C_1$-$C_6$ alkylamino; or wherein each $R^5$, $R^6$ and $R^7$ is independently H, D, F, Cl, $NO_2$, CN, $NH_2$, —C(=O)$R^{10}$, —C(=O)O$R^{10}$, —C(=O)N$R^{11}R^{11a}$, —($C_1$-$C_4$ alkylene)-C(=O)N$R^{11}R^{11a}$, —OC(=O)$R^{10}$, —N($R^{11}$)C(=O)$R^{10}$, —S(=O)$R^{10}$, —S(=O)$_2R^{10}$, —S(=O)$_2$O$R^{10}$, —S(=O)$_2$N$R^{11}R^{11a}$, —N($R^{11}$)S(=O)$_2R^{10}$, $C_1$-$C_4$ alkyl, $C_1$-$C_4$ haloalkyl, $C_1$-$C_4$ alkoxy, $C_1$-$C_4$ alkylthio or $C_1$-$C_4$ alkylamino, with the proviso that at least one of $R^5$, $R^6$ and $R^7$ is not H, wherein each of $C_1$-$C_4$ alkyl, $C_1$-$C_4$ haloalkyl, $C_1$-$C_4$ alkoxy, $C_1$-$C_4$ alkylthio and $C_1$-$C_4$ alkylamino is optionally substituted with one or more substituents independently selected from D, F, Cl, $N_3$, CN, OH, SH, $NH_2$, $C_1$-$C_4$ alkyl, $C_1$-$C_4$ alkoxy, $C_1$-$C_4$ alkylthio and $C_1$-$C_4$ alkylamino.

5. The compound according to claim 1, wherein each $R^{10}$ is independently H, D, $C_1$-$C_6$ alkyl, $C_1$-$C_6$ haloalkyl or $C_3$-$C_{10}$ cycloalkyl, wherein each of $C_1$-$C_6$ alkyl, $C_1$-$C_6$ haloalkyl and $C_3$-$C_{10}$ cycloalkyl is optionally substituted with one or more substituents independently selected from D, F, Cl, $N_3$, CN, OH, SH, $NH_2$, $C_1$-$C_6$ alkyl, $C_1$-$C_6$ alkoxy, $C_1$-$C_6$ alkylthio and $C_1$-$C_6$ alkylamino; and each $R^{11}$ and $R^{11a}$ is independently H, D, $C_1$-$C_6$ alkyl, $C_1$-$C_6$ haloalkyl or $C_3$-$C_{10}$ cycloalkyl, or $R^{11}$ and $R^{11a}$, together with the nitrogen atom to which they are attached, form a $C_2$-$C_{10}$ heterocyclic ring, wherein each of $C_1$-$C_6$ alkyl, $C_1$-$C_6$ haloalkyl, $C_3$-$C_{10}$ cycloalkyl and $C_2$-$C_{10}$ heterocyclic ring is optionally substituted with one or more substituents independently selected from D, F, Cl, $N_3$, CN, OH, SH, $NH_2$, $C_1$-$C_6$ alkyl, $C_1$-$C_6$ alkoxy, $C_1$-$C_6$ alkylthio and $C_1$-$C_6$ alkylamino.

6. The compound according to claim 1 having Formula (III):

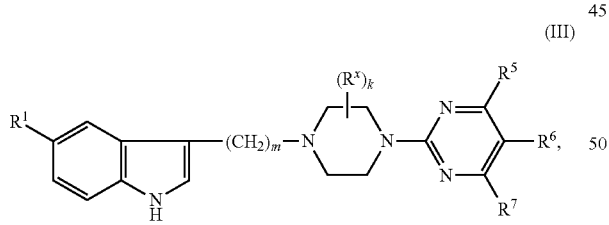

(III)

wherein
each $R^x$ is independently D, Cl, Me, —CF$_3$, —OMe, OH or $NH_2$;
k is 0, 1, 2, 3 or 4;
$R^1$ is H, D, F, Cl, CN, —O$R^{10}$, —N$R^{11}R^{11a}$, $C_1$-$C_4$ alkyl, $C_1$-$C_4$ haloalkyl, $C_3$-$C_8$ cycloalkyl, $C_2$-$C_7$ heterocyclyl, phenyl or $C_1$-$C_5$ heteroaryl, wherein each of $C_1$-$C_4$ alkyl, $C_1$-$C_4$ haloalkyl, $C_3$-$C_8$ cycloalkyl, $C_2$-$C_7$ heterocyclyl, phenyl and $C_1$-$C_5$ heteroaryl is optionally substituted with one or more substituents independently selected from D, F, Cl, $N_3$, CN, OH, SH, $NH_2$, $C_1$-$C_4$ alkyl, $C_1$-$C_4$ alkoxy, $C_1$-$C_4$ alkylthio and $C_1$-$C_4$ alkylamino;

each of $R^5$, $R^6$ and $R^7$ is independently H, D, F, Cl, $NO_2$, CN, $NH_2$, —C(=O)$R^{10}$, —C(=O)O$R^{10}$, —C(=O)N$R^{11}R^{11a}$, —($C_1$-$C_4$ alkylene)-C(=O)N$R^{11}R^{11a}$, —OC(=O)$R^{10}$, $C_1$-$C_4$ alkyl, $C_1$-$C_4$ haloalkyl, $C_1$-$C_4$ alkoxy, $C_1$-$C_4$ alkylthio or $C_1$-$C_4$ alkylamino, with the proviso that at least one of $R^5$, $R^6$ and $R^7$ is not H, wherein each of $C_1$-$C_4$ alkyl, $C_1$-$C_4$ haloalkyl, $C_1$-$C_4$ alkoxy, $C_1$-$C_4$ alkylthio and $C_1$-$C_4$ alkylamino is optionally substituted with one or more substituents independently selected from D, F, Cl, $N_3$, CN, OH, SH, $NH_2$, $C_1$-$C_4$ alkyl, $C_1$-$C_4$ alkoxy, $C_1$-$C_4$ alkylthio and $C_1$-$C_4$ alkylamino;

each $R^{10}$ is independently H, D, $C_1$-$C_4$ alkyl, $C_1$-$C_4$ haloalkyl or $C_3$-$C_8$ cycloalkyl;

each $R^{11}$ and $R^{11a}$ is independently H, D, $C_1$-$C_4$ alkyl, $C_1$-$C_4$ haloalkyl or $C_3$-$C_8$ cycloalkyl, or $R^{11}$ and $R^{11a}$, together with the nitrogen atom to which they are attached, form a $C_2$-$C_7$ heterocyclic ring; and m is 3, 4, 5 or 6.

7. The compound according to claim 6 having Formula (IV):

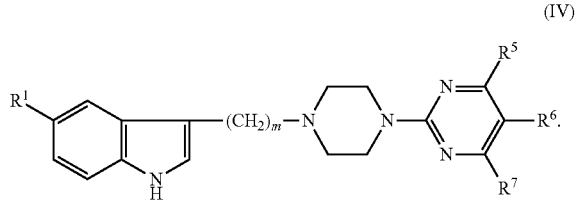

(IV)

8. The compound according to claim 6, wherein $R^1$ is H, D, F, Cl, CN, OH, $NH_2$, Me, Et, n-Pr, i-Pr, —CF$_3$, —OMe, —OEt, —O(i-Pr), —O(t-Bu) or —NMe$_2$.

9. The compound according to claim 6, wherein each of $R^5$, $R^6$ and $R^7$ is independently H, D, F, Cl, $NO_2$, CN, $NH_2$, —C(=O)H, —C(=O)OH, —C(=O)OMe, —C(=O)NH$_2$, —CH$_2$—C(=O)NH$_2$, —C(=O)NMe$_2$, Me, Et, n-Pr, i-Pr, —CF$_3$, —OMe, —OEt, —O(i-Pr), —O(t-Bu) or —NMe$_2$, with the proviso that at least one of $R^5$, $R^6$ and $R^7$ is not H.

10. A compound having one of the following structures:

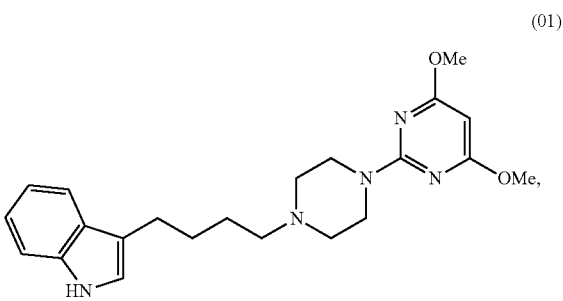

(O1)

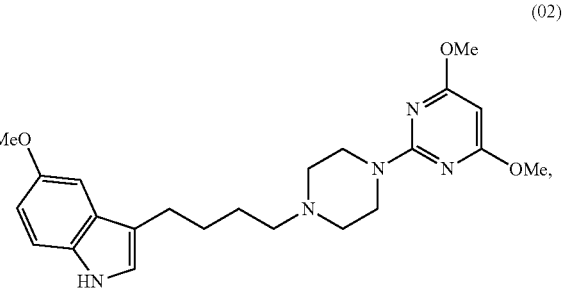

(O2)

(03)
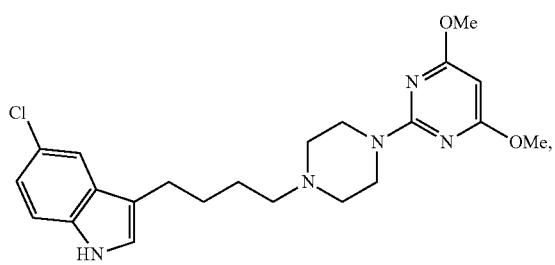
(04)
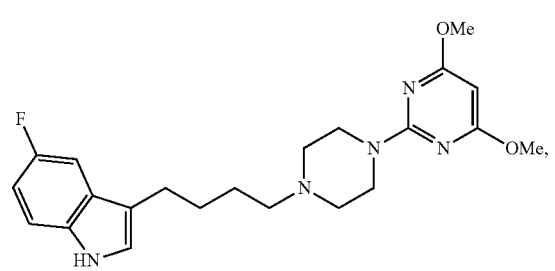
(05)
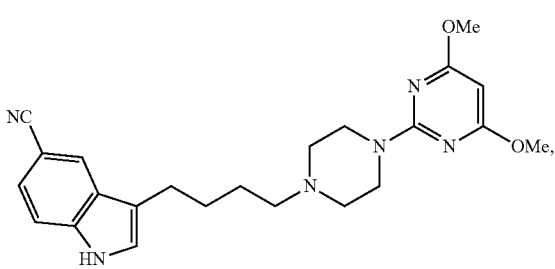
(06)
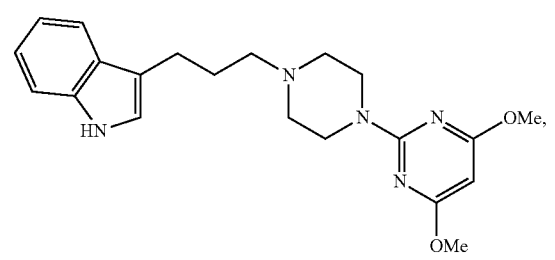
(07)
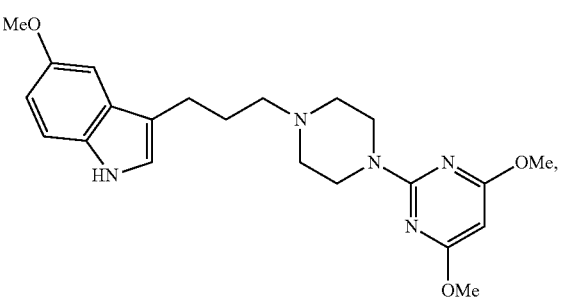
(08)
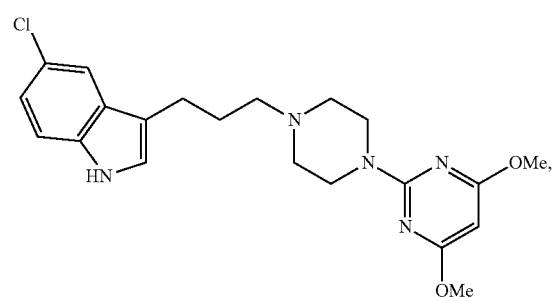
(09)
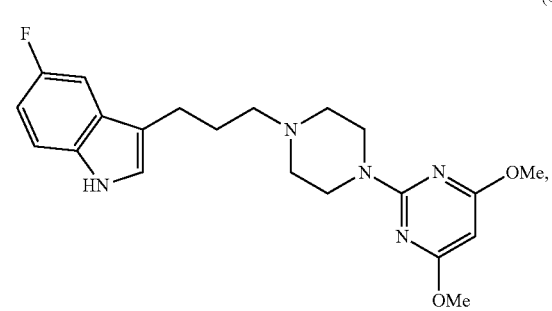
(10)
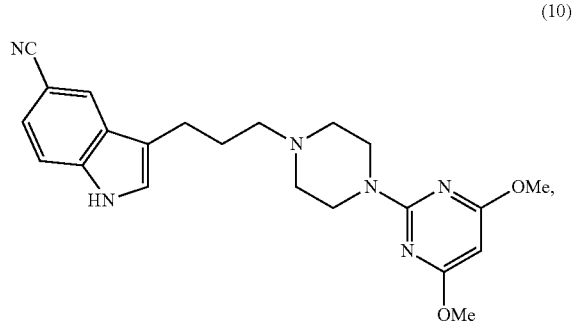
(11)
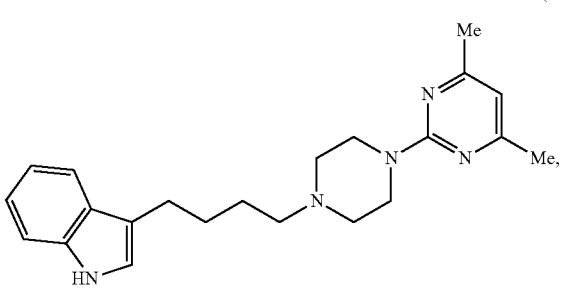
(12)
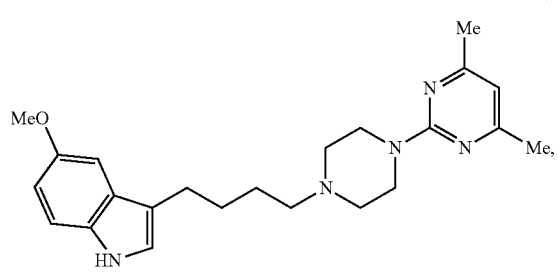

(13) 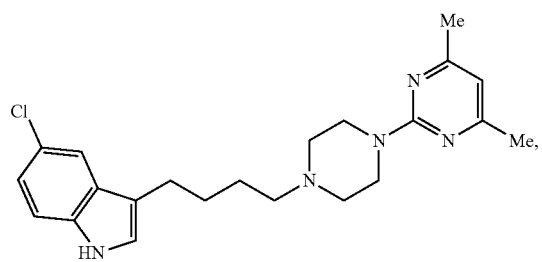
(14) 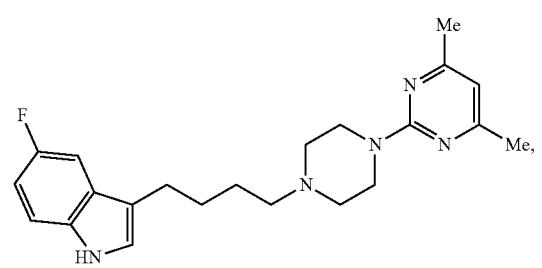
(15) 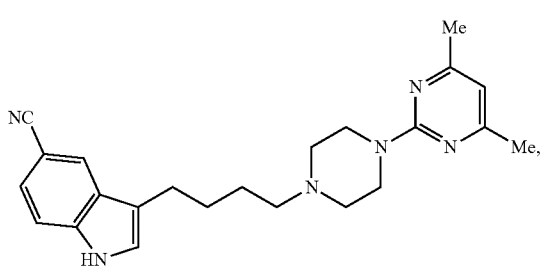
(16) 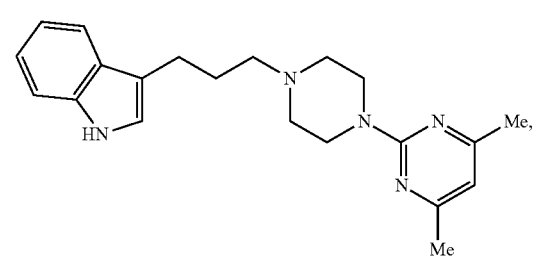
(17) 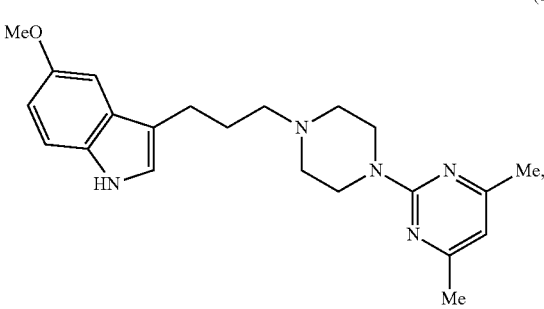
(18) 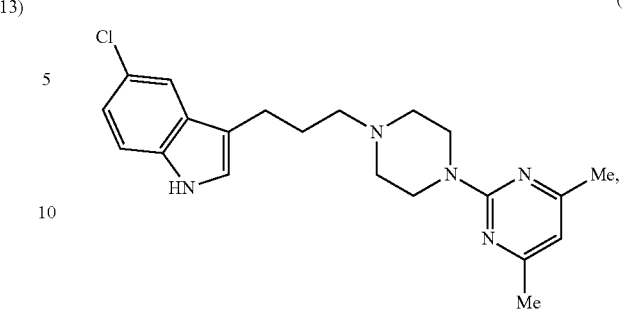
(19) 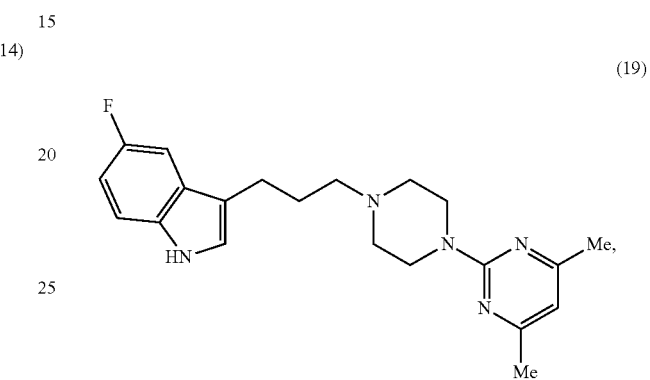
(20) 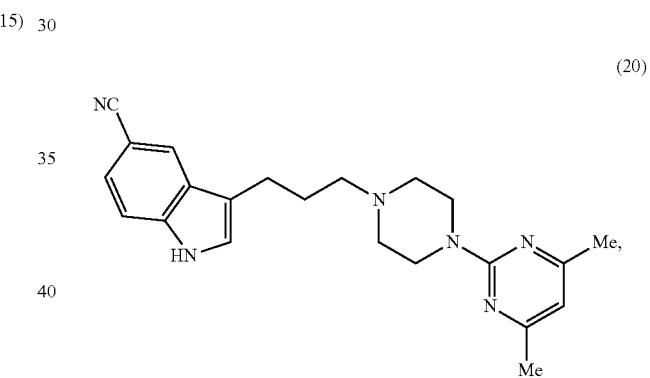
(21) 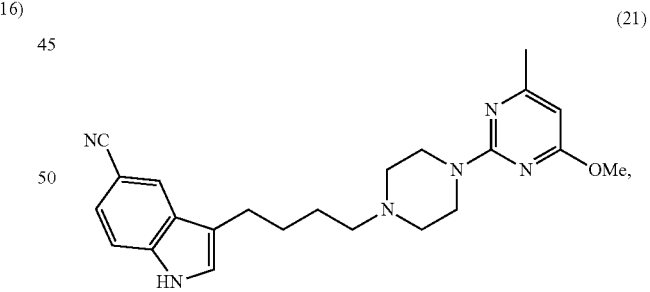
(22) 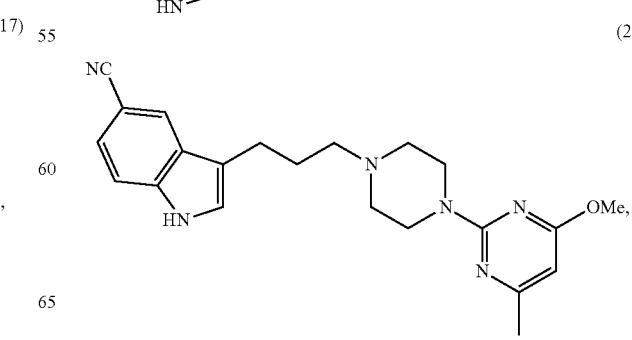

(23)
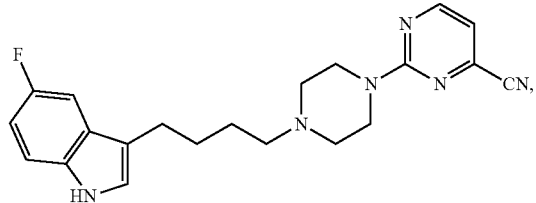
(24)
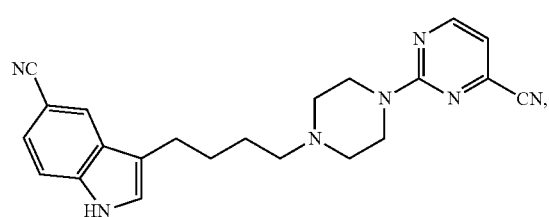
(25)
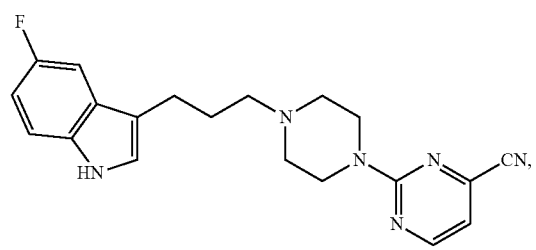
(26)
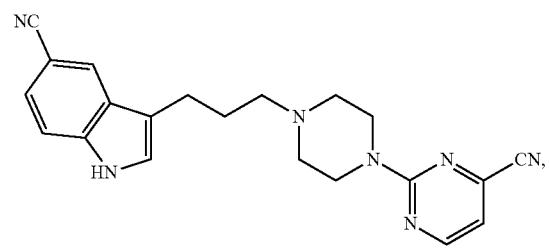
(27)
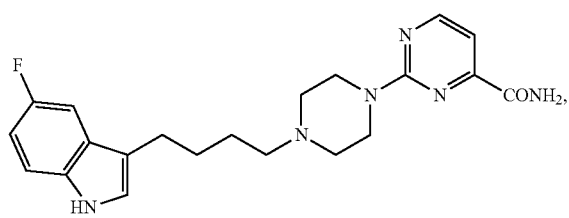
(28)
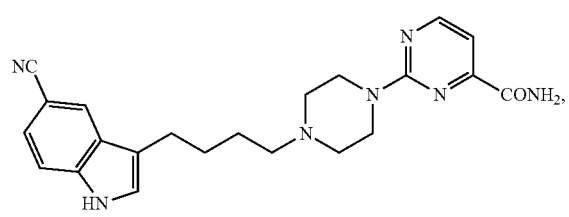
(29)
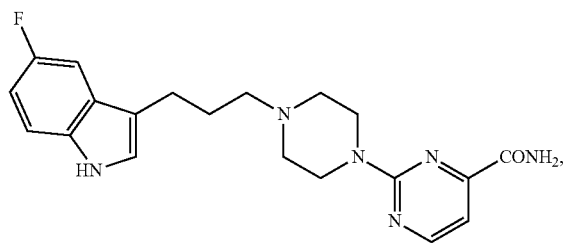
(30)
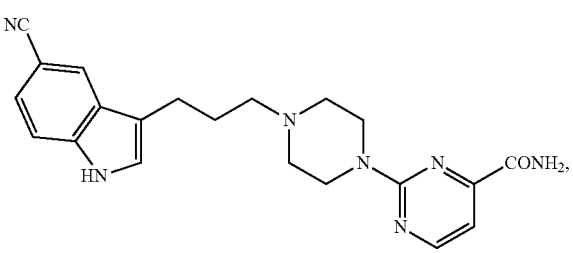
(31)
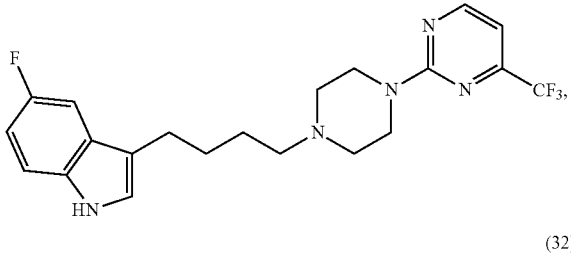
(32)
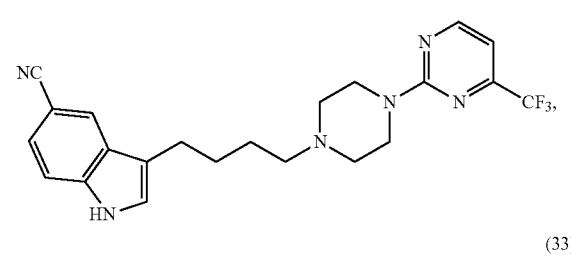
(33)
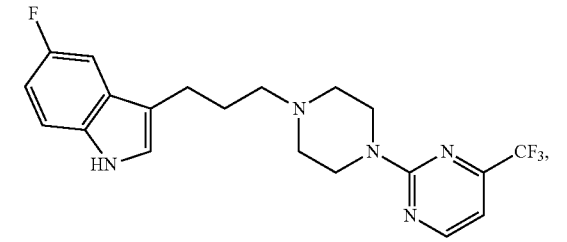
(34)
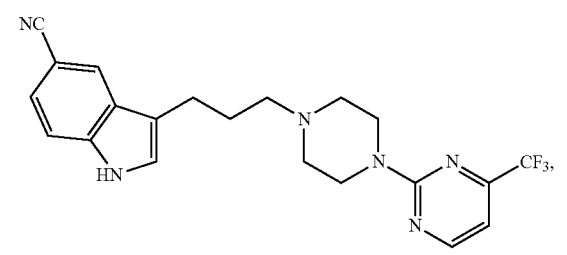

(35) 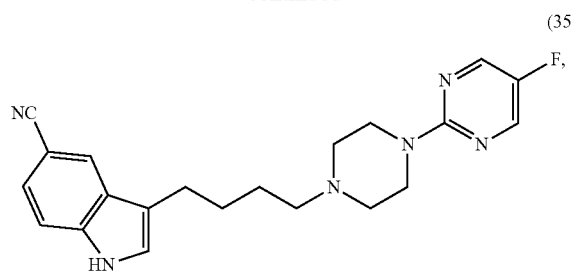
(36) 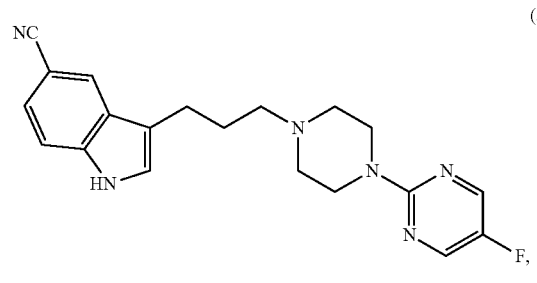
(37) 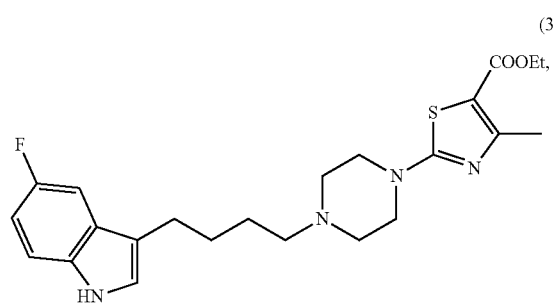
(38) 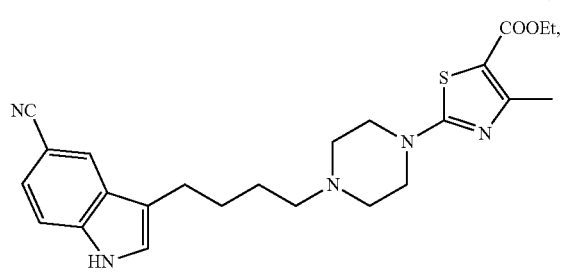
(39) 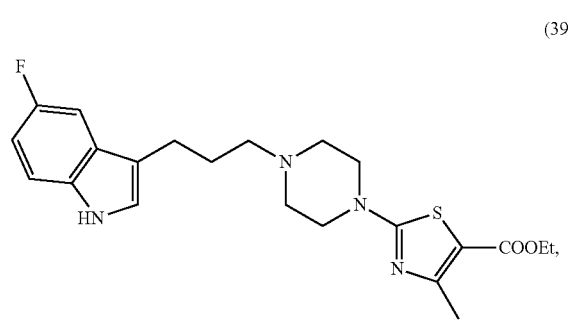
(40) 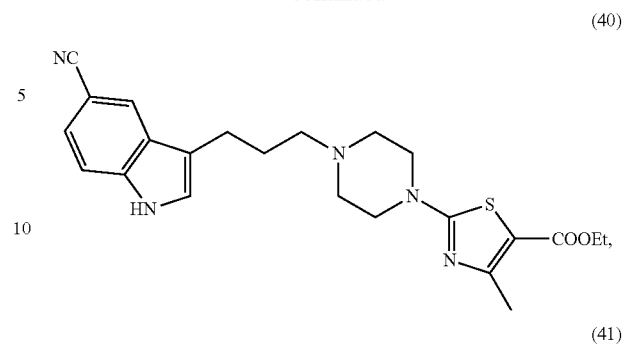
(41) 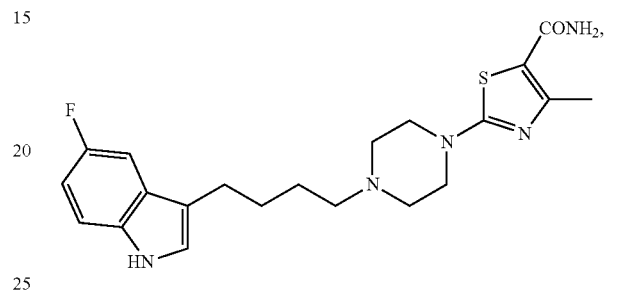
(42) 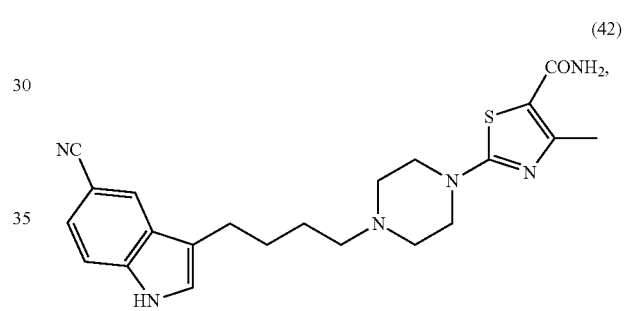
(43) 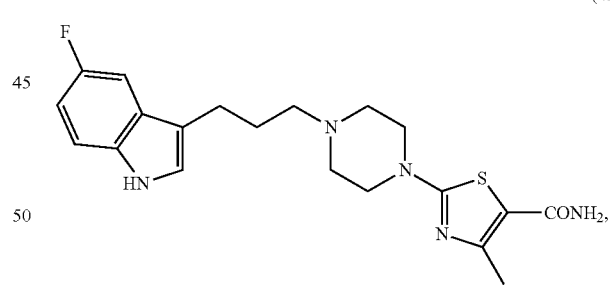
(44) 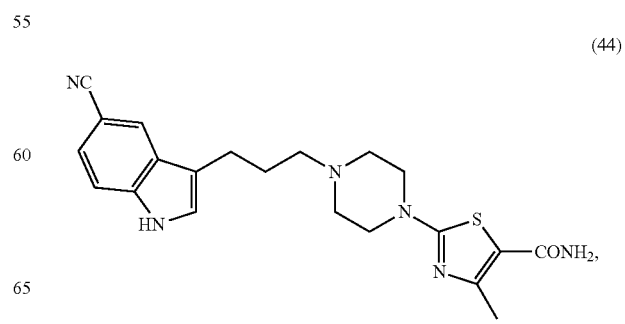

(45) 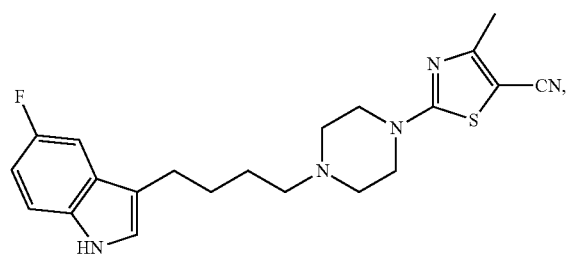
(46) 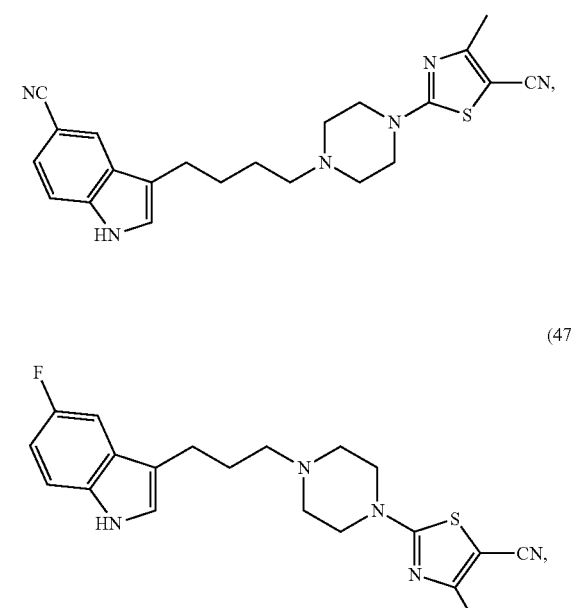
(47)
(48) 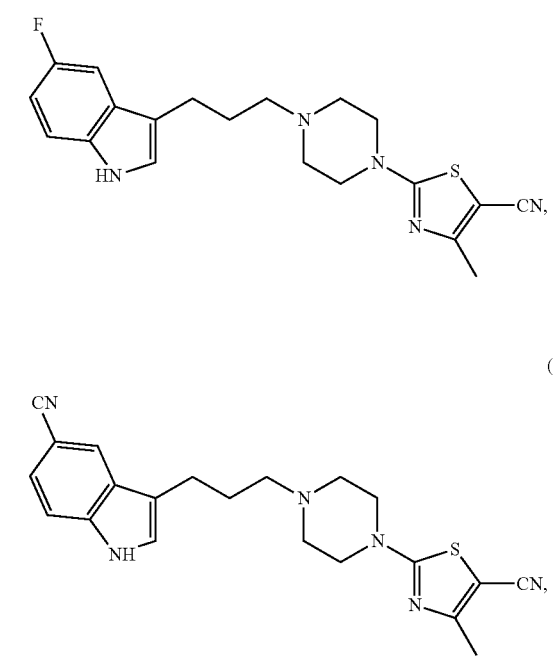
(49) 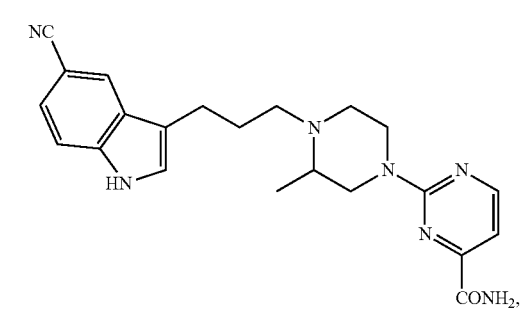
(50) 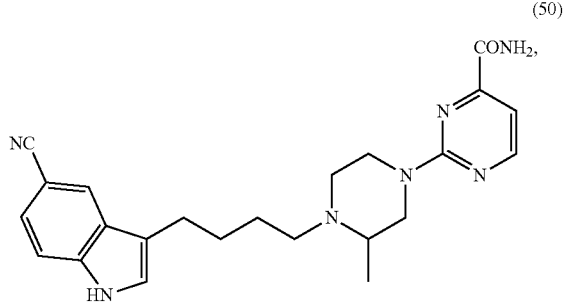
(51) 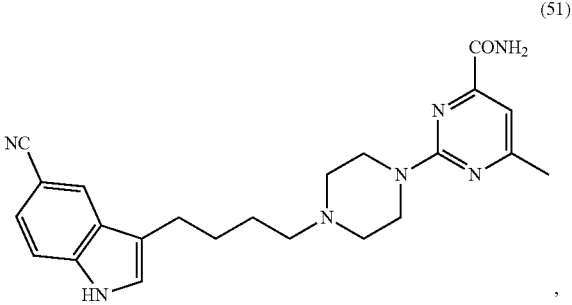
(52) 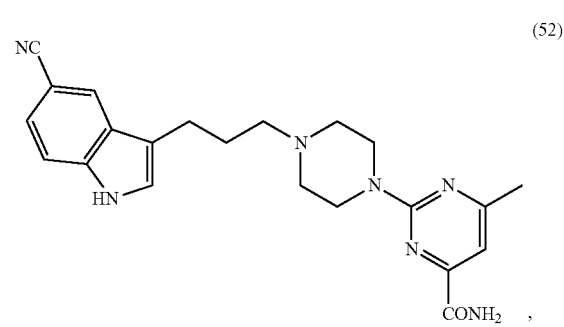
(53) 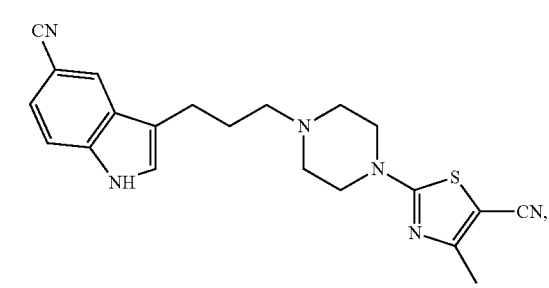
(54) 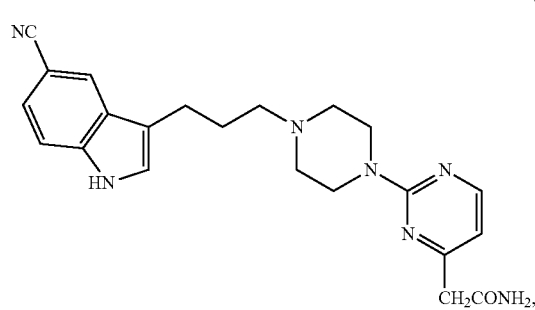

-continued

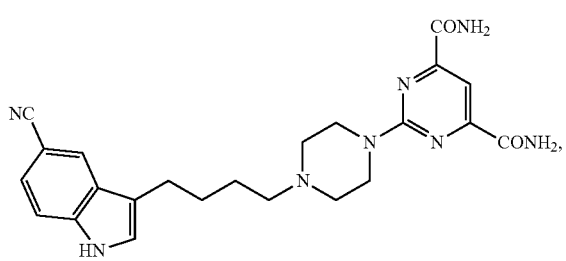

(55)

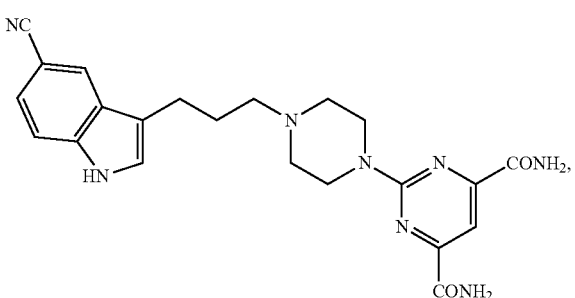

(56)

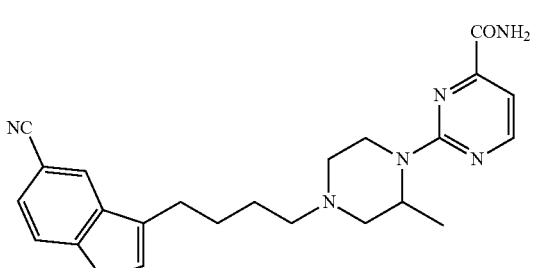

(57)

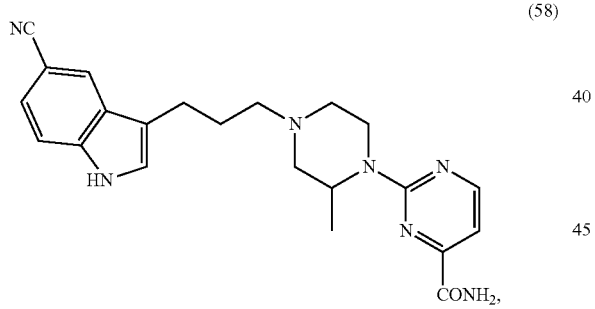

(58)

or a stereoisomer, a tautomer, an N-oxide, a solvate, or a pharmaceutically acceptable salt thereof.

11. A pharmaceutical composition comprising the compound according to claim 1, and a pharmaceutically acceptable excipient, carrier, adjuvant or a combination thereof.

12. The pharmaceutical composition according to claim 11, further comprising at least one therapeutic agent for central nervous system dysfunction, wherein the therapeutic agent for central nervous system dysfunction is an antidepressant, an antianxiety agent, a lithium agent of a mood stabilizer, an atypical antipsychotic agent, an antiepileptic agent, an anti-Parkinson agent, a selective serotonin reuptake inhibitor, a 5-$HT_{1A}$ receptor agonist, a central nervous system stimulant, a nicotine antagonist or a combination thereof; or wherein the therapeutic agent for central nervous system dysfunction is amitriptyline, desipramine, mirtazapine, bupropion, reboxetine, fluoxetine, trazodone, sertraline, duloxetine, fluvoxamine, milnacipran, levomilnacipran, desvenlafaxine, vilazodone, venlafaxine, dapoxetine, nefazodone, femoxetine, clomipramine, citalopram, escitalopram, paroxetine, lithium carbonate, buspirone, olanzapine, quetiapine, risperidone, ziprasidone, aripiprazole, perospirone, clozapine, modafinil, mecamylamine, cabergoline, adamantane, imipramine, pramipexole, thyroxine, dextromethorphan, quinidine, naltrexone, samidorphan, buprenorphine, melatonin, alprazolam, pipamperone, vestipitant, chlordiazepoxide, perphenazine or a combination thereof.

13. A method of treating or lessening the severity of a central nervous system dysfunction in a human comprising administrating a therapeutically effective amount of the compound according to claim 1 to the human, wherein the central nervous system dysfunction is depression, anxiety, mania, schizophrenia, bipolar disorder, obsessive compulsive disorder, panic disorder, post-traumatic stress disorder, Parkinson's disease, and Huntington's disease.

14. A method of treating or lessening the severity of a central nervous system dysfunction in a human comprising administrating a therapeutically effective amount of the pharmaceutical composition according to claim 11 to the human, wherein the central nervous system dysfunction is depression, anxiety, mania, schizophrenia, bipolar disorder, obsessive compulsive disorder, panic disorder, post-traumatic stress disorder, Parkinson's disease, and Huntington's disease.

15. The compound according to claim 2, wherein each of $R^1$, $R^2$, $R^3$ and $R^4$ is independently H, D, F, Cl, $NO_2$, CN, —$OR^{10}$, —$SR^{10}$, —$NR^{11}R^{11a}$, —C(=O)$R^{10}$, —C(=O)$OR^{10}$, —C(=O)$NR^{11}R^{11a}$, —OC(=O)$R^{10}$, —S(=O)$R^{10}$, —S(=O)$_2R^{10}$, —S(=O)$_2OR^{10}$, —S(=O)$_2NR^{11}R^{11a}$, —N($R^{11}$)C(=O)$R^{10}$, —N($R^{11}$)S(=O)$_2R^{10}$, $C_1$-$C_6$ alkyl, $C_2$-$C_6$ alkenyl, $C_2$-$C_6$ alkynyl, $C_1$-$C_6$ haloalkyl, $C_3$-$C_{10}$ cycloalkyl, ($C_3$-$C_{10}$ cycloalkyl)-($C_1$-$C_6$ alkylene)-, $C_2$-$C_{10}$ heterocyclyl, ($C_2$-$C_{10}$ heterocyclyl)-($C_1$-$C_6$ alkylene)-, $C_6$-$C_{10}$ aryl, ($C_6$-$C_{10}$ aryl)-($C_1$-$C_6$ alkylene)-, $C_1$-$C_9$ heteroaryl or ($C_1$-$C_9$ heteroaryl)-($C_1$-$C_6$ alkylene)-, wherein each of $C_1$-$C_6$ alkyl, $C_2$-$C_6$ alkenyl, $C_2$-$C_6$ alkynyl, $C_1$-$C_6$ haloalkyl, $C_3$-$C_{10}$ cycloalkyl, ($C_3$-$C_{10}$ cycloalkyl)-($C_1$-$C_6$ alkylene)-, $C_2$-$C_{10}$ heterocyclyl, ($C_2$-$C_{10}$ heterocyclyl)-($C_1$-$C_6$ alkylene)-, $C_6$-$C_{10}$ aryl, ($C_6$-$C_{10}$ aryl)-($C_1$-$C_6$ alkylene)-, $C_1$-$C_9$ heteroaryl and ($C_1$-$C_9$ heteroaryl)-($C_1$-$C_6$ alkylene)- is optionally substituted with one or more substituents independently selected from D, F, Cl, $N_3$, CN, OH, SH, $NH_2$, $C_1$-$C_6$ alkyl, $C_1$-$C_6$ alkoxy, $C_1$-$C_6$ alkylthio and $C_1$-$C_6$ alkylamino; or wherein each of $R^1$, $R^2$, $R^3$ and $R^4$ is independently H, D, F, Cl, $NO_2$, CN, —$OR^{10}$, —$SR^{10}$, —$NR^{11}R^{11a}$, $C_1$-$C_4$ alkyl, $C_1$-$C_4$ haloalkyl, $C_3$-$C_8$ cycloalkyl, ($C_3$-$C_8$ cycloalkyl)-($C_1$-$C_4$ alkylene)-, $C_2$-$C_7$ heterocyclyl, ($C_2$-$C_7$ heterocyclyl)-($C_1$-$C_4$ alkylene)-, phenyl, (phenyl)-($C_1$-$C_4$ alkylene)-, $C_1$-$C_5$ heteroaryl or ($C_1$-$C_5$ heteroaryl)-($C_1$-$C_4$ alkylene)-, wherein each of $C_1$-$C_4$ alkyl, $C_1$-$C_4$ haloalkyl, $C_3$-$C_8$ cycloalkyl, ($C_3$-$C_8$ cycloalkyl)-($C_1$-$C_4$ alkylene)-, $C_2$-$C_7$ heterocyclyl, ($C_2$-$C_7$ heterocyclyl)-($C_1$-$C_4$ alkylene)-, phenyl, (phenyl)-($C_1$-$C_4$ alkylene)-, $C_1$-$C_5$ heteroaryl and ($C_1$-$C_5$ heteroaryl)-($C_1$-$C_4$ alkylene)- is optionally substituted with one or more substituents independently selected from D, F, Cl, $N_3$, CN, OH, SH, $NH_2$, $C_1$-$C_4$ alkyl, $C_1$-$C_4$ alkoxy, $C_1$-$C_4$ alkylthio and $C_1$-$C_4$ alkylamino.

16. The compound according to claim 2, wherein each $R^5$, $R^6$ and $R^7$ is independently H, D, F, Cl, $NO_2$, CN, $NH_2$, —C(=O)$R^{10}$, —C(=O)$OR^{10}$, —C(=O)$NR^{11}R^{11a}$, —($C_1$-

$C_6$ alkylene)-C(=O)NR$^{11}$R$^{11a}$, —OC(=O)R$^{10}$, —N(R$^{11}$)C(=O)R$^{10}$, —S(=O)R$^{10}$, —S(=O)$_2$R$^{10}$, —S(=O)$_2$OR$^{10}$, —S(=O)$_2$NR$^{11}$R$^{11a}$, —N(R$^{11}$)S(=O)$_2$R$^{10}$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ alkylthio, $C_1$-$C_6$ alkylamino, $C_3$-$C_{10}$ cycloalkyl, ($C_3$-$C_{10}$ cycloalkyl)-($C_1$-$C_6$ alkylene)-, $C_2$-$C_{10}$ heterocyclyl, ($C_2$-$C_{10}$ heterocyclyl)-($C_1$-$C_6$ alkylene)-, $C_6$-$C_{10}$ aryl, ($C_6$-$C_{10}$ aryl)-($C_1$-$C_6$ alkylene)-, $C_1$-$C_9$ heteroaryl or ($C_1$-$C_9$ heteroaryl)-($C_1$-$C_6$ alkylene)-, with the proviso that at least one of R$^5$, R$^6$ and R$^7$ is not H, wherein each of $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ alkylthio, $C_1$-$C_6$ alkylamino, $C_3$-$C_{10}$ cycloalkyl, ($C_3$-$C_{10}$ cycloalkyl)-($C_1$-$C_6$ alkylene)-, $C_2$-$C_{10}$ heterocyclyl, ($C_2$-$C_{10}$ heterocyclyl)-($C_1$-$C_6$ alkylene)-, $C_6$-$C_{10}$ aryl, ($C_6$-$C_{10}$ aryl)-($C_1$-$C_6$ alkylene)-, $C_1$-$C_9$ heteroaryl and ($C_1$-$C_9$ heteroaryl)-($C_1$-$C_6$ alkylene)- is optionally substituted with one or more substituents independently selected from D, F, Cl, N$_3$, CN, OH, SH, NH$_2$, $C_1$-$C_6$ alkyl, $C_1$-$C_6$ alkoxy, $C_1$-$C_6$ alkylthio and $C_1$-$C_6$ alkylamino; or wherein each R$^5$, R$^6$ and R$^7$ is independently H, D, F, Cl, NO$_2$, CN, NH$_2$, —C(=O)R$^{10}$, —C(=O)OR$^{10}$, —C(=O)NR$^{11}$R$^{11a}$, —(C$_1$-C$_4$ alkylene)-C(=O)NR$^{11}$R$^{11a}$, —OC(=O)R$^{10}$, —N(R$^{11}$)C(=O)R$^{10}$, —S(=O)R$^{10}$, —S(=O)$_2$R$^{10}$, —S(=O)$_2$OR$^{10}$, —S(=O)$_2$NR$^{11}$R$^{11a}$, —N(R$^{11}$)S(=O)$_2$R$^{10}$, $C_1$-$C_4$ alkyl, $C_1$-$C_4$ haloalkyl, $C_1$-$C_4$ alkoxy, $C_1$-$C_4$ alkylthio or $C_1$-$C_4$ alkylamino, with the proviso that at least one of R$^5$, R$^6$ and R$^7$ is not H, wherein each of $C_1$-$C_4$ alkyl, $C_1$-$C_4$ haloalkyl, $C_1$-$C_4$ alkoxy, $C_1$-$C_4$ alkylthio and $C_1$-$C_4$ alkylamino is optionally substituted with one or more substituents independently selected from D, F, Cl, N$_3$, CN, OH, SH, NH$_2$, $C_1$-$C_4$ alkyl, $C_1$-$C_4$ alkoxy, $C_1$-$C_4$ alkylthio and $C_1$-$C_4$ alkylamino.

17. The compound according to claim 2, wherein each R$^{10}$ is independently H, D, $C_1$-$C_6$ alkyl, $C_1$-$C_6$ haloalkyl or $C_3$-$C_{10}$ cycloalkyl, wherein each of $C_1$-$C_6$ alkyl, $C_1$-$C_6$ haloalkyl and $C_3$-$C_{10}$ cycloalkyl is optionally substituted with one or more substituents independently selected from D, F, Cl, N$_3$, CN, OH, SH, NH$_2$, $C_1$-$C_6$ alkyl, $C_1$-$C_6$ alkoxy, $C_1$-$C_6$ alkylthio and $C_1$-$C_6$ alkylamino; and each R$^{11}$ and R$^{11a}$ is independently H, D, $C_1$-$C_6$ alkyl, $C_1$-$C_6$ haloalkyl or $C_3$-$C_{10}$ cycloalkyl, or R$^{11}$ and R$^{11a}$, together with the nitrogen atom to which they are attached, form a $C_2$-$C_{10}$ heterocyclic ring, wherein each of $C_1$-$C_6$ alkyl, $C_1$-$C_6$ haloalkyl, $C_3$-$C_{10}$ cycloalkyl and $C_2$-$C_{10}$ heterocyclic ring is optionally substituted with one or more substituents independently selected from D, F, Cl, N$_3$, CN, OH, SH, NH$_2$, $C_1$-$C_6$ alkyl, $C_1$-$C_6$ alkoxy, $C_1$-$C_6$ alkylthio and $C_1$-$C_6$ alkylamino.

18. The compound according to claim 7, wherein R$^1$ is H, D, F, Cl, CN, OH, NH$_2$, Me, Et, n-Pr, i-Pr, —CF$_3$, —OMe, —OEt, —O(i-Pr), —O(t-Bu) or —NMe$_2$.

19. The compound according to claim 7, wherein each of R$^5$, R$^6$ and R$^7$ is independently H, D, F, Cl, NO$_2$, CN, NH$_2$, —C(=O)H, —C(=O)OH, —C(=O)OMe, —C(=O)NH$_2$, —CH$_2$—C(=O)NH$_2$, —C(=O)NMe$_2$, Me, Et, n-Pr, i-Pr, —CF$_3$, —OMe, —OEt, —O(i-Pr), —O(t-Bu) or —NMe$_2$, with the proviso that at least one of R$^5$, R$^6$ and R$^7$ is not H.

* * * * *